(12) United States Patent
Zhang et al.

(10) Patent No.: US 10,144,737 B2
(45) Date of Patent: Dec. 4, 2018

(54) SUBSTITUTED ETHYNYL HETEROBICYCLIC COMPOUNDS AS TYROSINE KINASE INHIBITORS

(71) Applicant: ETERNITY BIOSCIENCE INC., Cranbury, NJ (US)

(72) Inventors: Minsheng Zhang, Greenbrook, NJ (US); Yinfa Yan, Bedminster, NJ (US)

(73) Assignee: JIANGSU HENGRUI MEDICINE CO., LTD., Lianyungang (CN)

( * ) Notice: Subject to any disclaimer, the term of this patent is extended or adjusted under 35 U.S.C. 154(b) by 53 days.

(21) Appl. No.: 15/309,396

(22) PCT Filed: Oct. 20, 2014

(86) PCT No.: PCT/US2014/061369
§ 371 (c)(1),
(2) Date: Nov. 7, 2016

(87) PCT Pub. No.: WO2015/178955
PCT Pub. Date: Nov. 26, 2015

(65) Prior Publication Data
US 2017/0114063 A1   Apr. 27, 2017

Related U.S. Application Data

(60) Provisional application No. 62/000,321, filed on May 19, 2014.

(51) Int. Cl.
C07D 487/04 (2006.01)
C07D 473/34 (2006.01)

(52) U.S. Cl.
CPC ......... *C07D 487/04* (2013.01); *C07D 473/34* (2013.01)

(58) Field of Classification Search
CPC ............................ C07D 487/04; C07D 473/34
See application file for complete search history.

(56) References Cited

U.S. PATENT DOCUMENTS

| 2005/0009845 A1 | 1/2005 | Caferro et al. |
| 2013/0079324 A1 | 3/2013 | Cheng et al. |
| 2013/0345194 A1 | 12/2013 | Schou et al. |

FOREIGN PATENT DOCUMENTS

| WO | WO2013061305 | * 5/2013 | ........... C07D 473/16 |
| WO | WO 2014/044691 A1 | 3/2014 | |
| WO | WO 2014/048869 A1 | 4/2014 | |
| WO | WO2014075393 | * 5/2014 | ........... C07D 473/34 |

OTHER PUBLICATIONS

Borrmann et al. (J. Med. Chem. 2009, 52, p. 5974-5989).*
Shi et al. (Bioorg. Med. Chem. Lett. 24 (2014), p. 2206-2211).*
Kubinyi (3D QSAR in Drug Design: Ligand-Protein Interactions and Molecular Similarity, vol. 2-3, Springer, 1998, 800 pages). p. 243-44 provided.*
Wermuth, The Practice of Medicinal Chemsitry, 2d ed. (2003), 768 pages. Chs. 9-10 provided.*
Berg, Leslie J., et al., "Tec Family Kinases in T Lymphocyte Development and Function," *Annu. Rev. Immunol.* vol. 23, (2005), pp. 549-600.
Bomben, Andrea, et al., "A New Synthesis of 2-Aryloxypropionic Acids Derivatives via Selective Mono-C-Methylation of Methyl Aryloxyacetates and Aryloxyacetonitriles with Dimethyl Carbonate," *Tetrahedron Letters*, vol. 51, No. 42, (1995), pp. 11573-11580.
Edwards, Johnathan C.W., M.D., et al., "Efficacy of B-Cell-Targeted Therapy with Rituximab in Patients with Rheumatoid Arthritis," *The New England Journal of Medicine*, vol. 350, (2004), pp. 2572-2581.
Favas, Catarina, et al., "B-Cell-Depletion Therapy in SLE—What Are the Current Prospects for Its Acceptance?" *Nature Reviews Rheumatology*, vol. 5, (2009), pp. 711-716.
Hauser, Stephen L., M.D. et al., "B-Cell Depletion With Rituximab in Relapsing-Remitting Multiple Sclerosis," *The New England Journal of Medicine*, vol. 358, (2008), pp. 676-688.
Honigberg, Lee A., et al., "The Bruton Tyrosine Kinase Inhibitor PCI-32765 Blocks B-Cell Activation and Is Efficacious in Models of Autoimmune Disease and B-Cell Malignancy," *Proceedings of the National Academy of Sciences* (PNAS), vol. 107, No. 29, (2010), pp. 13075-13080.
Mohamed, Abdalla, et al., "Bruton's Tyrosine Kinase (Btk): Function, Regulation, and Transformation with Special Emphasis on the PH Domain," *Immunological Reviews*, vol. 228, (2009), pp. 58-73.
Ohe, Frank von der, et al., "Z- or E-Configured γ-Alkylidenebutenolides From A 2-(Trimethylsiloxy)Furan and Iodomethacrolein— Stereoselective Synthesis of Z-and E-Freelingyne," *Tetrahedron Letters* 39 (1998), pp. 1909-1910.
Pearson, William H., et al., "Approach to 6a-Epipretazettine and 6a-Epiprecriwelline via an Intramolecular 2-Azaallyl Anion Cycloaddition Reaction," *Journal of Organic Chemistry*, vol. 58, (1994), pp. 5662-5671.

(Continued)

*Primary Examiner* — Robert H Havlin
(74) *Attorney, Agent, or Firm* — Brinks Gilson & Lione; Yuezhong Feng

(57) ABSTRACT

The present disclosure provides a compound of formula (I) and the use thereof for the therapeutic treatment of human cancers including B-cell lymphoma and autoimmune diseases such as rheumatoid arthritis, systemic lupus erythematosus, and multiple sclerosis.

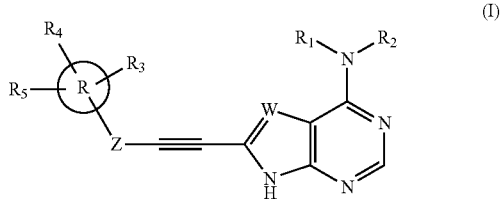

12 Claims, No Drawings

(56) References Cited

OTHER PUBLICATIONS

Ponader, Sabine, et al., "The Bruton Tyrosine Kinase Inhibitor PCI-32765 Thwarts Chronic Lymphocytic Leukemia Cell Survival and Tissue Homing in Vitro and in Vivo," *Blood*, vol. 119, No. 5, (2012), pp. 1182-1189.
Rigby, James H., et al., "Studies on the Narciclasine Alkaloids: Total Synthesis of (+)-Narciclasine and (+)-Pancratistatin," *Journal American Chemical Society*, vol. 122, (2000), pp. 6624-6628.
Thomas Jeffrey D., et al., "Colocalization of X-Linked Agammaglobulinemia and X-Linked Immunodeficiency Genes," *Science*, vol. 261, (1993), pp. 355-358.
Walser, Armin, et al., "Triazolobenzo- and Triazolothienodiazepines as Potent Antagonists of Platelet Activating Factor," *Journal of Med Chem.*, vol. 34, (1991), pp. 1209-1221.
International Search Report and Written Opinion to PCT Application No. PCT/US2014/61369, dated Mar. 31, 2015, (7p).
Schindler, Diana, et al., "*Rigid Rod and Tetrahedral Hybrid Compounds Featuring Nucleobase and Nucleoside End-Capped Structures*," Org. Biomol. Chem., vol. 7, (2009), pp. 3549-3560.
Extended European Search Report to European Patent Application No. 14892753.6, dated Oct. 9, 2017, (8p).

\* cited by examiner

SUBSTITUTED ETHYNYL HETEROBICYCLIC COMPOUNDS AS TYROSINE KINASE INHIBITORS

This application is the national phase application of PCT Application No. PCT/US2014/061369, filed Oct. 20, 2014, which claims priority to U.S. Provisional Patent Application Se. No. 62/000,321, filed May 19, 2014, the entireties of both of which are incorporated herein by reference.

TECHNICAL FIELD

The present invention describes a series of new compounds that display potent inhibition against Bruton's tyrosine kinase and, therefore, may provide a potential therapeutic approach to treating human cancers including B-cell lymphoma, and autoimmune diseases such as rheumatoid arthritis, systemic lupus erythematosus, and multiple sclerosis.

BACKGROUND

Bruton's tyrosine kinase (Btk) is a non-receptor cytoplasmic tyrosine kinase belonging to the Tec family of kinases, members of which also include Tec, Itk, Txk, and Bmx. Most of these kinases are predominantly expressed in hematopoietic cells and play important roles in relaying signal transductions from cell surface receptors to direct cell development, differentiation, and other functions (Berg J J et al. Annual Review of Immunology, 2005; 23:549-600). Btk is critical for B-cell development, differentiation, maturation, and signaling (Mohamed A J et al. Immunological Reviews, 2009; 228:58-73). Loss-of-function mutations of Btk cause X-linked agammaglobulinemia (XLA) in humans and X-linked immunodeficiency in mice (Thomas J D et al. Science 1993; 261:355-358). Patients with XLA have normal pre-B cell populations in their bone marrow but these cells fail to mature and enter the circulation. Therefore, these patients essentially have no circulating B cells and are incapable of producing antibodies.

BTK plays pivotal roles in B-cell proliferation and activation mediated by B-cell receptor (BCR). Upon BCR activation, Btk is translocated to the plasma membrane where it is phosphorylated and subsequently initiates a cascade of signaling events including activation of phospholipase Cγ2 (PLCγ2) and eventually leading to calcium mobilization and transcriptional regulation involving nuclear factor kappa B (NF-κB) (Mohamed A J et al. Immunological Reviews 2009; 228:58-73). Because of the indispensable roles in BCR signaling pathway, it is believed that the kinase activity of Btk is critical for development and maintenance of a wide variety of B-cell malignancies, including chronic lymphocytic leukemia (CLL) and a number of non-Hodgkin's lymphoma (NHL) subtypes, mantle cell lymphoma (MCL), and diffuse large B-cell lymphoma (DLBCL) (Ponader S. et al. Blood 2012, 119:1182-1189; Honigberg L A et al. Proceedings of the National Academy of Sciences, 2010, 107:13075-13080). In addition, the role of B-cell in the pathogenesis of rheumatoid arthritis, systemic lupus erythematosus, multiple sclerosis, and other immune disorders has been clinically demonstrated (Edwards J C et al. The New England Journal of Medicine, 2004, 350:2572-2581; Favas C et al. Nature Review Rheumatology, 2009, 5:711-716; Hauset S L et al. The New England Journal of Medicine, 2008, 358:676-688). Therefore, targeting Btk with small molecule inhibitors may provide therapeutic benefit for the treatment of B-cell malignancies and autoimmune diseases.

SUMMARY OF THE DISCLOSURE

In one aspect, the compounds are of formula (I):

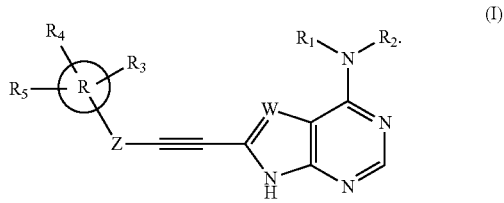

Z is selected from the group consisting of —$(CH_2)_m$—, —$O(CH_2)_m$—, —$NR^6(CH_2)_m$— and a bond; and where m is an integer from 1-3.

W is $CR^7$ or N.

R is a cyclic group selected from the group consisting of unsubstituted or substituted aryl, unsubstituted or substituted bicyclic aryl, unsubstituted or substituted heteroaryl, and unsubstituted or substituted bicyclicheteroaryl.

$R^1$ and $R^2$ are independently selected from the group consisting of H, —$COR^8$, unsubstituted or substituted alkyl, unsubstituted or substituted alkenyl, unsubstituted or substituted alkynyl, unsubstituted or substituted $C_3$-$C_8$ cycloalkyl, unsubstituted or substituted $C_3$-$C_8$ cycloheteroalkyl, unsubstituted or substituted aryl, and unsubstituted or substituted heteroaryl; or $R^1$ and $R^2$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

$R^3$, $R^4$ and $R^5$ are each independently selected from the group consisting of H, halogen, —CN, —$CF_3$, —$OCF_3$, —$OR^9$, —$OCOR^{10}$, —$CO_2R^{11}$, —$COR^{12}$, —$CONR^{13}R^{14}$, —$NR^{15}R^{16}$, —$NR^{17}COR^{18}$, —$NR^{19}SO_2R^{20}$, —$SO_wR^{21}$, —$SO_2NR^{22}R^{23}$, unsubstituted or substituted alkyl, unsubstituted or substituted alkenyl, unsubstituted or substituted alkynyl, unsubstituted or substituted $C_3$-$C_8$ cycloalkyl, unsubstituted or substituted $C_3$-$C_8$ cycloheteroalkyl, unsubstituted or substituted aryl, and unsubstituted or substituted heteroaryl; and where w is an integer from 0-2.

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from the group consisting of unsubstituted or substituted alkyl, unsubstituted or substituted alkenyl, unsubstituted or substituted alkynyl, unsubstituted or substituted $C_3$-$C_8$ cycloalkyl, unsubstituted or substituted $C_3$-$C_8$ cycloheteroalkyl, unsubstituted or substituted aryl, and unsubstituted or substituted heteroaryl; or $R^{13}$ and $R^{14}$, $R^{15}$ and $R^{16}$, or $R^{22}$ and $R^{23}$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In another aspect, a compound has a formula selected from the group consisting of formulae (II) and (III):

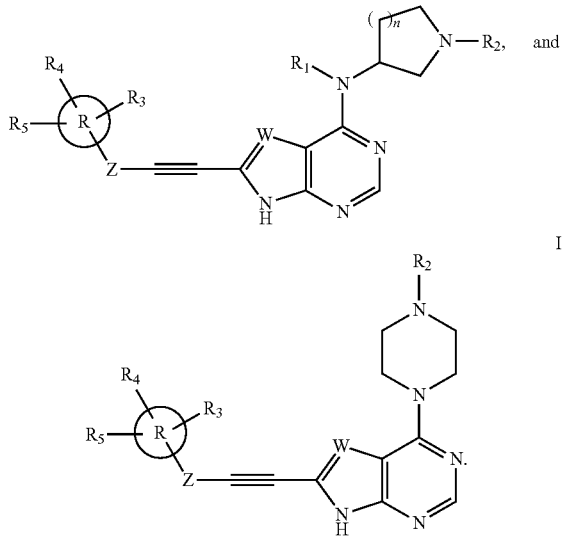

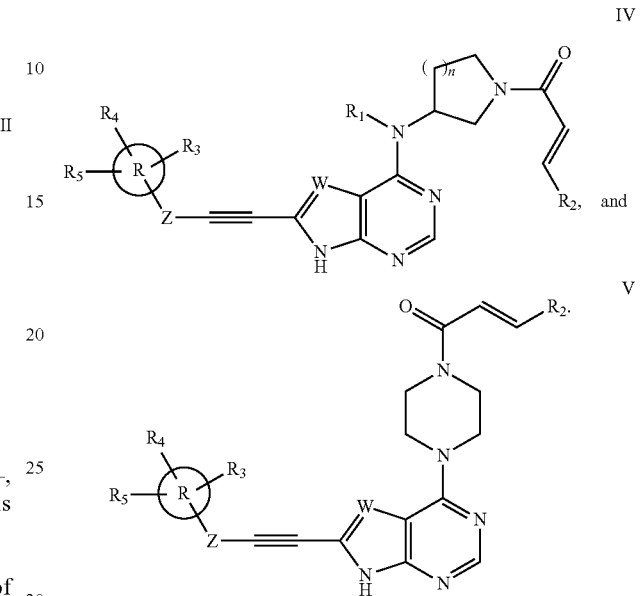

Z is selected from the group consisting of —(CH$_2$)$_m$—, —O(CH$_2$)$_m$—, —NR$^6$(CH$_2$)$_m$— and a bond; and where m is an integer from 1-3.

W is CR$^7$ or N.

R is a cyclic group selected from the group consisting of unsubstituted or substituted aryl, unsubstituted or substituted bicyclic aryl, unsubstituted or substituted heteroaryl, and unsubstituted or substituted bicyclicheteroaryl.

R$^1$ is selected from the group consisting of H, unsubstituted or substituted alkyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl.

R$^2$ is selected from the group consisting of H, CN, —COR$^8$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, unsubstituted or substituted heteroaryl, oxirane, and —CH$_2$NR'R".

R$^3$, R$^4$ and R$^5$ are each independently selected from the group consisting of H, halogen, —CN, —CF$_3$, —OCF$_3$, —OR$^9$, —OCOR$^{10}$, —CO$_2$R$^{11}$, —COR$^{12}$, —CONR$^{13}$R$^{14}$, —NR$^{15}$R$^{16}$, —NR$^{17}$COR$^{18}$, —NR$^{19}$SO$_2$R$^{20}$, —SO$_w$R$^{21}$, —SO$_2$NR$^{22}$R$^{23}$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl. w is an integer from 0-2.

R', R", R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently selected from the group consisting of unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; or R$^{13}$ and R$^{14}$, R$^{15}$ and R$^{16}$, or R$^{22}$ and R$^{23}$ may combine with an atom or atoms to which they are attached to form unsubstituted or substituted C$_{3-12}$ cycloalkyl, unsubstituted or substituted 3- to 12-membered heterocyclic, unsubstituted or substituted C$_{6-12}$ aryl, or unsubstituted or substituted 5- to 12-membered heteroaryl.

n is an integer from 0-3.

In still another aspect, a compound has a formula selected from the group consisting of formulae (IV) and (V):

Z is selected from the group consisting of —(CH$_2$)$_m$—, —O(CH$_2$)$_m$—, —NR$^6$(CH$_2$)$_m$— and a bond; and where m is an integer from 1-3.

W is CR$^7$ or N.

R is a cyclic group selected from the group consisting of unsubstituted or substituted aryl, unsubstituted or substituted bicyclic aryl, unsubstituted or substituted heteroaryl, and unsubstituted or substituted bicyclicheteroaryl.

R$^1$ is selected from the group consisting of H, unsubstituted or substituted alkyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl.

R$^2$ is selected from the group consisting of H, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, unsubstituted or substituted heteroaryl, oxirane, and —CH$_2$NR'R".

R$^3$, R$^4$ and R$^5$ are each independently selected from the group consisting of H, halogen, —CN, —CF$_3$, —OCF$_3$, —OR$^9$, —OCOR$^{10}$, —CO$_2$R$^{11}$, —COR$^{12}$, —CONR$^{13}$R$^{14}$, —NR$^{15}$R$^{16}$, —NR$^{17}$COR$^{18}$, —NR$^{19}$SO$_2$R$^{20}$, —SO$_w$R$^{21}$, —SO$_2$NR$^{22}$R$^{23}$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; and where w is an integer from 0-2.

R', R", R$^6$, R$^7$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently selected from the group consisting of unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; or $R^{13}$ and $R^{14}$, $R^{15}$ and $R^{16}$, or $R^{22}$ and $R^{23}$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

n is an integer from 0-3.

DETAILED DESCRIPTION OF THE DISCLOSURE

This invention relates generally to compounds that modulate protein tyrosine kinase activity, methods of synthesizing, and using such compounds in therapeutic methods.

When describing the compounds, compositions, methods and processes of this disclosure, the following terms have the following meanings, unless otherwise indicated.

The term "halogen" or "halo" means a chlorine, bromine, iodine, or fluorine atom.

The term "alkyl" means a hydrocarbon group that may be linear, cyclic, or branched or a combination thereof having the number of carbon atoms designated (i.e., $C_{2-12}$ means two to twelve carbon atoms). Examples of alkyl groups include methyl, ethyl, n-propyl, isopropyl, n-butyl, t-butyl, isobutyl, sec-butyl, cyclohexyl, cyclopentyl, (cyclohexyl) methyl, cyclopropylmethyl, bicyclo[2.2.1]heptane, bicyclo [2.2.2]octane, etc. Alkyl groups can be substituted or unsubstituted, unless otherwise indicated. Examples of substituted alkyl groups include haloalkyl, thioalkyl, aminoalkyl, and the like.

The term "alkenyl" means a hydrocarbon group that contains at least one carbon-to-carbon double bond. Alkenyl groups can include, e.g., allyl, 1-butenyl, 2-hexenyl and 3-octenyl groups. Alkenyl groups can be substituted or unsubstituted, unless otherwise indicated.

The term "alkynyl" means a hydrocarbon group that contains at least one carbon-to-carbon triple bond. Alkynyl groups can include, e.g., ethynyl, propargyl, and 3-hexynyl. Alkynyl groups can be substituted or unsubstituted, unless otherwise indicated.

The term "aryl" means a polyunsaturated, aromatic hydrocarbon group having 5-10 atoms and forming a single ring (monocyclic, preferably with 6 atoms such as phenyl) or multiple rings (bicyclic (preferably with 10 atoms such as naphthyl) or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing 5-10 atoms and at least one heteroatom (such as S, N, O, Si), where the heteroaryl group may be monocyclic (with preferably 5 or 6 atoms) or bicyclic (with preferably 9 or 10 atoms). Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "cycloalkyl" refers to saturated monocyclic, bicyclic, tricyclic, or other polycyclic hydrocarbon groups. Any atom can be substituted, e.g., by one or more substituents. A ring carbon serves as the point of attachment of a cycloalkyl group to another moiety. Cycloalkyl groups can contain fused rings. Fused rings are rings that share a common carbon atom. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "heterocyclyl" or "heterocyclic", which are synonymous as used herein, means a saturated or unsaturated non-aromatic ring containing at least 5-10 atoms (preferably 5 or 6) and at least one heteroatom (typically 1 to 5 heteroatoms) selected from nitrogen, oxygen or sulfur. The heterocyclyl ring may be monocyclic (with preferably 5 or 6 atoms) or bicyclic (with preferably 9 or 10 atoms). The ring system has 1-4 heteroatoms if monocyclic, 1-8 heteroatoms if bicyclic, or 1-10 heteroatoms if tricyclic, the heteroatoms selected from O, N, or S (and mono and dioxides thereof, e.g., $N \rightarrow O^-$, $S(O)$, $SO_2$). The heterocyclyl groups can contain fused rings. Fused rings are rings that share a common carbon atom. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "alkoxy" refers to an —O-alkyl radical. The term "mercapto" refers to an SH radical. The term "thioalkoxy" refers to an —S-alkyl radical. The terms "aryloxy" and "heteroaryloxy" refer to an —O-aryl radical and —O-heteroaryl radical, respectively. The terms "thioaryloxy" and "thioheteroaryloxy" refer to an —S-aryl radical and —S— heteroaryl radical, respectively.

The term "substituent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, heteroaryl, arylcycloalkyl, heteroarylcycloalkyl, arylcycloalkyl, heteroarylcycloalkenyl, arylheterocyclyl, heteroarylheterocyclyl, arylheterocycloalkenyl, or heteroarylheterocycloalkenyl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

All of the above terms (e.g., "alkyl," "aryl," "heteroaryl" etc.), in some embodiments, include both substituted and unsubstituted forms of the indicated groups. These groups may be substituted multiple times, as chemically allowed.

The term "composition" as used herein is intended to encompass a product comprising the specified ingredients in the specified amounts, as well as any product which results, directly or indirectly, from combination of the specified ingredients in the specified amounts. By "pharmaceutically-acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or *arachis* oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", J. Pharmaceutical Science, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient. Salts are especially the pharmaceutically acceptable salts of compounds of formula (I).

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition (such as a cancer) in a patient, such as a mammal (particularly a human or a companion animal) which includes:

ameliorating the disease or medical condition, i.e., eliminating or causing regression of the disease or medical condition in a patient;

suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention.

Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14($^{14}$C). All isotopic variations of the compounds of the present invention, whether radioactive or not, are intended to be encompassed within the scope of the present invention.

A compound of formula (I) can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

A compound according to the invention is not only for management of humans, but also for the treatment of other warm-blooded animals, for example of commercially useful animals. Such a compound may also be used as a reference standard in the test systems described above to permit a comparison with other compounds.

The present disclosure provides a compound of formula (I):

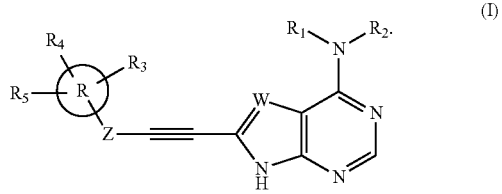

Z is selected from the group consisting of —(CH$_2$)$_m$—, —O(CH$_2$)$_m$—, —NR$^6$(CH$_2$)$_m$— and a bond; and where m is an integer from 1-3.

W is CR$^7$ or N.

R is a cyclic group selected from the group consisting of unsubstituted or substituted aryl, unsubstituted or substituted bicyclic aryl, unsubstituted or substituted heteroaryl, and unsubstituted or substituted bicyclicheteroaryl.

R$^1$ and R$^2$ are independently selected from the group consisting of H, —COR$^8$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; or R$^1$ and R$^2$ may combine with an atom or atoms to which they are attached to form unsubstituted or substituted C$_{3-12}$ cycloalkyl, unsubstituted or substituted 3- to 12-membered heterocyclic, unsubstituted or substituted C$_{6-12}$ aryl, or unsubstituted or substituted 5- to 12-membered heteroaryl.

R$^3$, R$^4$ and R$^5$ are each independently selected from the group consisting of H, halogen, —CN, —CF$_3$, —OCF$_3$, —OR$^9$, —OCOR$^{10}$, —CO$_2$R$^{11}$, —COR$^{12}$, —CONR$^{13}$R$^{14}$, —NR$^{15}$R$^{16}$, —NR$^{17}$COR$^{18}$, —NR$^{19}$SO$_2$R$^{20}$, —SO$_w$R$^{21}$, —SO$_2$NR$^{22}$R$^{23}$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; and where w is an integer from 0-2.

R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently selected from the group consisting of unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; or R$^{13}$ and R$^{14}$, R$^{15}$ and R$^{16}$, or R$^{22}$ and R$^{23}$ may combine with an atom or atoms to which they are attached to form unsubstituted or substituted C$_{3-12}$ cycloalkyl, unsubstituted or substituted 3- to 12-membered heterocyclic, unsubstituted or substituted C$_{6-12}$ aryl, or unsubstituted or substituted 5- to 12-membered heteroaryl.

In some embodiments, Z is selected from the group consisting of —CH$_2$—, —OCH$_2$—, and a bond.

In some embodiments, R is selected from the group consisting of phenyl, naphthalenyl, benzodioxolyl, benzofuranyl, benzothiophenyl, thiophenyl, quinolinyl, cyclohexyl, furanyl, pyrazolyl, tetrahydropyranyl, and indazolyl.

In some embodiments, R$^3$, R$^4$ and R$^5$ are each independently selected from the group consisting of H, F, Cl, —OCH$_3$, —OCF$_3$, —CH$_3$, —CF$_3$, and —CN.

In some embodiments, R$^3$, R$^4$ and R$^5$ are H. In some embodiments, at least one of R$^3$, R$^4$ and R$^5$ is halogen. In some embodiments, at least two of R$^3$, R$^4$ and R$^5$ are halogen.

In some embodiments, W is CH or N.

In some embodiments, R$^1$ and R$^2$ combine the nitrogen to which they are attached to form an unsubstituted or substituted piperazinyl. In some embodiments, the piperazinyl is substituted with a substituent selected from the group consisting of —C(O)CH=CH$_2$, —C(O)CH=CHCH$_2$N(CH$_3$)$_2$, and

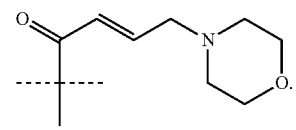

In some embodiments, R$^1$ is H.

In some embodiments, R$^2$ is an unsubstituted or substituted pyrrolidinyl.

In some embodiments, R$^2$ is pyrrolidinyl substituted with a substituent selected from the group consisting of —C(O)CH=CH$_2$, —C(O)CH=CHCH$_2$N(CH$_3$)$_2$, —C(O)CH=CHCH$_2$NH(CH$_3$), —C(O)CH=CHCH$_3$,

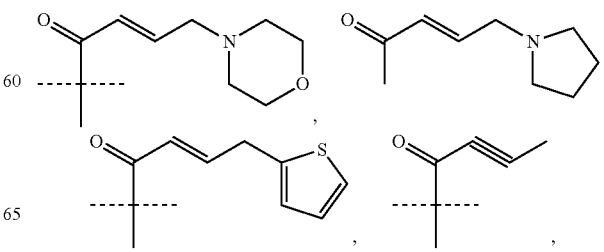

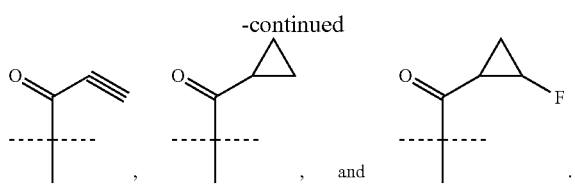

In some embodiments, $R^2$ is an unsubstituted or substituted piperidinyl.

In some embodiments, $R^2$ is piperidinyl substituted —C(O)CH=CH$_2$. In some embodiments, $R^2$ is an unsubstituted or substituted phenyl. In some embodiments, $R^2$ is phenyl substituted with —NHC(O)CH=CH$_2$.

In another aspect, a compound has a formula selected from the group consisting of formulae (II) and (III):

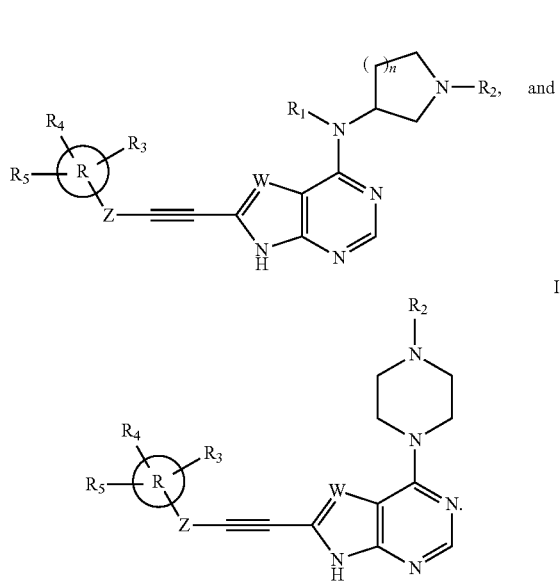

Z is selected from the group consisting of —(CH$_2$)$_m$—, —O(CH$_2$)$_m$—, —NR$^6$(CH$_2$)$_m$— and a bond; and where m is an integer from 1-3.

W is CR$^7$ or N.

R is selected from the group consisting of unsubstituted or substituted aryl, unsubstituted or substituted bicyclic aryl, unsubstituted or substituted heteroaryl, and unsubstituted or substituted bicyclicheteroaryl.

$R^1$ is selected from the group consisting of H, unsubstituted or substituted alkyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl.

$R^2$ is selected from the group consisting of H, CN, —COR$^8$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, unsubstituted or substituted heteroaryl, oxirane, and —CH$_2$NR'R".

$R^3$, $R^4$ and $R^5$ are each independently selected from the group consisting of H, halogen, —CN, —CF$_3$, —OCF$_3$, —OR$^9$, —OCOR$^{10}$, —CO$_2$R$^{11}$, —COR$^{12}$, —CONR$^{13}$R$^{14}$, —NR$^{15}$R$^{16}$, —NR$^{17}$COR$^{18}$, —NR$^{19}$SO$_2$R$^{20}$, —SO$_w$R$^{21}$, —SO$_2$NR$^{22}$R$^{23}$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl. w is an integer from 0-2.

R', R", $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from the group consisting of unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; or $R^{13}$ and $R^{14}$, $R^{15}$ and $R^{16}$, or $R^{22}$ and $R^{23}$ may combine with an atom or atoms to which they are attached to form unsubstituted or substituted C$_{3-12}$ cycloalkyl, unsubstituted or substituted 3- to 12-membered heterocyclic, unsubstituted or substituted C$_{6-12}$ aryl, or unsubstituted or substituted 5- to 12-membered heteroaryl.

n is an integer from 0-3.

In some embodiments, Z is selected from the group consisting of —CH$_2$—, —OCH$_2$—, and a bond.

In some embodiments, R is selected from the group consisting of phenyl, naphthalenyl, benzodioxolyl, benzofuranyl, benzothiophenyl, thiophenyl, quinolinyl, cyclohexyl, furanyl, pyrazolyl, tetrahydropyranyl, and indazolyl.

In some embodiments, $R^3$, $R^4$ and $R^5$ are each independently selected from the group consisting of H, F, Cl, —OCH$_3$, —OCF$_3$, —CH$_3$, —CF$_3$, and —CN.

In some embodiments, $R^3$, $R^4$ and $R^5$ are H. In some embodiments, at least one of $R^3$, $R^4$ and $R^5$ is halogen. In some embodiments, at least two of $R^3$, $R^4$ and $R^5$ are halogen.

In some embodiments, W is CH or N.

In some embodiments, $R^1$ is H.

In some embodiments, $R^2$ is selected from the group consisting of H, —COR$^8$, unsubstituted or substituted C$_1$-C$_6$ alkyl, C$_2$-C$_6$ alkenyl, and C$_2$-C$_6$ alkynyl. In some embodiments, $R^2$ is H. In some embodiments, $R^2$ is —CH$_2$NR'R". In some embodiments, $R^2$ is —CH$_2$N(CH$_3$)$_2$.

In some embodiments, $R^2$ is selected from the group consisting of —C(O)CH=CH$_2$, —C(O)CH=CHCH$_2$N(CH$_3$)$_2$, and

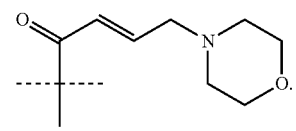

In some embodiments, $R^2$ is selected from the group consisting of —C(O)CH=CH$_2$, —C(O)CH=CHCH$_2$N(CH$_3$)$_2$, —C(O)CH=CHCH$_2$NH(CH$_3$), —NHC(O)CH=CH$_2$, —C(O)CH=CHCH$_3$,

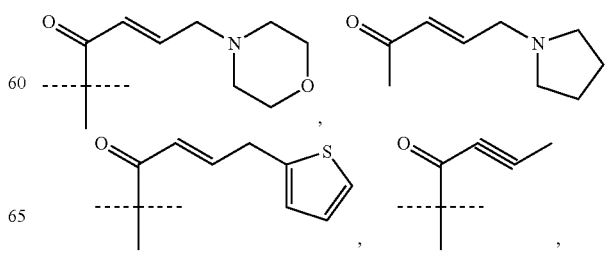

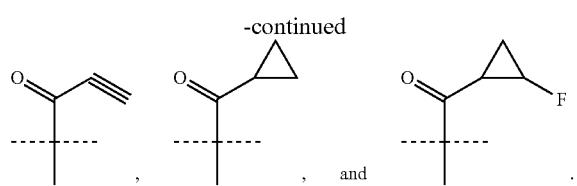
, and .

In another aspect, a compound has a formula selected from the group consisting of formulae (IV) and (V):

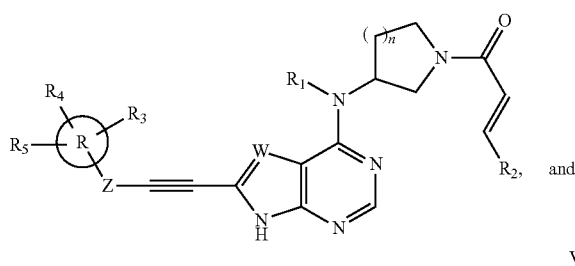

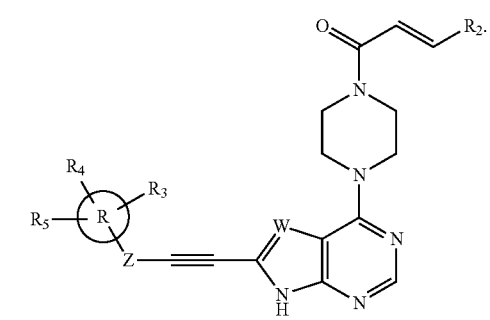

Z is selected from the group consisting of —(CH$_2$)$_m$—, —O(CH$_2$)$_m$—, —NR$^6$(CH$_2$)$_m$— and a bond; and where m is an integer from 1-3.

W is CR$^7$ or N.

R is a cyclic group selected from the group consisting of unsubstituted or substituted aryl, unsubstituted or substituted bicyclic aryl, unsubstituted or substituted heteroaryl, and unsubstituted or substituted bicyclicheteroaryl.

R$^1$ is selected from the group consisting of H, unsubstituted or substituted alkyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl.

R$^2$ is selected from the group consisting of H, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, unsubstituted or substituted heteroaryl, oxirane, and —CH$_2$NR'R".

R$^3$, R$^4$ and R$^5$ are each independently selected from the group consisting of H, halogen, —CN, —CF$_3$, —OCF$_3$, —OR$^9$, —OCOR$^{10}$, —CO$_2$R$^{11}$, —COR$^{12}$, —CONR$^{13}$R$^{14}$, —NR$^{15}$R$^{16}$, —NR$^{17}$COR$^{18}$, —NR$^{19}$SO$_2$R$^{20}$, —SO$_w$R$^{21}$, —SO$_2$NR$^{22}$R$^{23}$, unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; and where w is an integer from 0-2.

R', R", R$^6$, R$^7$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently selected from the group consisting of unsubstituted or substituted alkyl, unsubstituted or substituted alkenyl, unsubstituted or substituted alkynyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl; or R$^{13}$ and R$^{14}$, R$^{15}$ and R$^{16}$, or R$^{22}$ and R$^{23}$ may combine with an atom or atoms to which they are attached to form unsubstituted or substituted C$_{3-12}$ cycloalkyl, unsubstituted or substituted 3- to 12-membered heterocyclic, unsubstituted or substituted C$_{6-12}$ aryl, or unsubstituted or substituted 5- to 12-membered heteroaryl.

n is an integer from 0-3.

Z is selected from the group consisting of —(CH$_2$)$_m$—, —O(CH$_2$)$_m$—, —NR$^6$(CH$_2$)$_m$— and a bond; and where m is an integer from 1-3.

W is CR$^7$ or N.

R is a cyclic group selected from the group consisting of unsubstituted or substituted aryl, unsubstituted or substituted bicyclic aryl, unsubstituted or substituted heteroaryl, and unsubstituted or substituted bicyclicheteroaryl.

R$^1$ is selected from the group consisting of H, unsubstituted or substituted alkyl, unsubstituted or substituted C$_3$-C$_8$ cycloalkyl, unsubstituted or substituted C$_3$-C$_8$ cycloheteroalkyl, unsubstituted or substituted aryl, and unsubstituted or substituted heteroaryl.

In some embodiments, R$^2$ is selected from the group consisting of H, unsubstituted or substituted C$_1$-C$_6$ alkyl, C$_2$-C$_6$ alkenyl, and C$_2$-C$_6$ alkynyl. In some embodiments, R$^2$ is H. In some embodiments, R$^2$ is —CH$_2$NR'R". In some embodiments, R$^2$ is —CH$_2$N(CH$_3$)$_2$.

As used in the specification and claims, the term halogen designates Br, Cl, I or F, and the term cycloheteroalkyl designates a C$_5$-C$_7$ cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X$_1$ is NR, O or S.

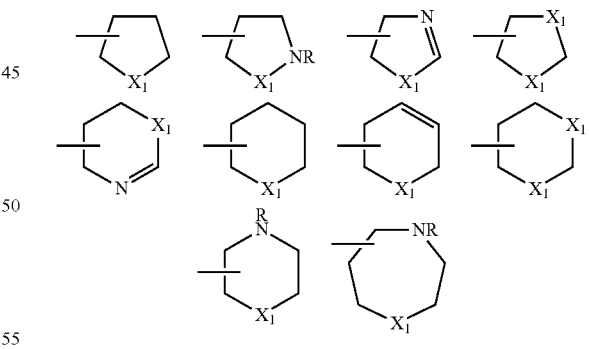

Similarly, as used in the specification and claims, the term heteroaryl designates a 5- to 10-membered aromatic ring system containing 1 or 2 heteroatoms, which may be the same or different, selected from N, O or S. Such heteroaryl ring systems (monocyclic or bicyclic) include but are not limited to: pyrrole, pyrazole furan, thiophene, indole, azaindole, oxazole, thiazole, isoxazole, isothiazole, imidazole, pyridine, pyrimidine, pyrazine, 1,3,4-oxadiazole, 1,2,4-triazole, 1H-tetrazole, benzoxazole, benzothiazole, benzofuran, benzisoxazole, benzimidazole, azabenzimidazole, indazole, quinazoline, and quinoline.

In the specification and claims, when the terms $C_1$-$C_6$ alkyl, $C_2$-$C_6$ alkenyl, $C_2$-$C_6$ alkynyl, $C_3$-$C_7$ cycloalkyl, cycloheteroalkyl, phenyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms, alkoxy, hydroxy or lower alkyl groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of Formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention may exist as one or more stereoisomers. The various stereoisomers include enantiomers, diastereomers, atropisomers, and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

The present disclosure includes a pharmaceutical composition comprising the compound of formula (I), and a pharmaceutically acceptable carrier.

The present disclosure includes a method of modulating protein tyrosine kinase activity, comprising contacting a cell with an effective amount of the compound of formula (I) or the pharmaceutically acceptable salt thereof.

A method of treating a condition or a disease mediated by protein tyrosine kinases, comprises administering to a subject a therapeutically effective amount of the compound of formula (I), or the pharmaceutically acceptable salt thereof. The condition includes cancers or blood diseases.

The compounds of the invention possess tyrosine kinase inhibitory activity. The inhibitory activities of the compounds of the invention are readily demonstrated, for example, using one or more of the assays described herein or known in the art.

The invention also provides methods of preparing the compounds of the invention and the intermediates used in those methods.

As used in the specification and claims, the term halogen designates Br, Cl, I or F and the term cycloheteroalkyl designates a $C_5$-$C_7$ cycloalkyl ring system containing 1 or 2 heteroatoms, which may be the same or different, selected from N, O or S and optionally containing one double bond.

Exemplary of the cycloheteroalkyl ring systems included in the term as designated herein are the following rings wherein $X_1$ is NR, O or S.

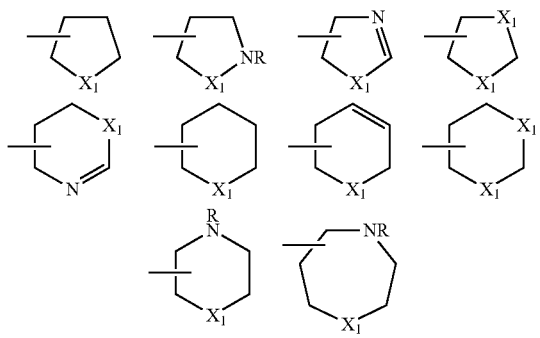

Similarly, as used in the specification and claims, the term heteroaryl designates a 5- to 10-membered aromatic ring system containing 1 or 2 heteroatoms, which may be the same or different, selected from N, O or S. Such heteroaryl ring systems (monocyclic or bicyclic) include but are not limited to: pyrrole, pyrazole furan, thiophene, indole, azaindole, oxazole, thiazole, isoxazole, isothiazole, imidazole, pyridine, pyrimidine, pyrazine, 1,3,4-oxadiazole, 1,2,4-triazole, 1H-tetrazole, benzoxazole, benzothiazole, benzofuran, benzisoxazole, benzimidazole, azabenzimidazole, indazole, quinazoline, quinoline.

In the specification and claims, when the terms $C_1$-$C_6$ alkyl, $C_2$-$C_6$ alkenyl, $C_2$-$C_6$ alkynyl, $C_3$-$C_7$ cycloalkyl, cycloheteroalkyl, phenyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms, alkoxy, hydroxy or lower alkyl groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula (I) and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds disclosed herein may exist as one or more stereoisomers. The various stereoisomers include enantiomers, diastereomers, atropisomers, and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula (I), the stereoisomers thereof and the pharmaceutically acceptable salts thereof.

The compounds of the invention may be present as a mixture of stereoisomers, individual stereoisomers, or as an optically active form.

Preferred compounds of the invention are those compounds of formulae (IV) and (V) wherein R is aryl, heteroaryl and bicyclicaryl. Aryl, heteroaryl, and bicyclicaryl groups are each optionally substituted with halogen, multi-substituted halogens, $CF_3$ or $OCF_3$. In some embodiments, $R^1$ is H. $R^3$ is a halogen or $OR^9$ where $R^9$ is H, an unsubstituted or substituted $C_1$-$C_6$ alkyl, an unsubstituted or substituted $C_2$-$C_6$ alkenyl, an unsubstituted or substituted $C_2$-$C_6$ alkynyl, an unsubstituted or substituted $C_3$-$C_8$ cycloalkyl, an unsubstituted or substituted $C_3$-$C_8$ cycloheteroalkyl, an unsubstituted or substituted aryl or an unsubstituted or substituted heteroaryl group.

EXAMPLES

The following examples illustrate the transformations described below in reaction schemes. The following abbreviations are used: TEA is triethylamine, DIPEA is N,N-diisopropylethylamine, HBTU is O-(Benzotriazol-1-yl)-N,N,N',N'-tetramethyluronium hexafluorophosphate, DMF is N,N-dimethylformamide, NMR is proton nuclear magnetic resonance, and MS is mass spectroscopy with (+) referring to the positive mode which generally gives a M+1 (or M+H) absorption where M=the molecular mass. All compounds are analyzed at least by MS and NMR.

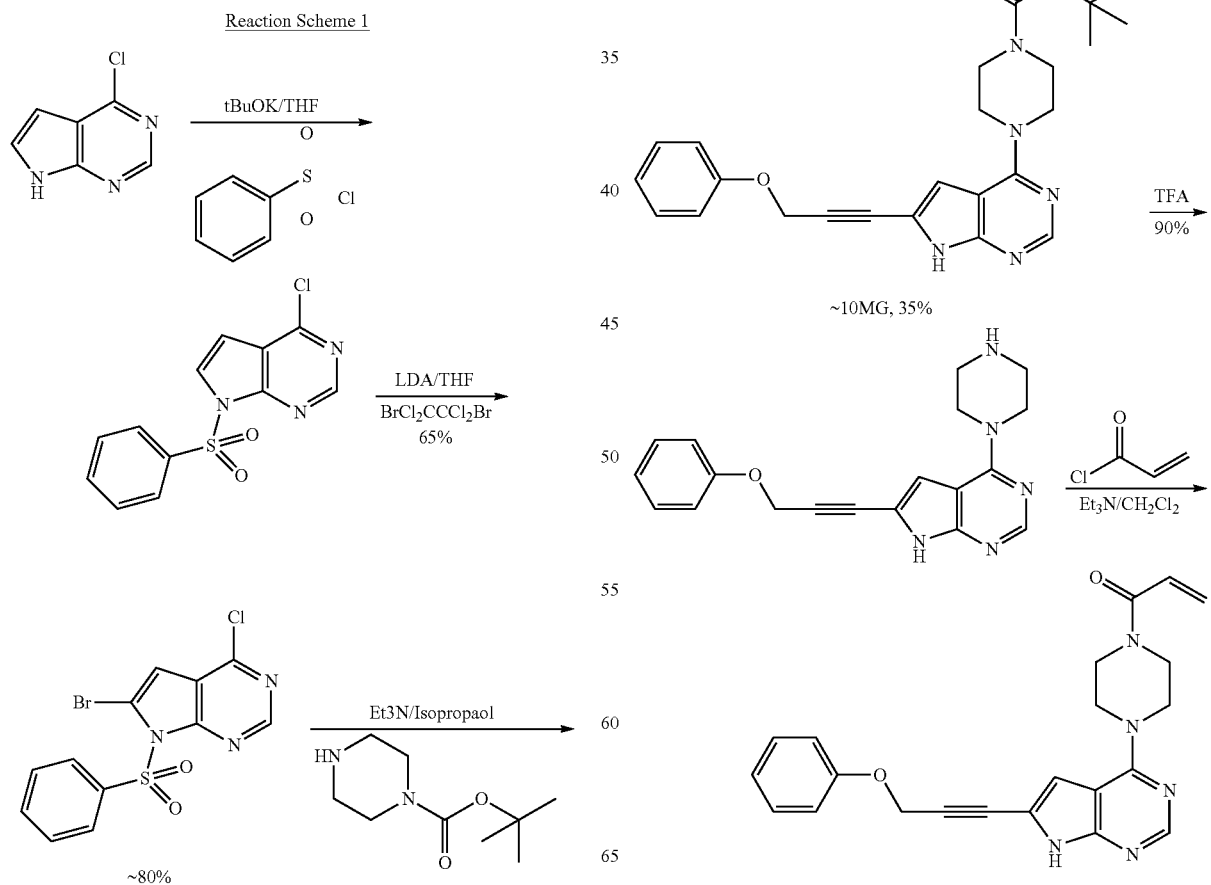

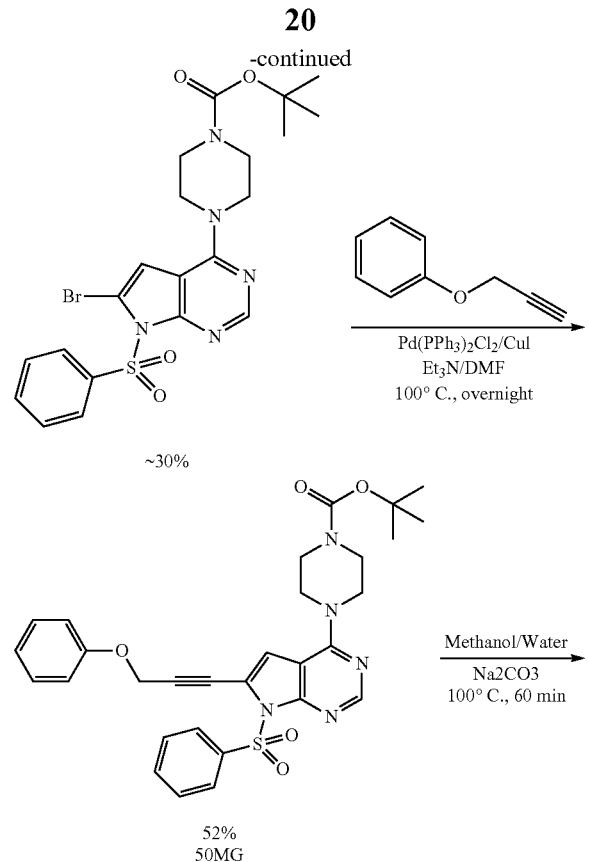

Example 1

1-(4-(6-(3-phenoxyprop-1-yn-1-yl)-7H-pyrrolo[2,3-d]pyrimidin-4-yl)piperazin-1-yl)prop-2-en-1-one

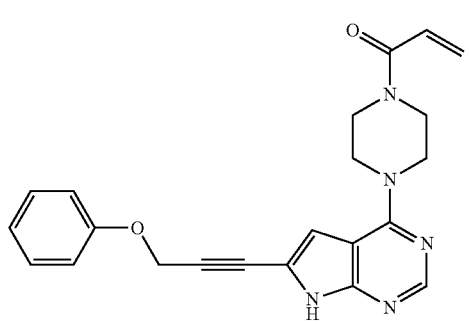 [SMILES: C=CC(=O)N1CCN(c2ncnc3[nH]c(C#CCOc4ccccc4)cc23)CC1]

Step 1. Preparation of 4-chloro-7-(phenylsulfonyl)-7H-pyrrolo[2,3-d]pyrimidine

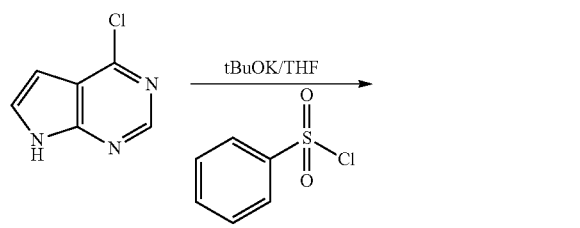

To a solution of 4-chloro-7H-pyrrolo[2,3-d]pyrimidine (10.00 g, 0.065 mol) in THF (300 mL) was added potassium tert-butoxide (9.13 g, 0.081 mol). The reaction mixture was stirred at room temperature for 20 minutes. As the reaction was mildly exothermic, the suspension was cooled with the aid of an ice water bath. Benzenesulfonyl chloride (10.4 mL, 0.082 mol) was then added drop-wise and the resulting suspension stirred for a further 3 hours. Then water (25 mL) was added drop-wise and the solution was then stirred for 15 minutes. The solvent was evaporated under reduced pressure and the reaction mixture was extracted with ethyl acetate (250 mL), washed with brine (2×100 mL), dried with $Na_2SO_4$, filtered and concentrated. The resulting solid was triturated with diethyl ether (150 mL) to afford 4-chloro-7-(phenylsulfonyl)-7H-pyrrolo[2,3-d]pyrimidine as an off-white solid (17.09 g, 89% yield).

Step 2. Preparation of 6-bromo-4-chloro-7-(phenylsulfonyl)-7H-pyrrolo[2,3-d]pyrimidine

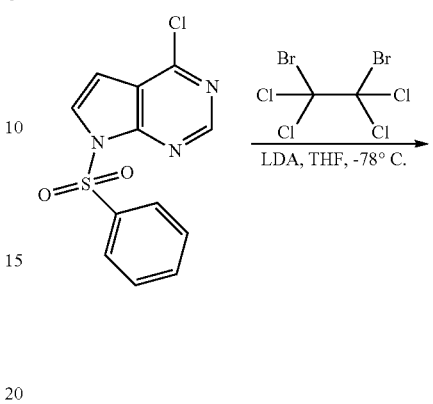

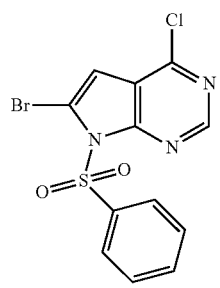

A solution of 1.6 M LDA in hexane (58 mL, 0.106 mol) was added drop-wise to a solution of 4-chloro-7-(phenylsulfonyl)-7H-pyrrolo[2,3-d]pyrimidine (15.65 g, 0.053 mol) in THF (250 mL) at −78° C. under $N_2$. After 30 minutes, a solution of 1,2-dibromotetrachloroethane (34.74 g, 0.107 mol) in THF (80 mL) was added drop-wise at −78° C. After 3 hours at −78° C., the reaction was warmed to room temperature over 1 hour. The reaction was cooled to −78° C. again, and then quenched with $H_2O$ (100 mL). The mixture was extracted with ethyl acetate (3×100 mL), dried over $Na_2SO_4$, filtered, concentrated to dryness. The product was purified by silica gel chromatography with hexane/ethyl acetate to afford the product (12.81 g, 65% yield) as an off-white solid.

Step 3. Preparation of tert-butyl 4-(6-bromo-7-(phenylsulfonyl)-7H-pyrrolo[2,3-d]pyrimidin-4-yl)piperazine-1-carboxylate

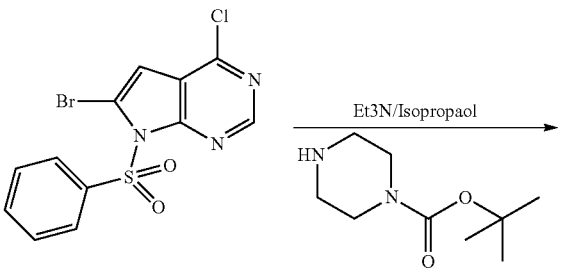

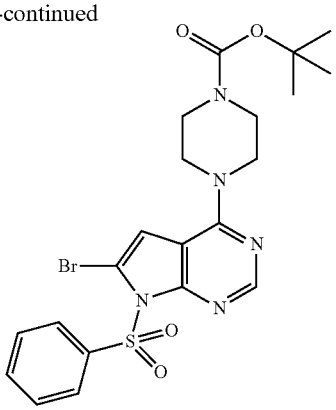

A mixture of 6-bromo-4-chloro-7-(phenylsulfonyl)-7H-pyrrolo[2,3-d]pyrimidine (372 mg, 0.1 mmol), tert-butyl piperazine-1-carboxylate (186 mg, 0.1 mmol) and triethylamine (150 mg, 1.5 mmol) in 10 mL isopropyl alcohol was heated to 100° C. overnight. The reaction mixture was cooled to room temp and the volatile material was removed by evaporation under reduced pressure. The residue was flash chromatographed on silica gel with solvent hexanes/ethyl acetate (0-80% gradient) to afford the product tert-butyl 4-(6-bromo-7-(phenylsulfonyl)-7H-pyrrolo[2,3-d]pyrimidin-4-yl)piperazine-1-carboxylate as a form of solid (64%). MS (+) ES: 522 (M+H)+.

Step 4. Preparation of tert-butyl 4-(6-(3-phenoxy-prop-1-yn-1-yl)-7-(phenylsulfonyl)-7H-pyrrolo[2,3-d]pyrimidin-4-yl)piperazine-1-carboxylate

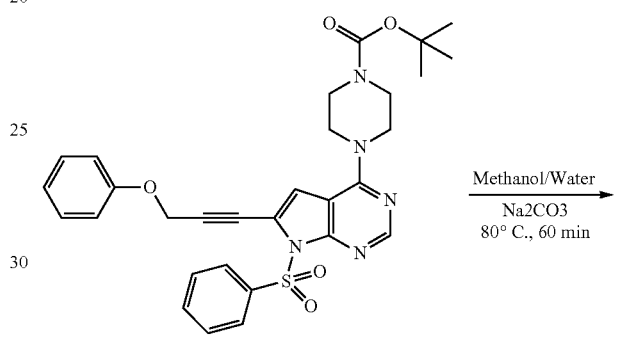

A mixture of tert-butyl 4-(6-bromo-7-(phenylsulfonyl)-7H-pyrrolo[2,3-d]pyrimidin-4-yl)piperazine-1-carboxylate (104 mg, 0.2 mmol), (prop-2-yn-1-yloxy)benzene (MW: 132.16, 132 mg, 1 mmol) and CuI (20 mg) in DMF (3 mL) was degassed before Pd(PPh$_3$)$_2$Cl$_2$ (10 mg, 10%) and triethylamine (0.2 mL) were added. The mixture was sealed and heated under nitrogen to 100° C. overnight. The reaction mixture was cooled to room temperature and partitioned between ethyl acetate (2 mL) and water 6 mL. The organic phase was separated and dried over MgSO$_4$. Evaporation of the solvent to leave a gummy solid that was loaded onto a silica column, eluted with hexanes/ethyl acetate (0 to 80% gradient to afford the product as an off-white solid (60 mg, 53% yield), MS (+) ES: 574 (M+H)+.

Step 5. Preparation of tert-butyl 4-(6-(3-phenoxy-prop-1-yn-1-yl)-7H-pyrrolo[2,3-d]pyrimidin-4-yl)piperazine-1-carboxylate

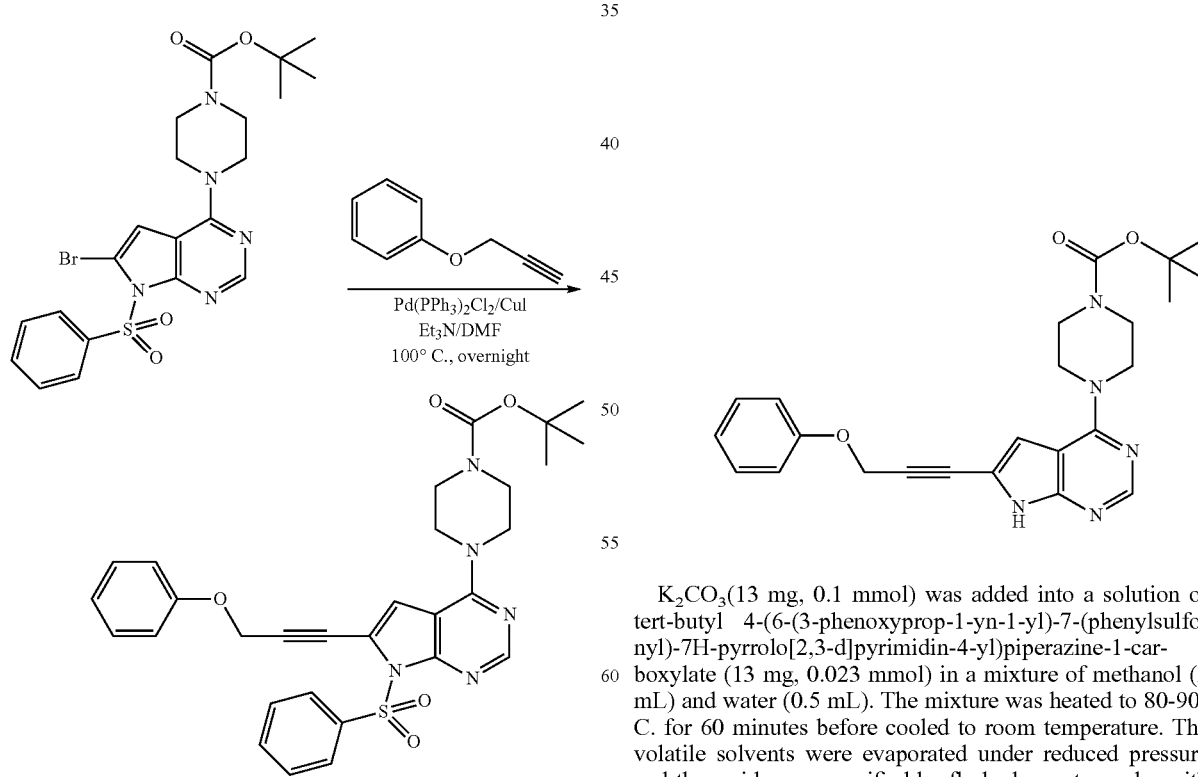

K$_2$CO$_3$ (13 mg, 0.1 mmol) was added into a solution of tert-butyl 4-(6-(3-phenoxyprop-1-yn-1-yl)-7-(phenylsulfonyl)-7H-pyrrolo[2,3-d]pyrimidin-4-yl)piperazine-1-carboxylate (13 mg, 0.023 mmol) in a mixture of methanol (2 mL) and water (0.5 mL). The mixture was heated to 80-90° C. for 60 minutes before cooled to room temperature. The volatile solvents were evaporated under reduced pressure and the residue was purified by flash chromatography with hexane/ethyl acetate (containing 10% 2N ammonia in methanol) to afford the product as a white solid (7 mg, 70% yield), MS (+) ES: 434 (M+H)+.

Step 6. Preparation of 6-(3-phenoxyprop-1-yn-1-yl)-4-(piperazin-1-yl)-7H-pyrrolo[2,3-d]pyrimidine

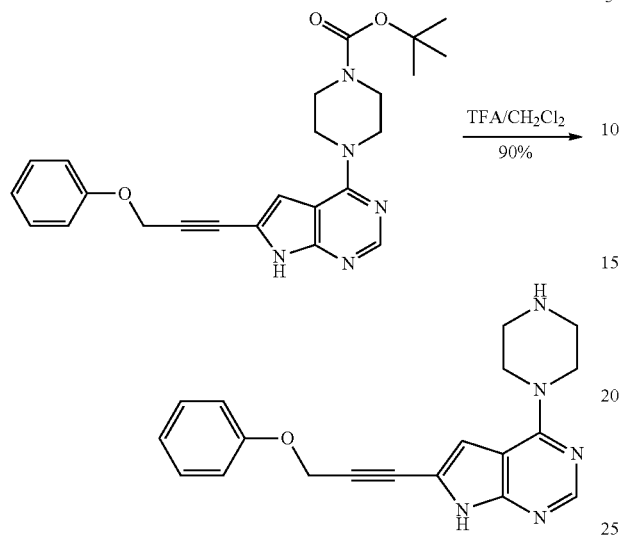

TFA (0.2 mL) was added into a solution of tert-butyl 4-(6-(3-phenoxyprop-1-yn-1-yl)-7H-pyrrolo[2,3-d]pyrimidin-4-yl)piperazine-1-carboxylate (43 mg, 0.1 mmol) in methelene chloride (0.5 mL). The solution was stirred for 30 minutes. The volatile solvents were evaporated to dryness under vacuum to afford the tan solid. This product was pure enough for the next step (30 mg, 90%), MS (+) ES: 334 (M+H)$^+$.

Step 7. Preparation of 1-(4-(6-(3-phenoxyprop-1-yn-1-yl)-7H-pyrrolo[2,3-d]pyrimidin-4-yl)piperazin-1-yl)prop-2-en-1-one

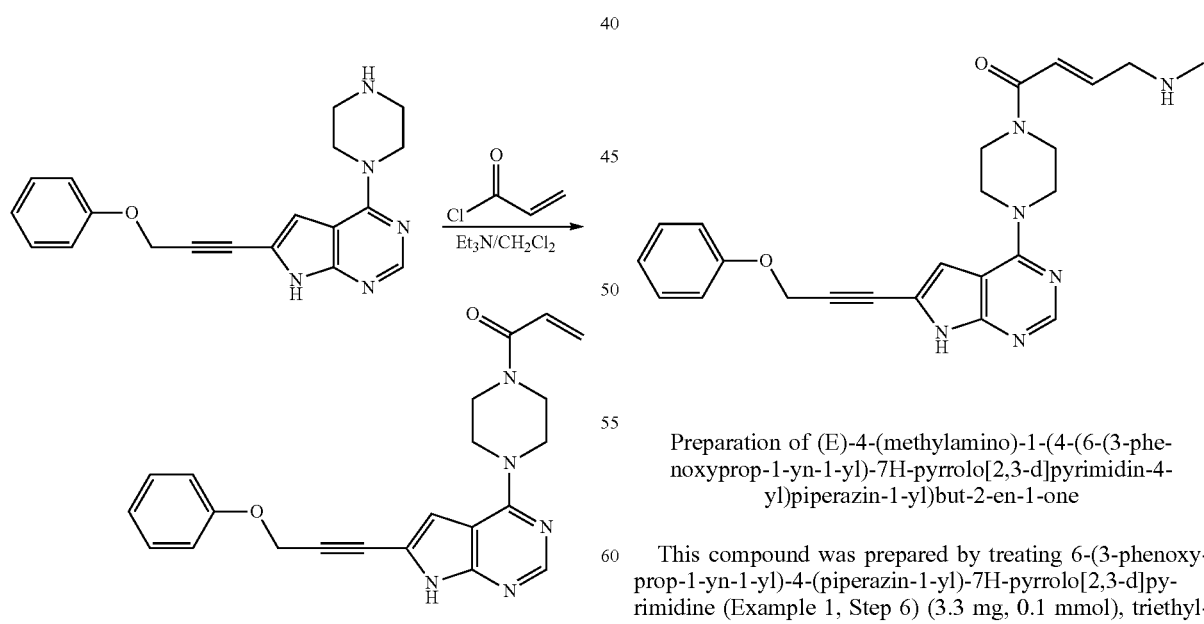

Methyl acryl chloride (0.9 mg, 0.1 mmol) was added in to a solution of 6-(3-phenoxyprop-1-yn-1-yl)-4-(piperazin-1-yl)-7H-pyrrolo[2,3-d]pyrimidine (3.3 mg, 0.1 mmol) and triethylamine (2 mg, 0.2 mmol) in anhydrous methelene chloride (0.3 mL) with stirring, stirred for 30 minutes. Solvent was evaporated and the product was purified by prep HPLC to afford a white solid (1.8 mg, 56% yield), MS (+) ES: 334 (M+H)$^+$.

Example 2

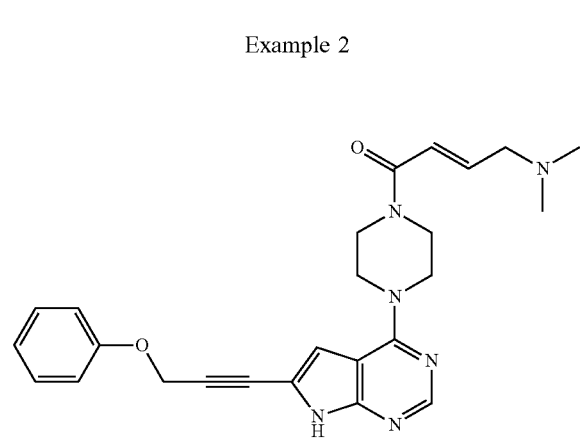

Preparation of (E)-4-(dimethylamino)-1-(4-(6-(3-phenoxyprop-1-yn-1-yl)-7H-pyrrolo[2,3-d]pyrimidin-4-yl)piperazin-1-yl)but-2-en-1-one This compound was prepared by treating 6-(3-phenoxyprop-1-yn-1-yl)-4-(piperazin-1-yl)-7H-pyrrolo[2,3-d]pyrimidine (Example 1, Step 6) (3.3 mg, 0.1 mmol), triethylamine (2 mg, 0.02 mmol) and (E)-4-(dimethylamino)but-2-enoic acid (1.4 mg, 0.012 mmol) in DMF (0.2 mL), by adding HBTU (4 mg, 0.01 mmol), stirred for 2 hours. This mixture was directly separated by HPLC to afford a white solid 2.4 mg (54%), MS (+) ES: 445 (M+H)$^+$.

Example 3

Preparation of (E)-4-(methylamino)-1-(4-(6-(3-phenoxyprop-1-yn-1-yl)-7H-pyrrolo[2,3-d]pyrimidin-4-yl)piperazin-1-yl)but-2-en-1-one This compound was prepared by treating 6-(3-phenoxyprop-1-yn-1-yl)-4-(piperazin-1-yl)-7H-pyrrolo[2,3-d]pyrimidine (Example 1, Step 6) (3.3 mg, 0.1 mmol), triethylamine (2 mg, 0.02 mmol) and (E)-4-(methylamino)but-2-enoic acid (1.4 mg, 0.012 mmol) in DMF (0.2 mL), by adding HBTU (4 mg, 0.01 mmol), stirred for 2 hours. This mixture was directly separated by HPLC to afford a white solid 2.4 mg (54%), MS (+) ES: 431 (M+H)$^+$.

Example 4

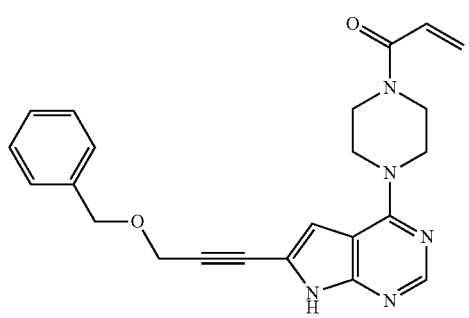 [SMILES: C=CC(=O)N1CCN(c2ncnc3[nH]c(C#CCOCc4ccccc4)cc23)CC1]

Preparation of 1-(4-(6-(3-(benzyloxy)prop-1-yn-1-yl)-7H-pyrrolo[2,3-d]pyrimidin-4-yl)piperazin-1-yl)prop-2-en-1-one This compound was prepared using the similar procedure of Example 1, except by ((prop-2-yn-1-yloxy)methyl)benzene to replace (prop-2-yn-1-yloxy)benzene in Step 4. The product was obtained following the same procedure of Step 5 to Step 7, purification by prep HPLC to afford a white solid, MS (+) ES: 402 (M+H)$^+$.

Example 5

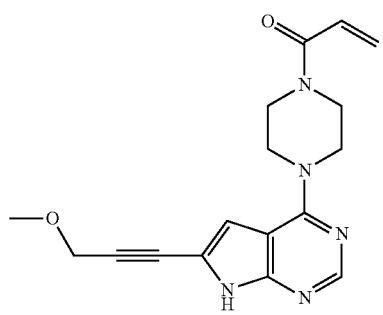 [SMILES: C=CC(=O)N1CCN(c2ncnc3[nH]c(C#CCOC)cc23)CC1]

Preparation of 1-(4-(6-(3-methoxyprop-1-yn-1-yl)-7H-pyrrolo[2,3-d]pyrimidin-4-yl)piperazin-1-yl)prop-2-en-1-one This compound was prepared through the similar procedure of Example 1, except by using 3-methoxyprop-1-yne to replace (prop-2-yn-1-yloxy)benzene in Step 4. The product was obtained following the same procedure of Step 5 to Step 7, purification by prep HPLC to afford a white solid, MS (+) ES: 326 (M+H)$^+$.

Reaction Scheme 2

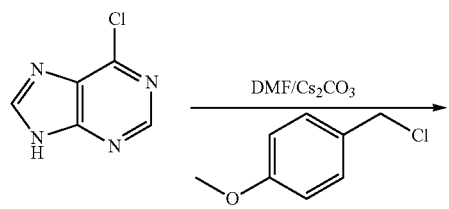

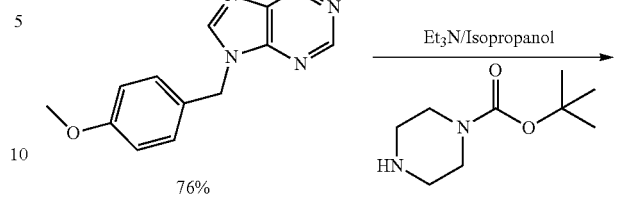

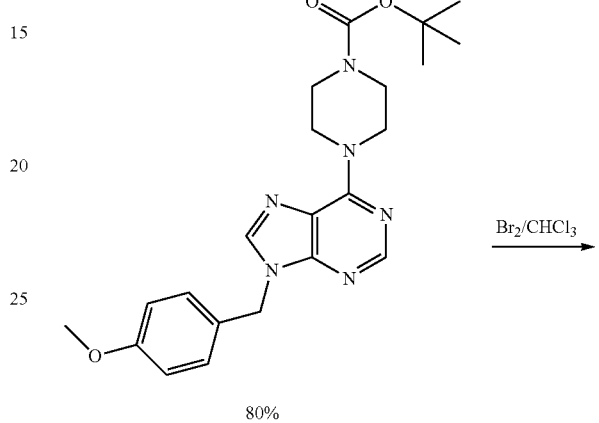

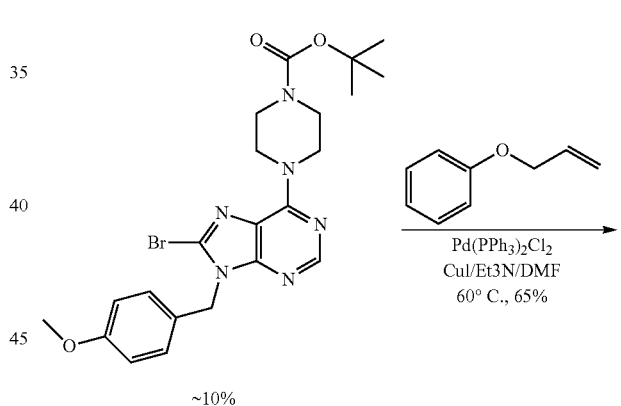

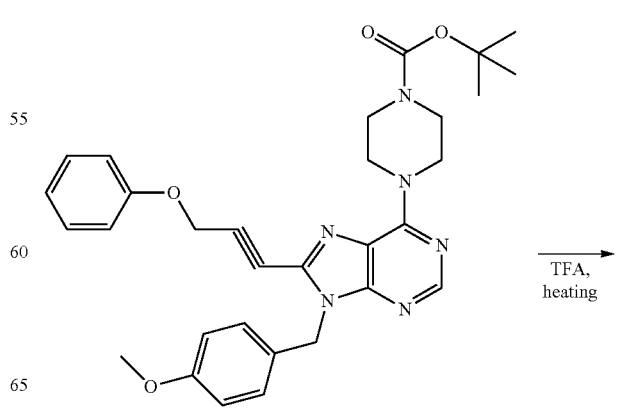

29
-continued

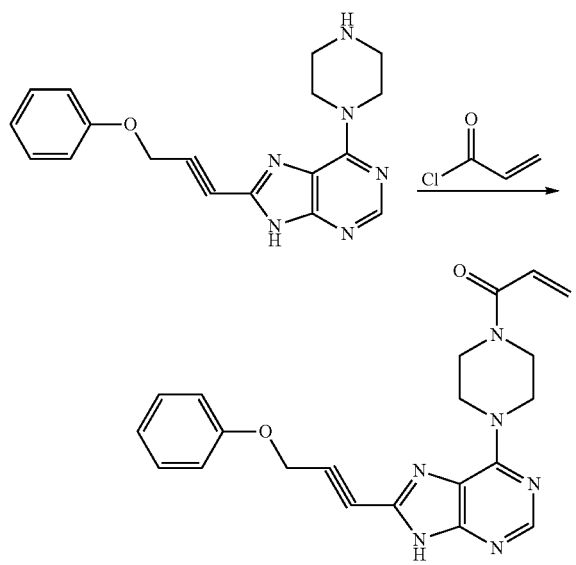

Example 6

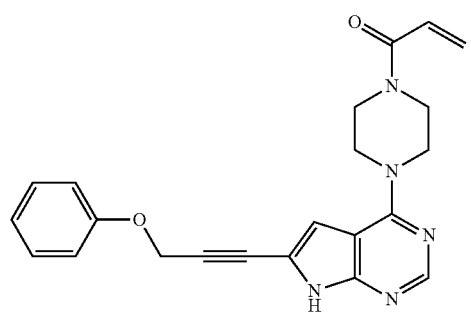 [SMILES: C=CC(=O)N1CCN(c2ncnc3[nH]c(C#CCOc4ccccc4)cc23)CC1]

Preparation of 1-(4-(8-(3-phenoxyprop-1-yn-1-yl)-9H-purin-6-yl)piperazin-1-yl)prop-2-en-1-one 30
Step 1. Preparation of 6-chloro-9-(4-methoxybenzyl)-9H-purine A mixture of 6-chloro-9H-purine (1.54 g, 1 mmol) and $K_2CO_3$ (5.0 g, 3 mmol) in 10 DMF was stirred for 30 minutes. p-Methoxybenzyl chloride (3.1 g, 2 mmol) was added at room temperature and the reaction mixture was stirred overnight. Partitioned between ether (20 mL) and water (50 mL), organic phase was separated and dried over $MgSO_4$. Product was purified by flash chromatography with hexane/ethyl acetate to afford the product as a white solid 1.9 g (70% yield), MS (+) ES: 275 (M+H)+.

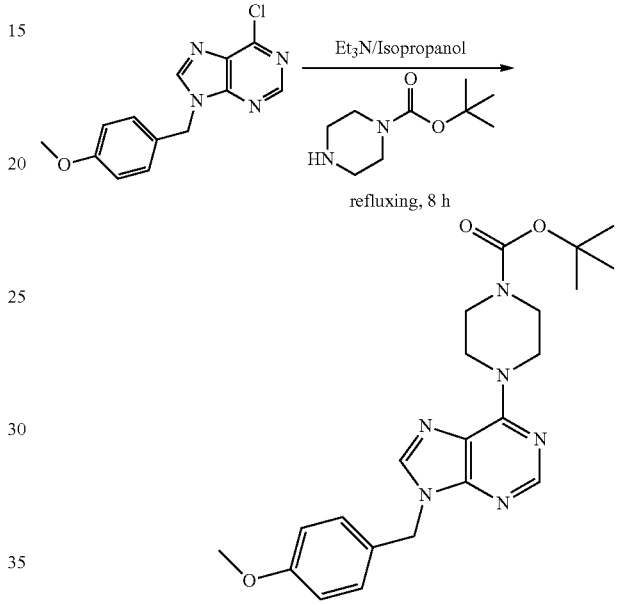

Step 2. Preparation of tert-butyl 4-(9-(4-methoxy-benzyl)-9H-purin-6-yl)piperazine-1-carboxylate A mixture of 6-chloro-9-(4-methoxybenzyl)-9H-purine (650 mg, 23.7 mmol), tert-butyl piperazine-1-carboxylate (442 mg, 23.7 mmol) and triethylamine (500 mg, 50 mmol) in isopropyl alcohol (10 mL) was heated to reflux for 4 hours. The mixture was cooled to room temperature and the volatile solvents were evaporated and the product was purified by flash chromatography with hexane/ethyl acetate to afford the product as a white solid 900 mg (90% yield), MS (+) ES: 425 (M+H)+.

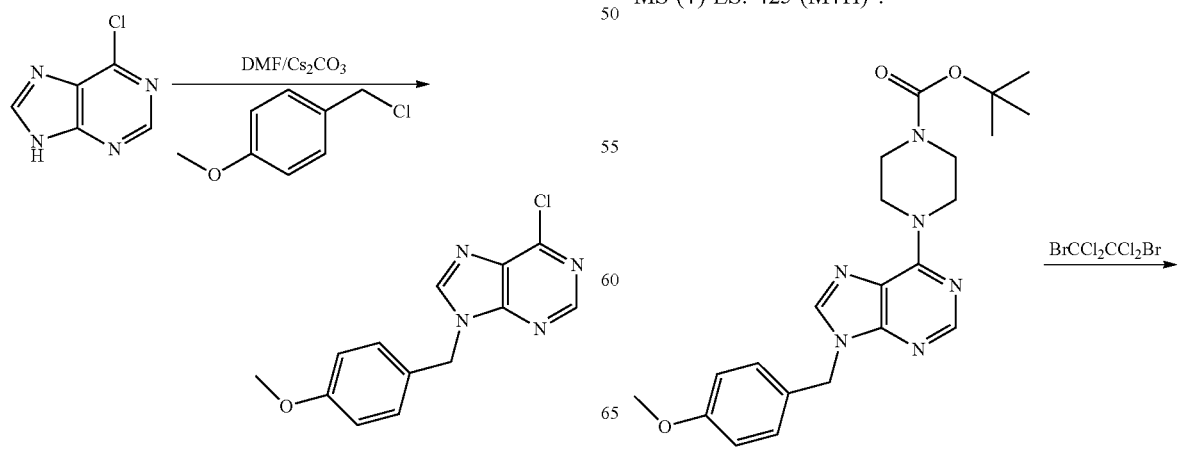

-continued

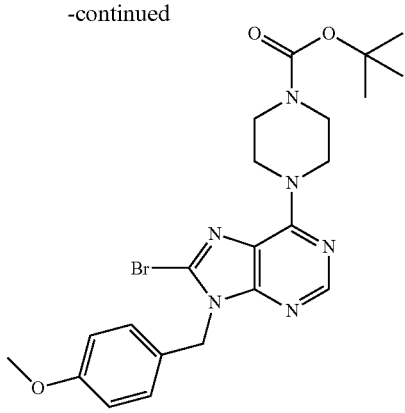

Step 3. Preparation of tert-butyl 4-(8-bromo-9-(4-methoxybenzyl)-9H-purin-6-yl)piperazine-1-carboxylate tert-butyl 4-(9-(4-methoxybenzyl)-9H-purin-6-yl)piperazine-1-carboxylate (424 mg, 1 mmol) was added into chloroform (10 mL), followed by NaOAc (148 mg, 1.8 mmol) at 00° C. with stirring. Bromine (240 mg, 1.5 mmol) was added dropwise over 30 minutes. The mixture then was allowed to warm-up to room temperature and stirred until the starting material had disappeared. The mixture was cooled again in an ice-water bath and treated with saturated NaHCO₃ and sat. sodium bisulfate solution, followed by stirring for 30 minutes. The organic phase was separated and dried over MgSO₄. Product was purified by flash chromatography with hexane/ethyl acetate top afford the product as a white solid 50 mg (10% yield), MS (+) ES: 504 (M+H)⁺.

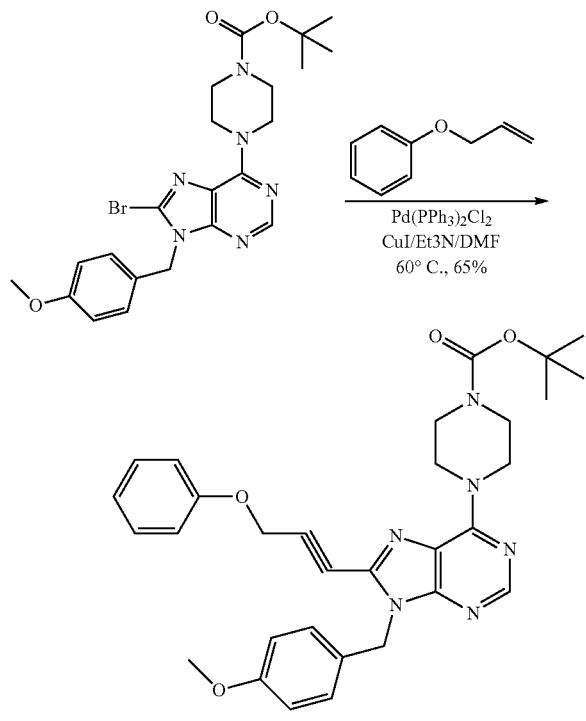

Step 4. Preparation of tert-butyl 4-(9-(4-methoxybenzyl)-8-(3-phenoxyprop-1-yn-1-yl)-9H-purin-6-yl)piperazine-1-carboxylate A mixture of tert-butyl 4-(6-bromo-7-(phenylsulfonyl)-7H-pyrrolo[2,3-d]pyrimidin-4-yl)piperazine-1-carboxylate (106 mg, 0.2 mmol), (prop-2-yn-1-yloxy)benzene (MW: 132.16, 132 mg, 1 mmol) and CuI (20 mg) in DMF (3 mL) was degassed before Pd(PPh₃)₂Cl₂ (10 mg, 10%) and triethylamine (0.2 mL) were added. The mixture was sealed and heated under nitrogen to 100° C. overnight. The reaction mixture was cooled to room temperature and partitioned between ethyl acetate (2 mL) and water 6 mL. The organic phase was separated and dried over MgSO₄. Evaporation of the solvent to leave a gummy solid that was loaded onto a silica column, eluted with hexanes/ethyl acetate (0 to 80% gradient to afford the product as an off-white solid (100 mg, 90% yield), MS (+) ES: 554 (M+H)⁺.

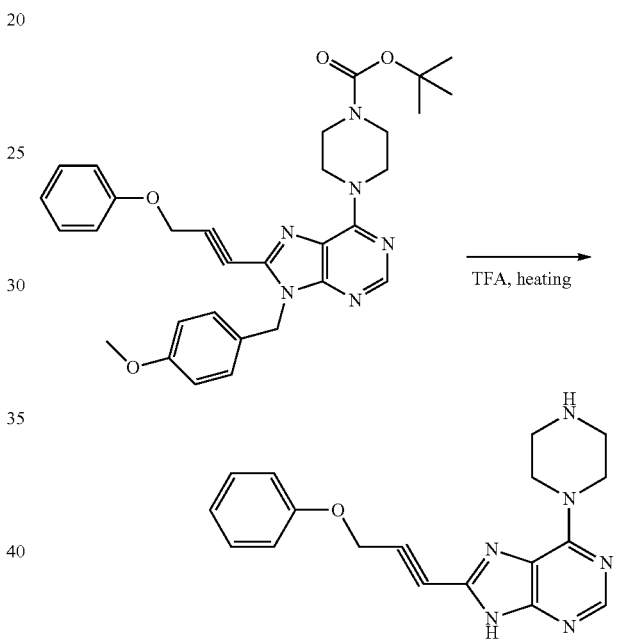

Step 5. Preparation of 8-(3-phenoxyprop-1-yn-1-yl)-6-(piperazin-1-yl)-9H-purine tert-Butyl 4-(8-bromo-9-(4-methoxybenzyl)-9H-purin-6-yl)piperazine-1-carboxylate (16 mg, 0.29 mmol) in TFA (0.2 mL) was heated to 70° C. for 2 h. It was then cooled to room temperature and TFA was evaporated to dryness under reduced pressure. The product was purified by prep HPLC to afford the product as a white solid 7.6 mg, yield 79%, MS (+) ES: 335 (M+H)⁺.

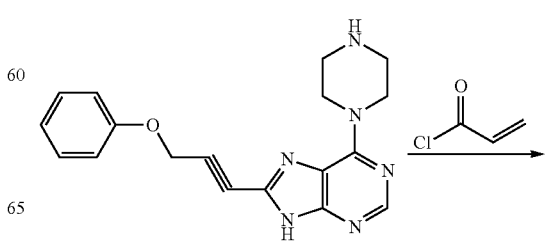

33
-continued

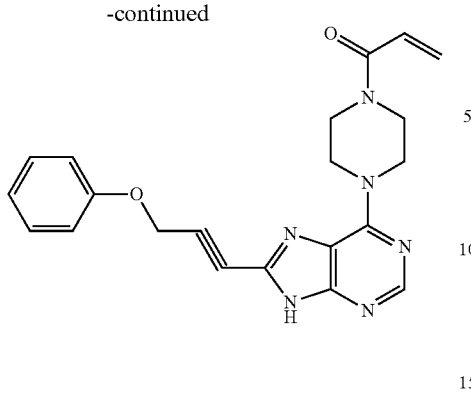

Step 6. Preparation of 1-(4-(8-(3-phenoxyprop-1-yn-1-yl)-9H-purin-6-yl)piperazin-1-yl)prop-2-en-1-one Methyl acryl chloride (1.8 mg, 0.2 mmol) was added in to a solution of 8-(3-phenoxyprop-1-yn-1-yl)-6-(piperazin-1-yl)-9H-purine (6.8 mg, 0.2 mmol) and triethylamine (6 mg, 0.6 mmol) in anhydrous methylene chloride (0.3 mL) with stirring. After the addition the reaction mixture was stirred for 30 minutes. Solvent was evaporated and the product was purified by prep HPLC to afford a white solid (4.0 mg, 58% yield), MS (+) ES: 389 (M+H)$^+$.

Example 7

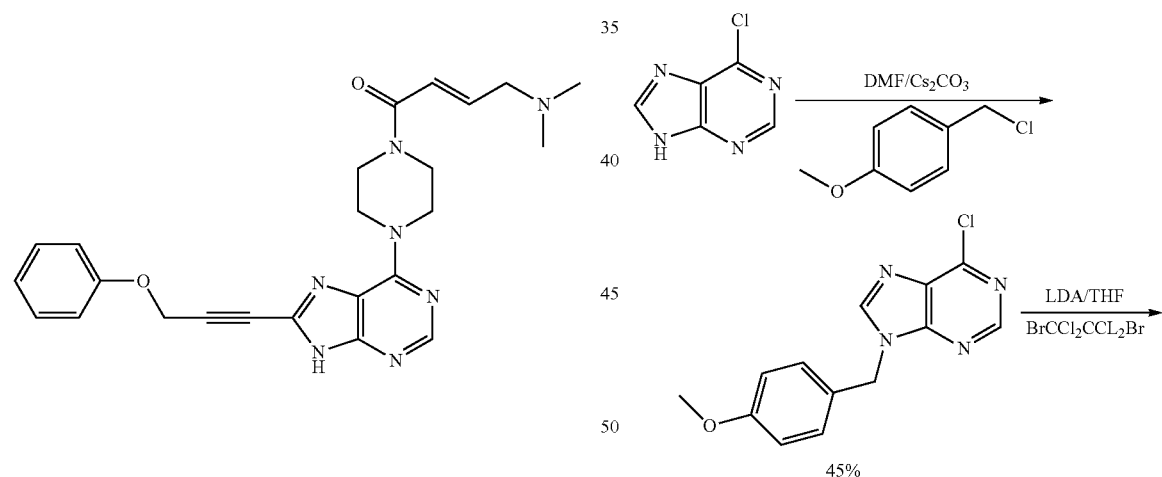

Preparation of (E)-4-(dimethylamino)-1-(4-(8-(3-phenoxyprop-1-yn-1-yl)-9H-purin-6-yl)piperazin-1-yl)but-2-en-1-one This compound was prepared by treating 8-(3-phenoxyprop-1-yn-1-yl)-6-(piperazin-1-yl)-9H-purine (Example 6, Step 5) (6.8 mg, 0.2 mmol), triethylamine (6 mg, 0.06 mmol) and (E)-4-(dimethylamino)but-2-enoic acid (3.3 mg, 0.04 mmol) in DMF (0.3 mL), by adding HBTU (8 mg, 0.02 mmol), stirred for 2 hours. This mixture was directly separated by HPLC to afford a white solid 5 mg (56%), MS (+) ES: 446 (M+H)$^+$.

34
Example 8

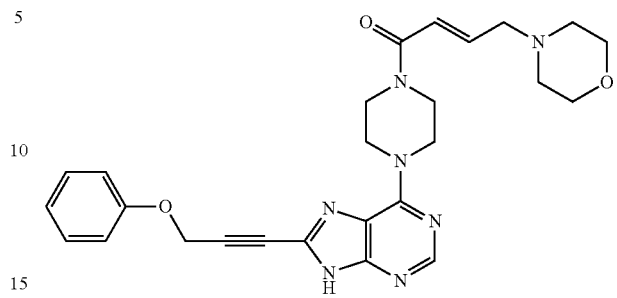

Preparation of (E)-4-morpholino-1-(4-(8-(3-phenoxyprop-1-yn-1-yl)-9H-purin-6-yl)piperazin-1-yl)but-2-en-1-one This compound was prepared by treating 8-(3-phenoxyprop-1-yn-1-yl)-6-(piperazin-1-yl)-9H-purine (Example 6, Step 5) (6.8 mg, 0.2 mmol), triethylamine (6 mg, 0.06 mmol) and (E)-4-morpholinobut-2-enoic acid (3.4 mg, 0.02 mmol) in DMF (0.3 mL), by adding HBTU (8 mg, 0.02 mmol), stirred for 2 hours. This mixture was directly separated by HPLC to afford a white solid, MS (+) ES: 488 (M+H)$^+$.

Reaction Scheme 3

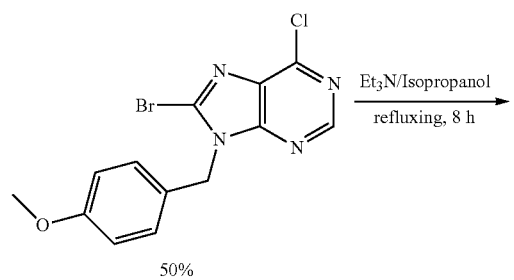

35
-continued

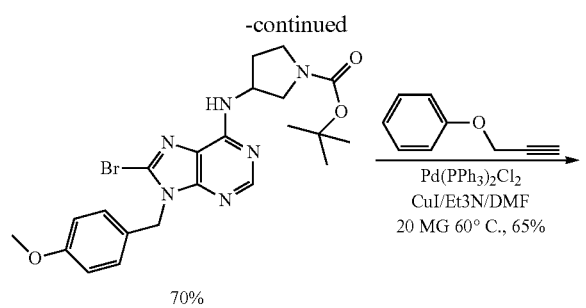

70%

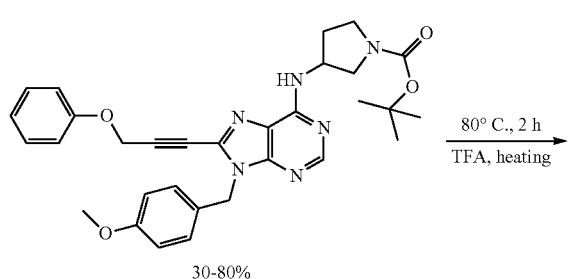

30-80%

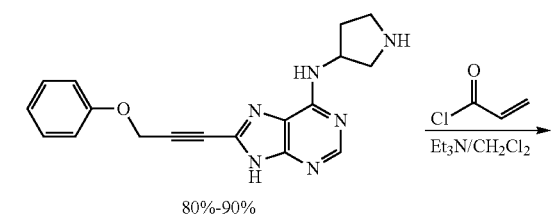

80%-90%

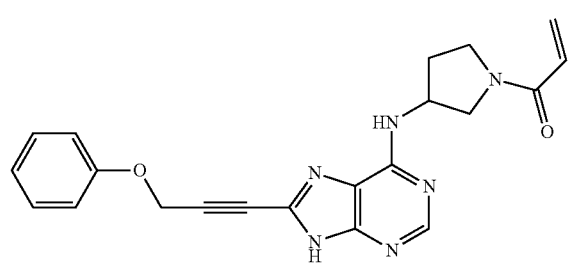 [SMILES: C=CC(=O)N1CCC(Nc2ncnc3[nH]c(C#CCOc4ccccc4)nc23)C1]

Example 9

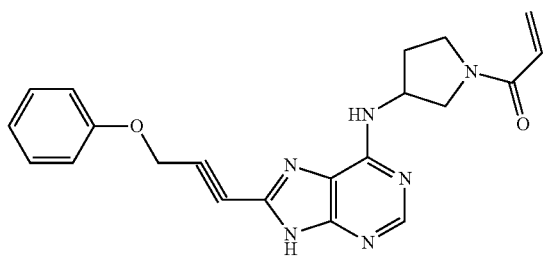 [SMILES: C=CC(=O)N1CCC(Nc2ncnc3[nH]c(C#CCOc4ccccc4)nc23)C1]

36

Preparation of 1-(3-((8-(3-phenoxyprop-1-yn-1-yl)-9H-purin-6-yl)amino)pyrrolidin-1-yl)prop-2-en-1-one

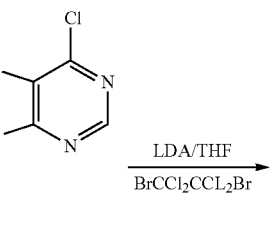

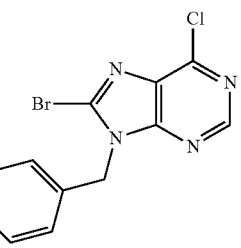

Step 1. Preparation of 8-bromo-6-chloro-9-(4-methoxybenzyl)-9H-purine

6-Chloro-9-(4-methoxyphenylmethyl)-9H-purine (272 mg, 0.99 mmol) in THF (4 mL) was added dropwise to a stirred solution of LDA [generated in situ from diisopropylamine (0.21 mL, 1.50 mmol) and n-BuLi (0.88 mL, 1.40 mmol, 1.6 M in hexane)] in THF (4 mL) at −78° C. under $N_2$. After stirring for 1 hour at −78° C., a solution of 1,2-dibromo-1,1,2,2,-tetrachloroethane (651 mg, 2.00 mmol) in THF (4 mL) was added dropwise and the resulting mixture was stirred at −78° C. for 5 hours, gradually warmed to ambient temperature over 2 hours and stirred at ambient temperature for 14 h. Sat. aq. $NH_4Cl$ (15 mL) was added and the mixture as extracted with EtOAc (2*25 mL). The combined organic extracts were washed with brine (20 mL), dried ($MgSO_4$) and evaporated in vacuo. The product was purified by flash chromatography on silica gel eluding with EtOAc-hexane to yield 280 mg (80%), MS (+) ES: 354 (M+H)$^+$.

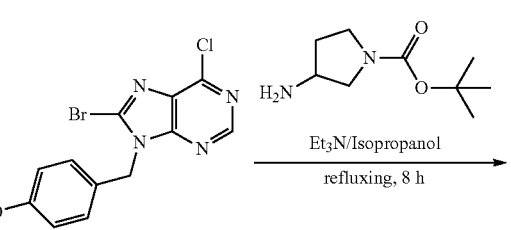

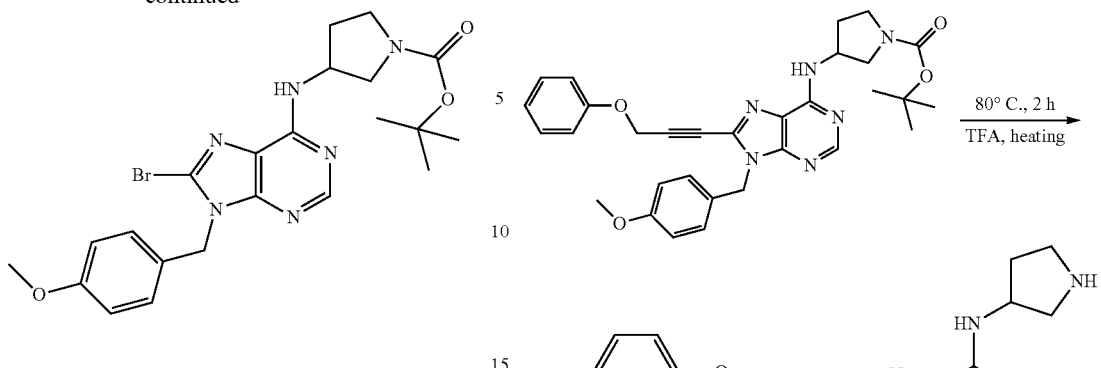

Step 2. Preparation of tert-butyl 3-((8-bromo-9-(4-methoxybenzyl)-9H-purin-6-yl)amino)pyrrolidine-1-carboxylate A mixture of 8-bromo-6-chloro-9-(4-methoxybenzyl)-9H-purine (353 mg, 1 mmol), tert-butyl 3-aminopyrrolidine-1-carboxylate (186 mg, 1 mmol) and triethylamine (150 mg, 1.5 mmol) in isopropyl alcohol (10 mL) was heated in a Microwave reactor to 120° C. for 3 hours. The mixture was cooled to room temperature and the volatile solvents were evaporated under reduced pressure to dryness. The product was purified by flash chromatography with hexanes/ethyl acetate to afford the product as a form white solid 318 mg, yield 63%, MS (+) ES: 503 (M+H)⁺.

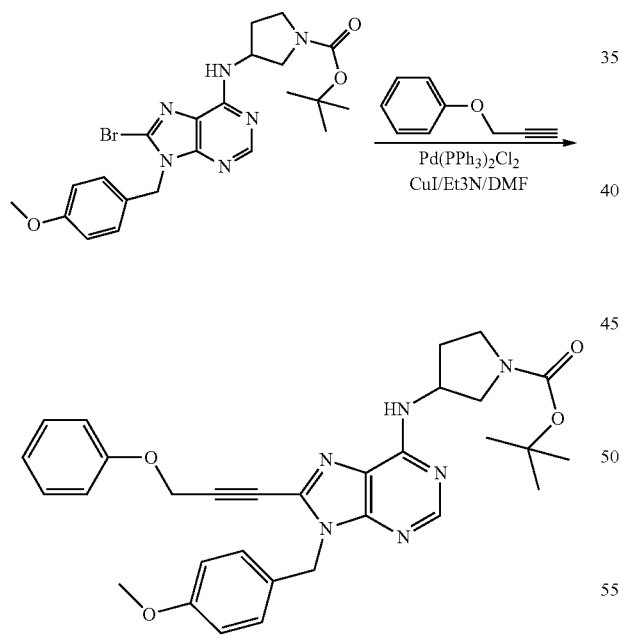

Step 3. Preparation of tert-butyl 3-((9-(4-methoxybenzyl)-8-(3-phenoxyprop-1-yn-1-yl)-9H-purin-6-yl)amino)pyrrolidine-1-carboxylate The title compound is prepared by using essentially the same procedure as in Example 1, Step 4 affording a solid product (60%), MS (+) ES: 555 (M+H)⁺.

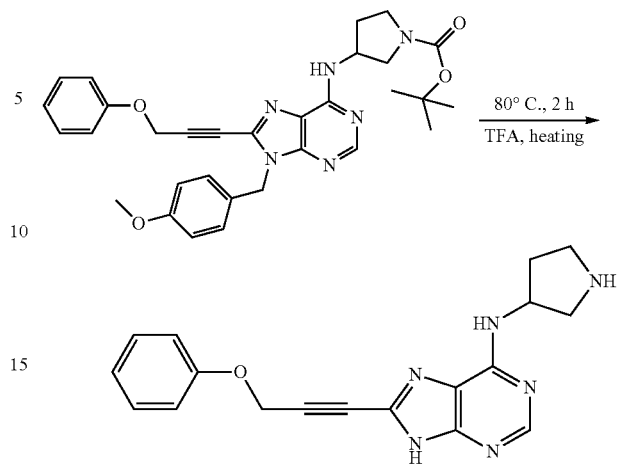

Step 4. Preparation of 8-(3-phenoxyprop-1-yn-1-yl)-N-(pyrrolidin-3-yl)-9H-purin-6-amine The title compound is prepared by using essentially the same procedure as in Example 1, Step 5 affording a solid product (89%), MS (+) ES: 335 (M+H)⁺.

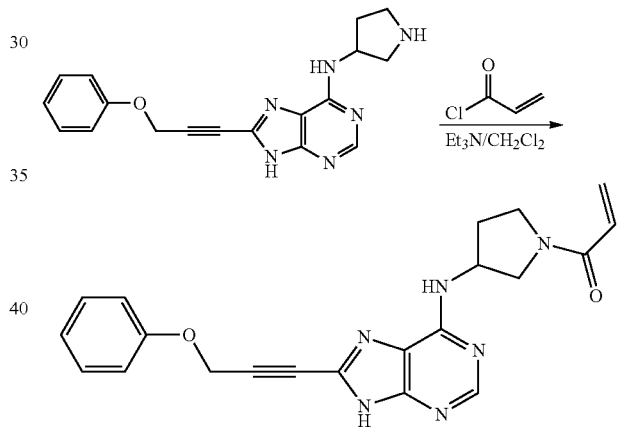

Step 5. Preparation of 1-(3-((8-(3-phenoxyprop-1-yn-1-yl)-9H-purin-6-yl)amino)pyrrolidin-1-yl)prop-2-en-1-one The title compound is prepared by using essentially the same procedure as in Example 1, Step 6 affording a solid product (56%), MS (+) ES: 389 (M+H)⁺.

Example 10

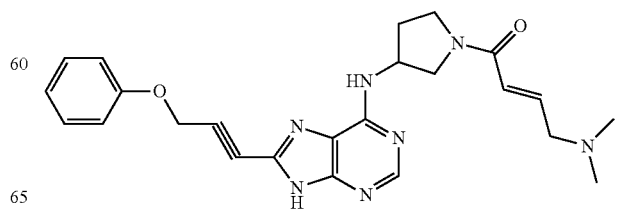

The title compound (E)-4-(dimethylamino)-1-(3-((8-(3-phenoxyprop-1-yn-1-yl)-9H-purin-6-yl)amino)pyrrolidin-1-yl)but-2-en-1-one was prepared by adding HBTU (8 mg, 0.02 mmol) into a mixture of 8-(3-phenoxyprop-1-yn-1-yl)-N-(pyrrolidin-3-yl)-9H-purin-6-amine (Example 9, Step 4) (6.7 mg, 0.2 mmol), triethylamine (6 mg, 0.06 mmol) and (E)-4-(dimethylamino)but-2-enoic acid (1.7 mg, 0.02 mmol) in DMF (0.3 mL), stirred for 2 hours. This mixture was directly separated by Prep HPLC to afford a white solid 5 mg (56%), MS (+) ES: 446 (M+H)⁺.

Example 11

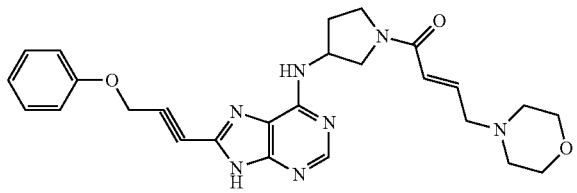 [SMILES: O=C(/C=C/CN1CCOCC1)N1CCC(Nc2ncnc3[nH]c(C#CCOc4ccccc4)nc23)C1]

The title compound (E)-4-morpholino-1-(3-((8-(3-phenoxyprop-1-yn-1-yl)-9H-purin-6-yl)amino)pyrrolidin-1-yl)but-2-en-1-one was prepared by using essentially the same procedure as in Example 10 by using (E)-4-morpholinobut-2-enoic acid instead of (E)-4-(dimethylamino)but-2-enoic acid affording a solid product (50%), MS (+) ES: 487 (M+H)⁺.

Example 12

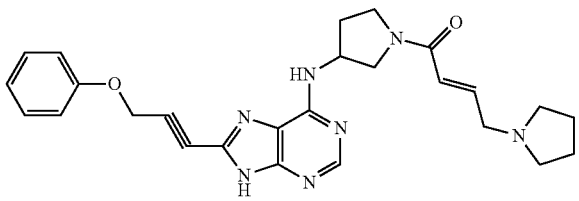 [SMILES: O=C(/C=C/CN1CCCC1)N1CCC(Nc2ncnc3[nH]c(C#CCOc4ccccc4)nc23)C1]

The title compound (E)-1-(3-((8-(3-phenoxyprop-1-yn-1-yl)-9H-purin-6-yl)amino)pyrrolidin-1-yl)-4-(pyrrolidin-1-yl)but-2-en-1-one was prepared by using essentially the same procedure as in Example 10 by using (E)-4-(pyrrolidin-1-yl)but-2-enoic acid instead of (E)-4 (dimethylamino)but-2-enoic acid affording a solid product, MS (+) ES: 472 (M+H)⁺.

Example 13

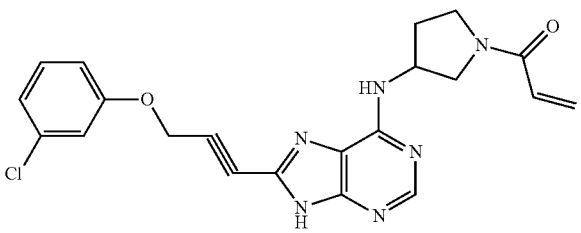 [SMILES: C=CC(=O)N1CCC(Nc2ncnc3[nH]c(C#CCOc4cccc(Cl)c4)nc23)C1]

The title compound 1-(3-((8-(3-(3-chlorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-chloro-3-(prop-2-yn-1-yloxy)benzene instead of (prop-2-yn-1-yloxy)benzene affording a solid product, MS (+) ES: 423 (M+H)⁺.

Example 14

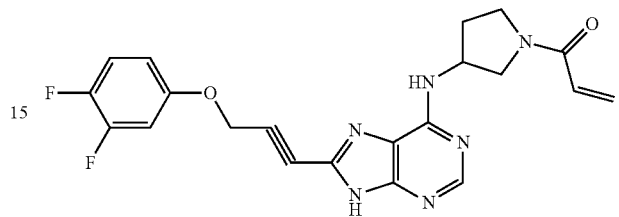

The title compound 1-(3-((8-(3-(3,4-difluoro phenoxy)prop-1-yn-1-yl)-9H-purin-6-yl)amino)pyrrolidin-1-yl)prop-2-en-1-one was prepared by using essentially the same procedure as in Example 9 except in the Step 3 by using 1,2-difluoro-4-(prop-2-yn-1-yloxy)benzene (prepared by 3,4-difluorophenol and 3-bromoprop-1-yne using the following reference procedure, Bomben, Andrea; Marques, Carlos A.; Selva, Maurizio; Tundo, Pietro; Tetrahedron, 1995, vol. 51, #42 p. 11573-11580) instead of (prop-2-yn-1-yloxy)benzene affording a solid product, MS (+) ES: 425 (M+H)⁺.

Example 15

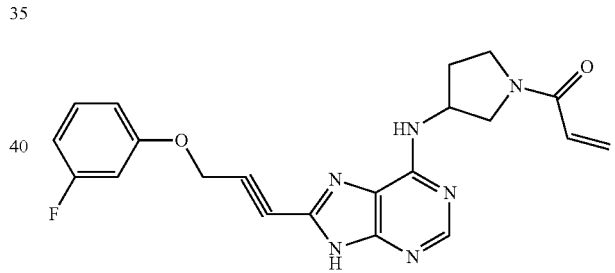

The title compound 1-(3-((8-(3-(3-fluorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-fluoro-3-(prop-2-yn-1-yloxy)benzene instead of (prop-2-yn-1-yloxy)benzene affording a solid product, MS (+) ES: 407 (M+H)⁺.

Example 16

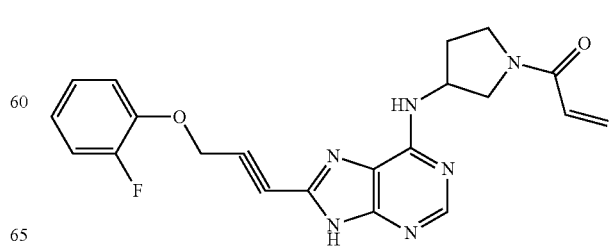

The title compound 1-(3-((8-(3-(2-fluorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-fluoro-2-(prop-2-yn-1-yloxy)benzene instead of (prop-2-yn-1-yloxy)benzene affording a solid product, MS (+) ES: 407 (M+H)⁺.

Example 17

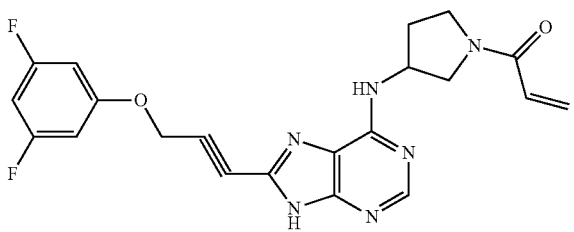 [SMILES: C=CC(=O)N1CCC(Nc2ncnc3[nH]c(C#CCOc4cc(F)cc(F)c4)nc23)C1]

The title compound 1-(3-((8-(3-(3,5-difluorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1,3-difluoro-5-(prop-2-yn-1-yloxy)benzene (prepared by 3,5-difluorophenol and 3-bromoprop-1-yne using the following reference procedure, Bomben, Andrea; Marques, Carlos A.; Selva, Maurizio; Tundo, Pietro; Tetrahedron, 1995, vol. 51, #42 p. 11573-11580) instead of (prop-2-yn-1-yloxy)benzene affording a solid product, MS (+) ES: 425 (M+H)⁺.

Example 18

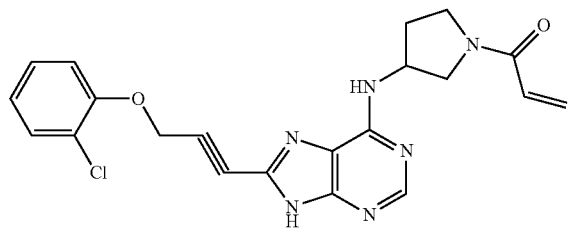 [SMILES: C=CC(=O)N1CCC(Nc2ncnc3[nH]c(C#CCOc4ccccc4Cl)nc23)C1]

The title compound 1-(3-((8-(3-(2-chlorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-chloro-2-(prop-2-yn-1-yloxy)benzene instead of (prop-2-yn-1-yloxy)benzene affording a solid product, MS (+) ES: 423 (M+H)⁺.

Example 19

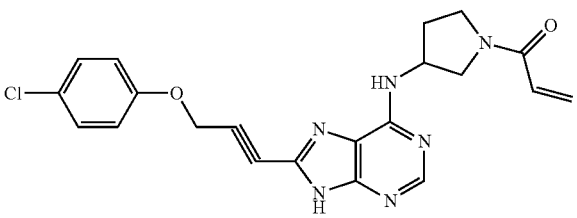 [SMILES: C=CC(=O)N1CCC(Nc2ncnc3[nH]c(C#CCOc4ccc(Cl)cc4)nc23)C1]

The title compound 1-(3-((8-(3-(4-chlorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-chloro-4-(prop-2-yn-1-yloxy)benzene instead of (prop-2-yn-1-yloxy)benzene affording a solid product, MS (+) ES: 423 (M+H)⁺.

Example 20

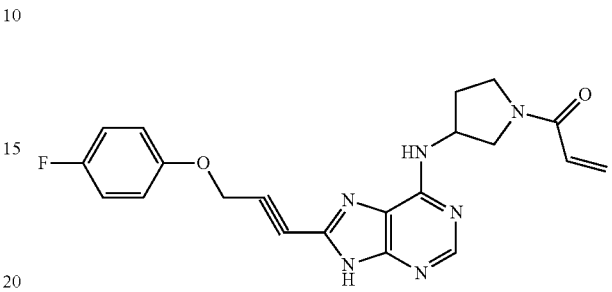

The title compound 1-(3-((8-(3-(4-fluorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-fluoro-4-(prop-2-yn-1-yloxy)benzene instead of (prop-2-yn-1-yloxy)benzene affording a solid product, MS (+) ES: 407 (M+H)⁺.

Example 21

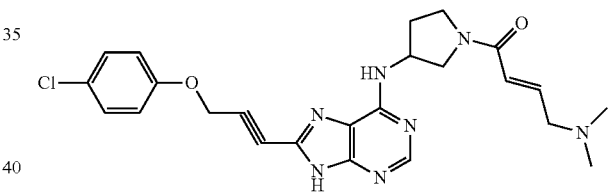

The title compound (E)-1-(3-((8-(3-(4-chlorophenoxy)prop-1-yn-1-yl)-9H-purin-6-yl)amino)pyrrolidin-1-yl)-4-(dimethylamino)but-2-en-1-one was prepared by using essentially the same procedure as in Example 10 affording a solid product (50%), MS (+) ES: 480 (M+H)⁺.

Example 22

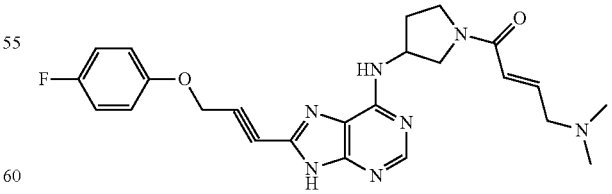

The title compound (E)-1-(3-((8-(3-(4-fluorophenoxy)prop-1-yn-1-yl)-9H-purin-6-yl)amino)pyrrolidin-1-yl)-4-(dimethylamino)but-2-en-1-one was prepared by using essentially the same procedure as in Example 10 affording a solid product, MS (+) ES: 464 (M+H)⁺.

Example 23

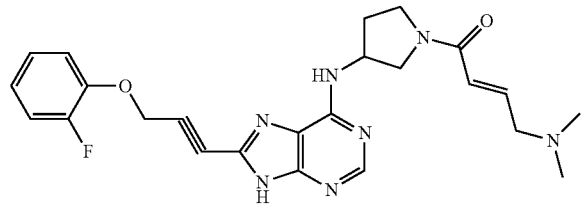 [SMILES: CN(C)C/C=C/C(=O)N1CCC(Nc2ncnc3[nH]c(C#CCOc4ccccc4F)nc23)C1]

The title compound (E)-1-(3-((8-(3-(2-fluorophenoxy)prop-1-yn-1-yl)-9H-purin-6-yl)amino)pyrrolidin-1-yl)-4-(dimethylamino)but-2-en-1-one was prepared by using essentially the same procedure as in Example 10 MS (+) ES: 464 (M+H)$^+$.

Example 24

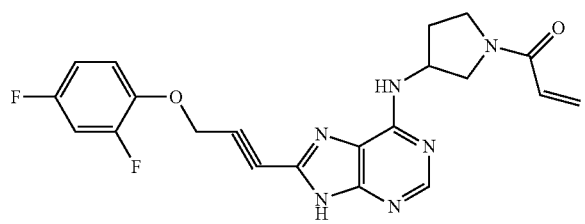 [SMILES: C=CC(=O)N1CCC(Nc2ncnc3[nH]c(C#CCOc4ccc(F)cc4F)nc23)C1]

The title compound 1-(3-((8-(3-(2,4-difluorophenoxy)prop-1-yn-1-yl)-9H-purin-6-yl)amino)pyrrolidin-1-yl)prop-2-en-1-one was prepared by using essentially the same procedure as in Example 9 except in the Step 3 by using 1,3-difluoro-4-(prop-2-yn-1-yloxy)benzene (prepared by 2,4-difluorophenol and 3-bromoprop-1-yne using the following reference procedure, Bomben, Andrea; Marques, Carlos A.; Selva, Maurizio; Tundo, Pietro; Tetrahedron, 1995, vol. 51, #42 p. 11573-11580) instead of (prop-2-yn-1-yloxy)benzene affording a solid product, MS (+) ES: 425 (M+H)$^+$.

Example 25

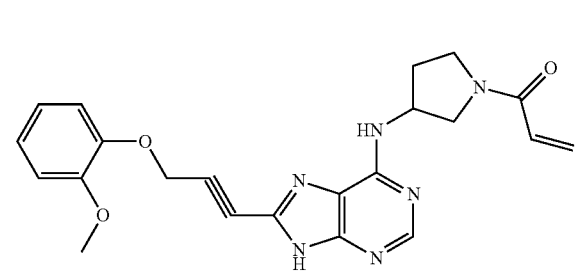 [SMILES: C=CC(=O)N1CCC(Nc2ncnc3[nH]c(C#CCOc4ccccc4OC)nc23)C1]

The title compound 1-(3-((8-(3-(2-methoxyphenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-methoxy-2-(prop-2-yn-1-yloxy)benzene instead of (prop-2-yn-1-yloxy)benzene affording a solid product, MS (+) ES: 419 (M+H)$^+$.

Example 26

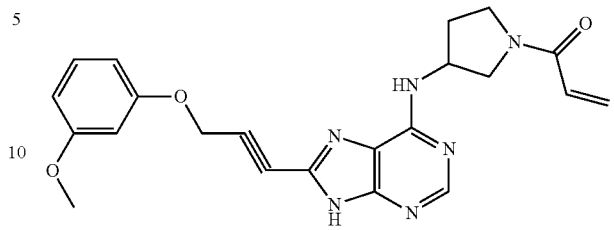

The title compound 1-(3-((8-(3-(3-methoxyphenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-methoxy-3-(prop-2-yn-1-yloxy)benzene instead of (prop-2-yn-1-yloxy)benzene affording a solid product, MS (+) ES: 419 (M+H)$^+$.

Example 27

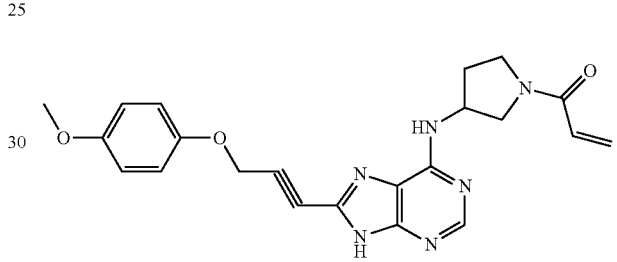

The title compound 1-(3-((8-(3-(4-methoxyphenoxy)prop-1-yn-1-yl)-9H-purin-6-yl)amino)pyrrolidin-1-yl)prop-2-en-1-one was prepared by using essentially the same procedure as in Example 9 except in the Step 3 by using 1-methoxy-4-(prop-2-yn-1-yloxy)benzene instead of (prop-2-yn-1-yloxy)benzene affording a solid product, MS (+) ES: 419 (M+H)$^+$.

Example 28

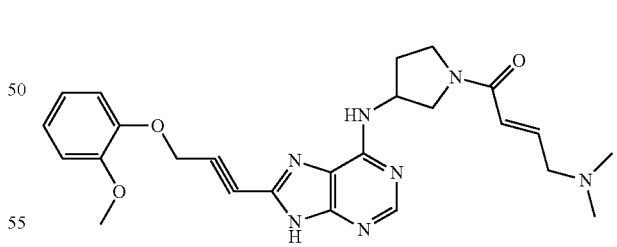

The title compound (E)-1-(3-((8-(3-(2-methoxyphenoxy)prop-1-yn-1-yl)-9H-purin-6-yl)amino)pyrrolidin-1-yl)-4-(dimethylamino)but-2-en-1-one was prepared by using essentially the same procedure as in Example 25 except in the last step by adding HBTU into a solution of the amine (8-(3-(2-methoxyphenoxy)prop-1-yn-1-yl)-N-(pyrrolidin-3-yl)-9H-purin-6-amine), triethylamine and (E)-4-(dimethylamino)but-2-enoic acid in DMF, stirred for 2 hours. This mixture was directly separated by Prep HPLC to afford a white solid product, MS (+) ES: 476 (M+H)$^+$.

Example 29

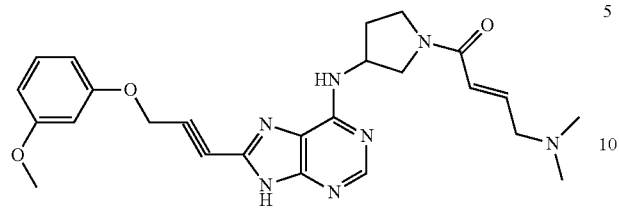

The title compound (E)-1-(3-((8-(3-(3-methoxyphenoxy)prop-1-yn-1-yl)-9H-purin-6-yl)amino)pyrrolidin-1-yl)-4-(dimethylamino)but-2-en-1-one was prepared by using essentially the same procedure as in Example 28 affording a solid product, MS (+) ES: 476 (M+H)$^+$.

Example 30

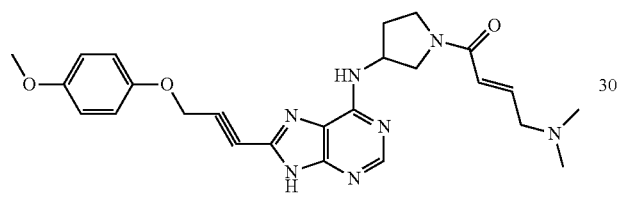

The title compound (E)-1-(3-((8-(3-(4-methoxyphenoxy)prop-1-yn-1-yl)-9H-purin-6-yl)amino)pyrrolidin-1-yl)-4-(dimethylamino)but-2-en-1-one was prepared by using essentially the same procedure as in Example 28 affording a solid product (50%), MS (+) ES: 476 (M+H)$^+$.

Example 31

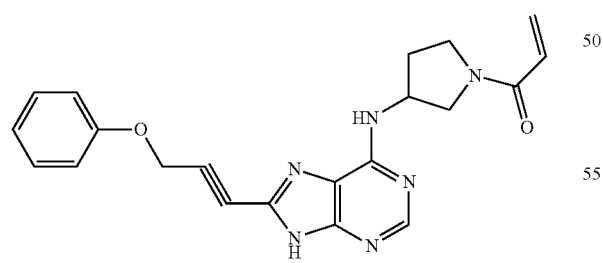

The title compound (R)-1-(3-((8-(3-phenoxyprop-1-yn-1-yl)-9H-purin-6-yl)amino)pyrrolidin-1-yl)prop-2-en-1-one was prepared by using essentially the same procedure as in Example 9 except in the Step 2 by using tert-butyl (R)-3-aminopyrrolidine-1-carboxylate instead of tert-butyl 3-aminopyrrolidine-1-carboxylate affording a solid product, MS (+) ES: 389 (M+H)$^+$.

Example 32

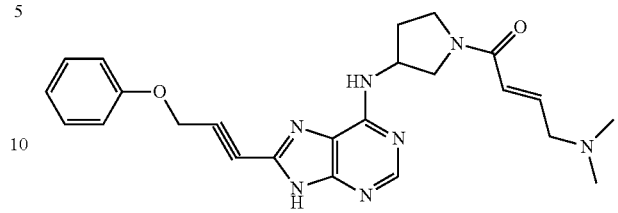

The title compound (R,E)-4-(dimethylamino)-1-(3-((8-(3-phenoxyprop-1-yn-1-yl)-9H-purin-6-yl)amino)pyrrolidin-1-yl)but-2-en-1-one was prepared by using essentially the same procedure as in Example 31 except in the last step by adding HBTU into a solution of the amine ((R)-8-(3-phenoxyprop-1-yn-1-yl)-N-(pyrrolidin-3-yl)-9H-purin-6-amine), triethylamine and (E)-4-(dimethylamino)but-2-enoic acid in DMF, stirred for 2 hours. This mixture was directly separated by Prep HPLC to afford a white solid product, MS (+) ES: 446 (M+H)$^+$.

Reaction Scheme 4

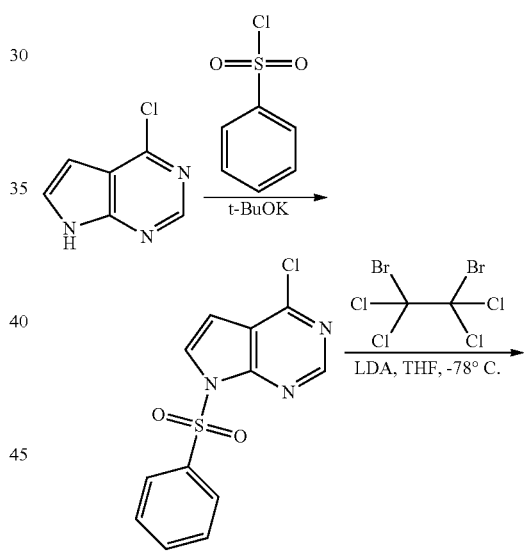

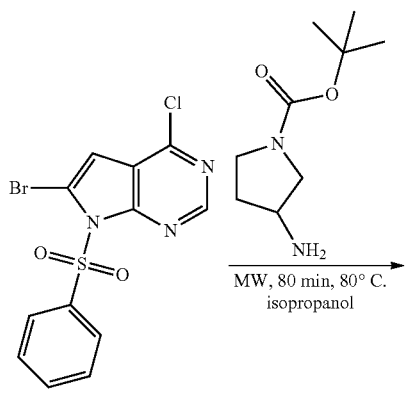

47

-continued

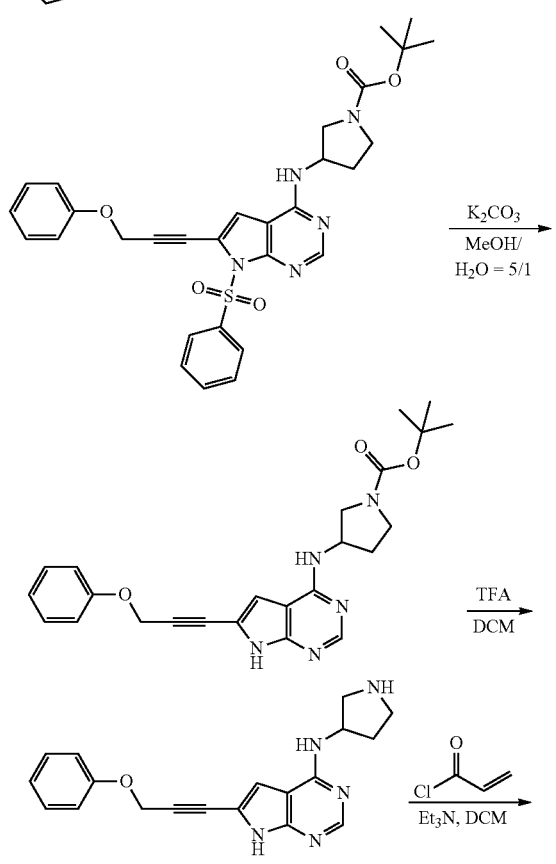

48

Example 33

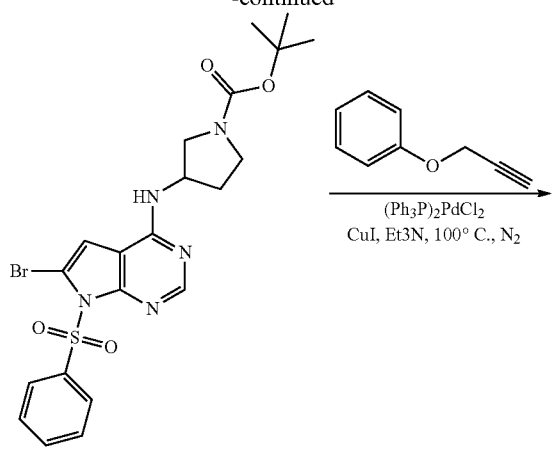

Preparation of 1-(3-((6-(3-phenoxyprop-1-yn-1-yl)-7H-pyrrolo[2,3-d]pyrimidin-4-yl)amino)pyrrolidin-1-yl)prop-2-en-1-one

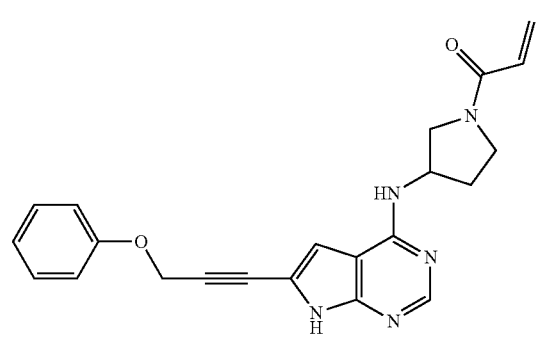

Step 1. Preparation of tert-butyl 3-((6-bromo-7-(phenylsulfonyl)-7H-pyrrolo[2,3-d]pyrimidin-4-yl)amino)pyrrolidine-1-carboxylate 6-Bromo-4-chloro-7-(phenylsulfonyl)-7H-pyrrolo[2,3-d]pyrimidine (1.50 g, 4.03 mmol) and tert-butyl 3-aminopyrrolidine-1-carboxylate (0.90 g, 4.83 mmol) in isopropanol (20 mL) was added triethylamine (0.61 g, 6.04 mmol). The mixture was sealed in a microwave reactor and heated at 150° C. for 100 minutes. Then it was cooled to room temperature and concentrated to dryness. The mixture was extracted with dichloromethane (10 mL) and the undissolved solid was filtered off. The solvent was evaporated and the product was purified by silica gel chromatography with solvents hexane/ethyl acetate (0 to 80%) to afford the product (0.63 g, 30% yield), MS (+) ES: 522 (M+H)+.

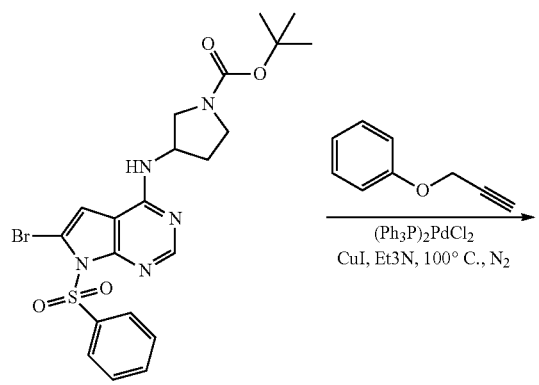
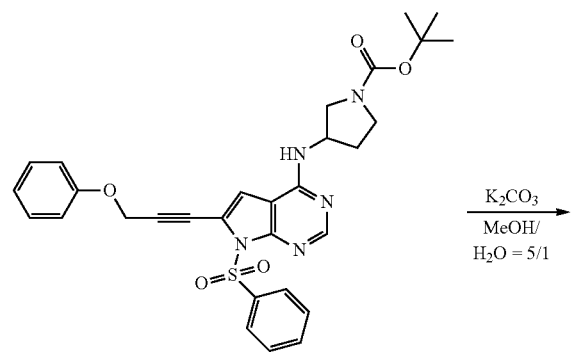

Step 3. Preparation of tert-butyl 3-((6-(3-phenoxy-prop-1-yn-1-yl)-7H-pyrrolo[2,3-d]pyrimidin-4-yl)amino)pyrrolidine-1-carboxylate A mixture of tert-butyl 3-((6-(3-phenoxyprop-1-yn-1-yl)-7-(phenylsulfonyl)-7H-pyrrolo[2,3-d]pyrimidin-4-yl)amino)pyrrolidine-1-carboxylate (0.178 g, 0.30 mmol) and potassium carbonate (0.166 g, 1.20 mmol) in a mixture of MeOH/H$_2$O=5/1 (20 mL) was stirred and heated at 70-80° C. for 3 hours. After cooling to room temp, the mixture was concentrated under reduced pressure to dryness. Saturated aqueous ammonium chloride solution (5 mL) was added. The mixture was extracted with dichloromethane (3×5 mL). The combined organic layer was dried with Na$_2$SO$_4$, filtered, concentrated to dryness. The product was purified by flash chromatography with hexane/ethyl acetate (10% 2N ammonia methanol solution) (0 to 80%) to afford the product as a white solid (0.80 g, ~60% yield), MS (+) ES: 434 (M+H)$^+$.

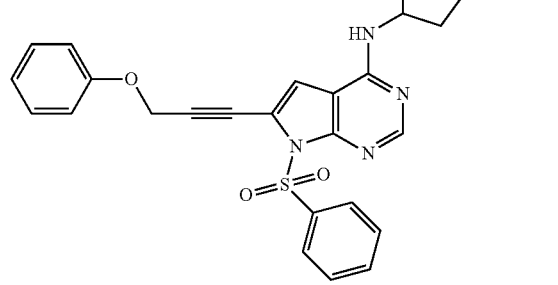

Step 2. Preparation of tert-butyl 3-((6-(3-phenoxy-prop-1-yn-1-yl)-7-(phenylsulfonyl)-7H-pyrrolo[2,3-d]pyrimidin-4-yl)amino)pyrrolidine-1-carboxylate To a solution of tert-butyl 3-((6-bromo-7-(phenylsulfonyl)-7H-pyrrolo[2,3-d]pyrimidin-4-yl)amino)pyrrolidine-1-carboxylate (0.300 g, 0.58 mmol) in DMF (5 mL) was added dichlorobis(triphenylphosphine)palladium(II) (0.036 g, 0.05 mmol), copper (I) iodide (0.020 g, 0.11 mmol), triethylamine (0.088 g, 0.87 mmol) and (prop-2-yn-1-yloxy)benzene (0.114 g, 0.87 mmol) under N$_2$. After the addition was completed, the reaction mixture was sealed and heated to 100° C. under nitrogen, stirred at 100° C. for 4 hours (LCMS check for completion). After cooling, H$_2$O (15 mL) was added and the mixture was extracted with ethyl acetate (3×5 mL), the combined organic layer was dried with Na$_2$SO$_4$, filtered through Celite, concentrated. The product was purified by silica gel chromatography with solvent hexane/ethyl acetate (0 to 100%) to afford the product as a white solid (0.198 g, 59% yield), MS (+) ES: 574 (M+H)$^+$.

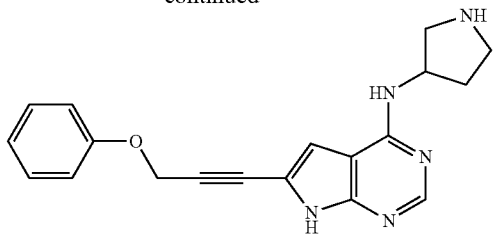

Step 4. Preparation of 6-(3-phenoxyprop-1-yn-1-yl)-N-(pyrrolidin-3-yl)-7H-pyrrolo[2,3-d]pyrimidin-4-amine The tert-butyl 3-((6-(3-phenoxyprop-1-yn-1-yl)-7H-pyrrolo[2,3-d]pyrimidin-4-yl)amino)pyrrolidine-1-carboxylate (0.100 mg, 0.22 mmol) was added to a mixed of dichloromethane (2 mL) and TFA (1.5 mL), stirred at room temperature for 30 minutes. The reaction mixture was concentrated under reduced pressure to dryness. This product was pure enough for the next step (the product can be purified by prep HPLC), to afford 6-(3-phenoxyprop-1-yn-1-yl)-N-(pyrrolidin-3-yl)-7H-pyrrolo[2,3-d]pyrimidin-4-amine As a white solid (0.069 g, 90% yield), MS (+) ES: 334 (M+H)⁺.

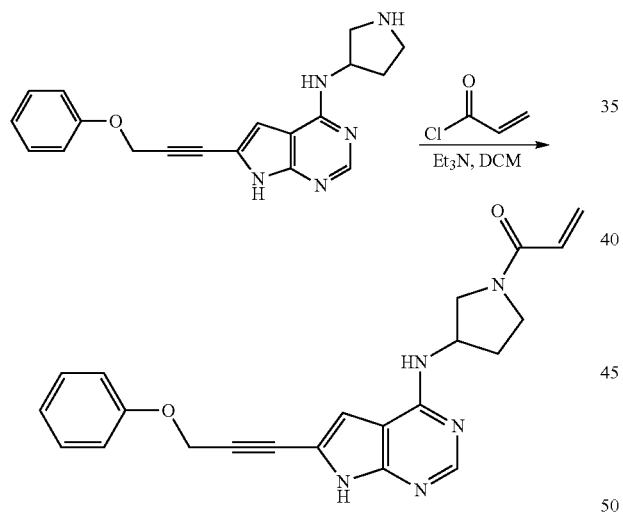

Step 5. Preparation of 1-(3-((6-(3-phenoxyprop-1-yn-1-yl)-7H-pyrrolo[2,3-d]pyrimidin-4-yl)amino)pyrrolidin-1-yl)prop-2-en-1-one To a solution of triethylamine (0.159 g, 1.57 mmol) and 6-(3-phenoxyprop-1-yn-1-yl)-N-(pyrrolidin-3-yl)-7H-pyrrolo[2,3-d]pyrimidin-4-amine (step 4) (0.069 g, 0.20 mmol) in anhydrous dichloromethane (0.5 mL) was added dropwise acryloyl chloride (0.018 g, 0.20 mmol) in 0.1 mL anhydrous dichloromethane at room temperature, stirred for 30 minutes. After completion of the reaction, methanol (0.5 mL) was added and stirred for a further 5 minutes. The mixture was concentrated under reduced pressure to dryness. This product was purified by flash chromatography with hexane/ethyl acetate (containing 10% 2N ammonia methanol solution) (0 to 80%) to afford the product as a white solid (0.059 g, 74% yield). This product can also be purified by prep HPLC, MS (+) ES: 388 (M+H)⁺.

Example 34

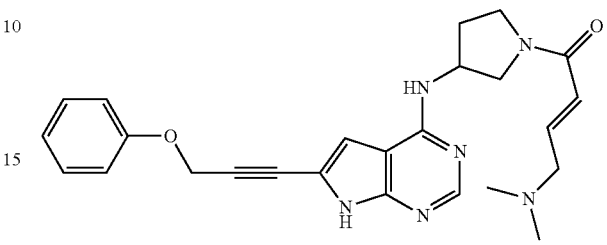

Preparation of (E)-4-(dimethylamino)-1-(3-((6-(3-phenoxyprop-1-yn-1-yl)-7H-pyrrolo[2,3-d]pyrimidin-4-yl)amino)pyrrolidin-1-yl)but-2-en-1-one The title compound (E)-4-(dimethylamino)-1-(3-((6-(3-phenoxyprop-1-yn-1-yl)-7H-pyrrolo[2,3-d]pyrimidin-4-yl)amino)pyrrolidin-1-yl)but-2-en-1-one is prepared by using essentially the same procedure as in Example 33 except in the last step by adding HBTU into a solution of the amine (step 4), triethylamine and (E)-4-(dimethylamino)but-2-enoic acid in DMF, stirred for 2 hours. This mixture was directly separated by Prep HPLC to afford a white solid product, MS (+) ES: 445 (M+H)⁺.

Example 35

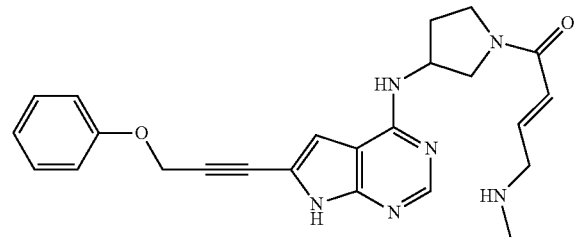 [SMILES: CNC/C=C/C(=O)N1CCC(Nc2ncnc3[nH]c(C#CCOc4ccccc4)cc23)C1]

Preparation of (E)-4-(dimethylamino)-1-(3-((6-(3-phenoxyprop-1-yn-1-yl)-7H-pyrrolo[2,3-d]pyrimidin-4-yl)amino)pyrrolidin-1-yl)but-2-en-1-one The title compound (E)-4-(dimethylamino)-1-(3-((6-(3-phenoxyprop-1-yn-1-yl)-7H-pyrrolo[2,3-d]pyrimidin-4-yl)amino)pyrrolidin-1-yl)but-2-en-1-one was prepared by using essentially the same procedure as in Example 34 except in the last step using (E)-4-(methylamino)but-2-enoic acid instead of (E)-4-(dimethylamino)but-2-enoic acid affording a solid product, MS (+) ES: 431 (M+H)⁺.

Example 36

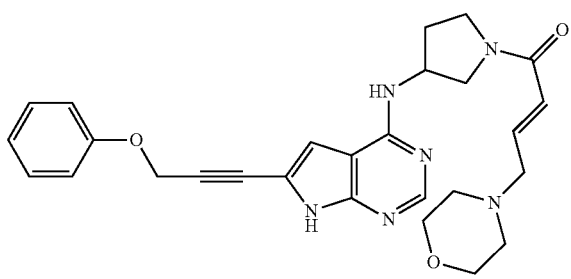 [SMILES: O=C(/C=C/CN1CCOCC1)N1CCC(Nc2ncnc3[nH]c(C#CCOc4ccccc4)cc23)C1]

Preparation of (E)-4-morpholino-1-(3-((6-(3-phenoxyprop-1-yn-1-yl)-7H-pyrrolo[2,3-d]pyrimidin-4-yl)amino)pyrrolidin-1-yl)but-2-en-1-one The title compound is prepared by using essentially the same procedure as in Example 34 except in the last step using (E)-4-morpholinobut-2-enoic acid instead of (E)-4-(dimethylamino)but-2-enoic acid affording a solid product, MS (+) ES: 487 (M+H)+.

Example 37

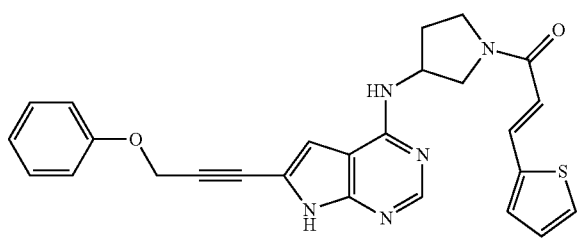 [SMILES: O=C(/C=C/c1cccs1)N1CCC(Nc2ncnc3[nH]c(C#CCOc4ccccc4)cc23)C1]

Preparation of (E)-1-(3-((6-(3-phenoxyprop-1-yn-1-yl)-7H-pyrrolo[2,3-d]pyrimidin-4-yl)amino)pyrrolidin-1-yl)-3-(thiophen-2-yl)prop-2-en-1-one The title compound was prepared by using essentially the same procedure as in Example 34 except in the last step using (E)-3-(thiophen-2-yl)acrylic acid in DMF instead of (E)-4-(dimethylamino)but-2-enoic acid affording a solid product, MS (+) ES: 470 (M+H)+.

Example 38

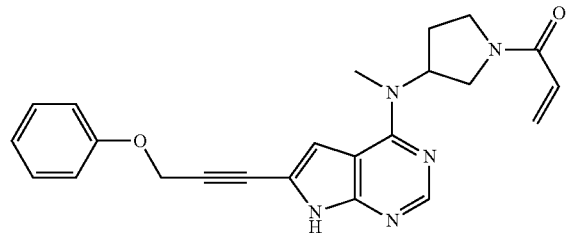 [SMILES: C=CC(=O)N1CCC(N(C)c2ncnc3[nH]c(C#CCOc4ccccc4)cc23)C1]

Preparation of 1-(3-(methyl(6-(3-phenoxyprop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 33 except in the first step using tert-butyl 3-(methylamino)pyrrolidine-1-carboxylate instead of the tert-butyl 3-aminopyrrolidine-1-carboxylate affording a solid product, MS (+) ES: 402 (M+H)+.

Example 39

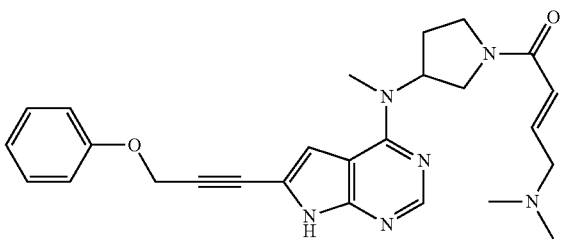 [SMILES: CN(C)C/C=C/C(=O)N1CCC(N(C)c2ncnc3[nH]c(C#CCOc4ccccc4)cc23)C1]

Preparation of (E)-4-(dimethylamino)-1-(3-(methyl (6-(3-phenoxyprop-1-yn-1-yl)-7H-pyrrolo[2,3-d] pyrimidin-4-yl)amino)pyrrolidin-1-yl)but-2-en-1-one The title compound was prepared by using essentially the same procedure as in Example 34 except in the first step using tert-butyl 3-(methylamino)pyrrolidine-1-carboxylate instead of the tert-butyl 3-aminopyrrolidine-1-carboxylate affording a solid product, MS (+) ES: 459 (M+H)+.

Example 40

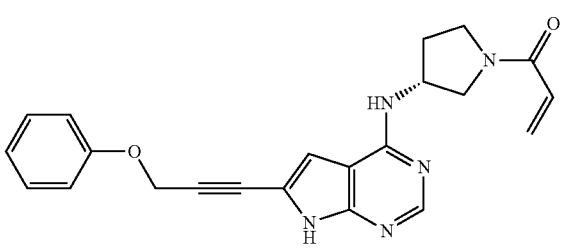

Preparation of (R)-1-(3-((6-(3-phenoxyprop-1-yn-1-yl)-7H-pyrrolo[2,3-d]pyrimidin-4-yl)amino)pyrrolidin-1-yl)prop-2-en-1-one The title compound is prepared by using essentially the same procedure as in Example 33 except in the first step using tert-butyl (R)-3-aminopyrrolidine-1-carboxylate instead of the tert-butyl 3-aminopyrrolidine-1-carboxylate affording a solid product, MS (+) ES: 388 (M+H)+.

Example 41

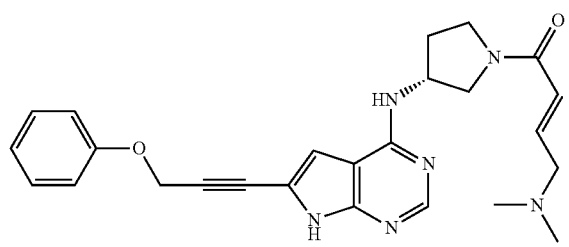 [SMILES: CN(C)C/C=C/C(=O)N1CC[C@@H](Nc2ncnc3[nH]c(C#CCOc4ccccc4)cc23)C1]

Preparation of (R,E)-4-(dimethylamino)-1-(3-((6-(3-phenoxyprop-1-yn-1-yl)-7H-pyrrolo[2,3-d]pyrimidin-4-yl)amino)pyrrolidin-1-yl)but-2-en-1-one The title compound (E)-4-(dimethylamino)-1-(3-((6-(3-phenoxyprop-1-yn-1-yl)-7H-pyrrolo[2,3-d]pyrimidin-4-yl)amino)pyrrolidin-1-yl)but-2-en-1-one was prepared by using essentially the same procedure as in Example 40 except in the last step by adding HBTU into a solution of the amine, triethylamine and (E)-4-(dimethylamino)but-2-enoic acid in DMF, stirred for 2 hours. This mixture was directly separated by Prep HPLC to afford a white solid product, MS (+) ES: 445 (M+H)$^+$.

Example 42

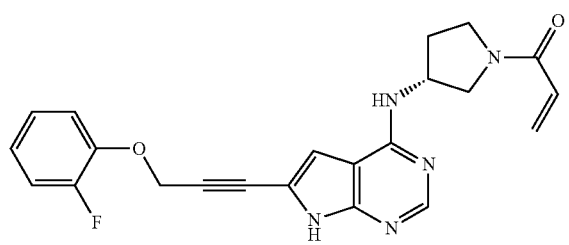 [SMILES: C=CC(=O)N1CC[C@@H](Nc2ncnc3[nH]c(C#CCOc4ccccc4F)cc23)C1]

Preparation of (R)-1-(3-((6-(3-(2-fluorophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 using 1-fluoro-2-(prop-2-yn-1-yloxy)benzene instead of the (prop-2-yn-1-yloxy)benzene affording a solid product, MS (+) ES: 406 (M+H)$^+$.

Example 43

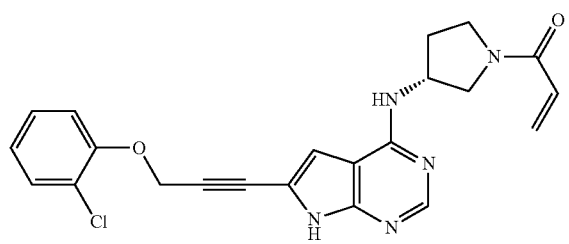 [SMILES: C=CC(=O)N1CC[C@@H](Nc2ncnc3[nH]c(C#CCOc4ccccc4Cl)cc23)C1]

Preparation of (R)-1-(3-((6-(3-(2-chlorophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 using 1-chloro-2-(prop-2-yn-1-yloxy)benzene instead of the (prop-2-yn-1-yloxy)benzene affording a solid product, MS (+) ES: 422 (M+H)$^+$.

Example 44

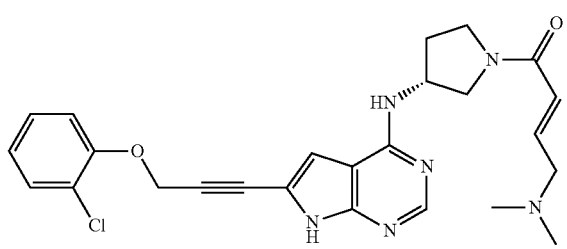

Preparation of (R,E)-1-(3-((6-(3-(2-chlorophenoxy)prop-1-yn-1-yl)-7H-pyrrolo[2,3-d]pyrimidin-4-yl)amino)pyrrolidin-1-yl)-4-(dimethylamino)but-2-en-1-one The title compound was prepared by using essentially the same procedure as in Example 43 except in the last step using acid and HBTU instead of the acyl chloride by adding HBTU into a solution of the amine, triethylamine and (E)-4-(dimethylamino)but-2-enoic acid in DMF, stirred for 2 hours. This mixture was directly separated by Prep HPLC to afford a solid product, MS (+) ES: 479 (M+H)$^+$.

Example 45

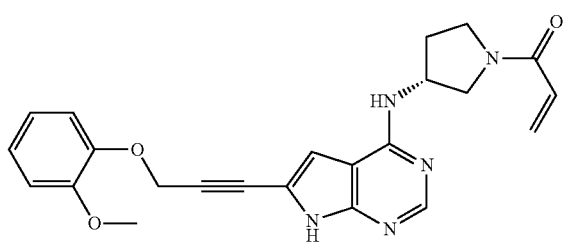

Preparation of (R)-1-(3-((6-(3-(2-methoxyphenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 using 1-methoxy-2-(prop-2-yn-1-yloxy)benzene instead of the (prop-2-yn-1-yloxy)benzene affording a solid product, MS (+) ES: 418 (M+H)$^+$.

Example 46

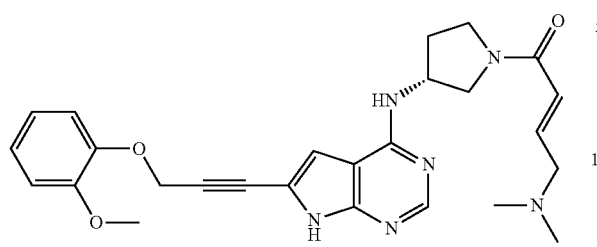

Preparation of (R,E)-1-(3-((6-(3-(2-methoxyphenoxy)prop-1-yn-1-yl)-7H-pyrrolo[2,3-d]pyrimidin-4-yl)amino)pyrrolidin-1-yl)-4-(dimethylamino)but-2-en-1-one The title compound was prepared by using essentially the same procedure as in Example 45 except in the last step using acid and HBTU instead of the acyl chloride by adding HBTU into a solution of the amine, triethylamine and (E)-4-(dimethylamino)but-2-enoic acid in DMF, stirred for 2 hours. This mixture was directly separated by Prep HPLC to afford a solid product, MS (+) ES: 475 (M+H)$^+$.

Example 47

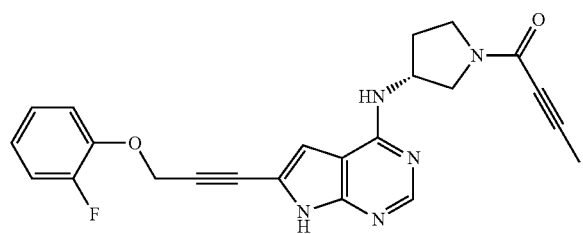 [SMILES: CC#CC(=O)N1CC[C@@H](Nc2ncnc3[nH]c(C#CCOc4ccccc4F)cc23)C1]

Preparation of (R)-1-(3-((6-(3-(2-fluorophenoxy)prop-1-yn-1-yl)-7H-pyrrolo[2,3-d]pyrimidin-4-yl)amino)pyrrolidin-1-yl)but-2-yn-1-one The title compound was prepared by using essentially the same procedure as in Example 42 except in the last step using but-2-ynoic acid and HBTU in DMF instead of the acyl chloride by adding HBTU into a solution of the amine, triethylamine and but-2-ynoic acid in DMF, stirred for 2 hours. This mixture was directly separated by Prep HPLC affording a solid product, MS (+) ES: 418 (M+H)$^+$.

Example 48

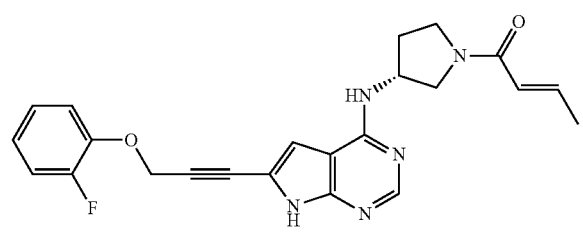 [SMILES: C/C=C/C(=O)N1CC[C@@H](Nc2ncnc3[nH]c(C#CCOc4ccccc4F)cc23)C1]

Preparation of (R,E)-1-(3-((6-(3-(2-fluorophenoxy)prop-1-yn-1-yl)-7H-pyrrolo[2,3-d]pyrimidin-4-yl)amino)pyrrolidin-1-yl)but-2-en-1-one The title compound was prepared by using essentially the same procedure as in Example 43 except in the last step using (E)-but-2-enoyl chloride instead of the acryloyl chloride affording a solid product, MS (+) ES: 420 (M+H)$^+$.

Example 49

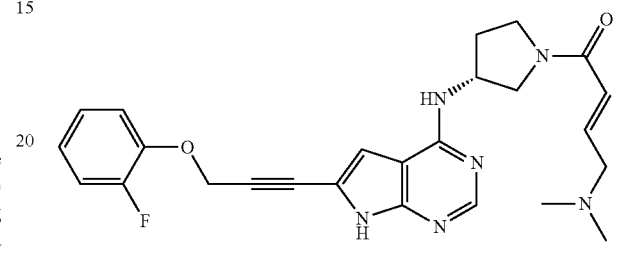

Preparation of (R,E)-1-(3-((6-(3-(2-fluorophenoxy)prop-1-yn-1-yl)-7H-pyrrolo[2,3-d]pyrimidin-4-yl)amino)pyrrolidin-1-yl)-4-(dimethylamino)but-2-en-1-one The title compound was prepared by using essentially the same procedure as in Example 42 except in the last step using (E)-4-(dimethylamino)but-2-enoic acid and HBTU in DMF instead of the acryloyl chloride by adding HBTU into a solution of the amine, triethylamine and (E)-4-(dimethylamino)but-2-enoic acid in DMF, stirred for 2 hours. This mixture was directly separated by Prep HPLC affording a solid product, MS (+) ES: 463 (M+H)$^+$.

Reaction Scheme 5

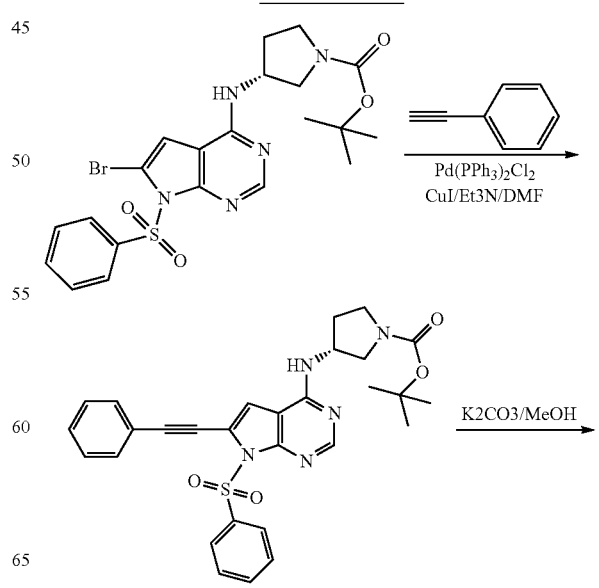

-continued

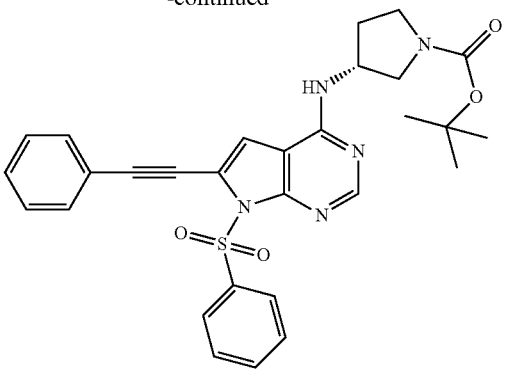

This compound was prepared by using essentially the same procedure as in Example 33 (Step 2) except in the last step by using ethynylbenzene instead of the (prop-2-yn-1-yloxy)benzene affording a solid product, MS (+) ES: 544 (M+H)⁺.

Step 2. Preparation of tert-butyl (R)-3-((6-(phenylethynyl)-7H-pyrrolo[2,3-d]pyrimidin-4-yl)amino)pyrrolidine-1-carboxylate

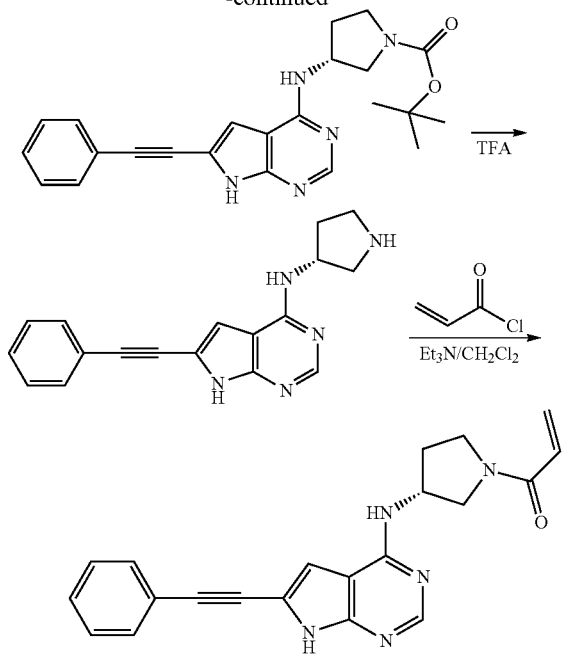

Example 50

Preparation of (R)-1-(3-((6-(phenylethynyl)-7H-pyrrolo[2,3-d]pyrimidin-4-yl)amino)pyrrolidin-1-yl)prop-2-en-1-one

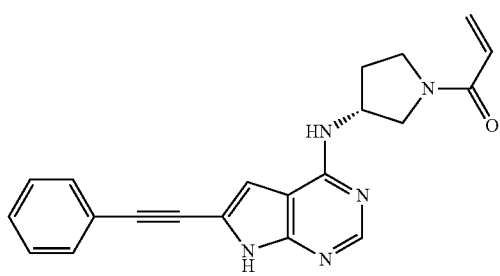 [SMILES: C=CC(=O)N1CC[C@@H](Nc2ncnc3[nH]c(C#Cc4ccccc4)cc23)C1]

Step 1. Preparation of tert-butyl (R)-3-((6-(phenylethynyl)-7-(phenylsulfonyl)-7H-pyrrolo[2,3-d]pyrimidin-4-yl)amino)pyrrolidine-1-carboxylate This compound is prepared by using essentially the same procedure as in Example 33 (Step 3) affording a solid product, MS (+) ES: 404 (M+H)⁺.

Step 3. Preparation of (R)-6-(phenylethynyl)-N-(pyrrolidin-3-yl)-7H-pyrrolo[2,3-d]pyrimidin-4-amine

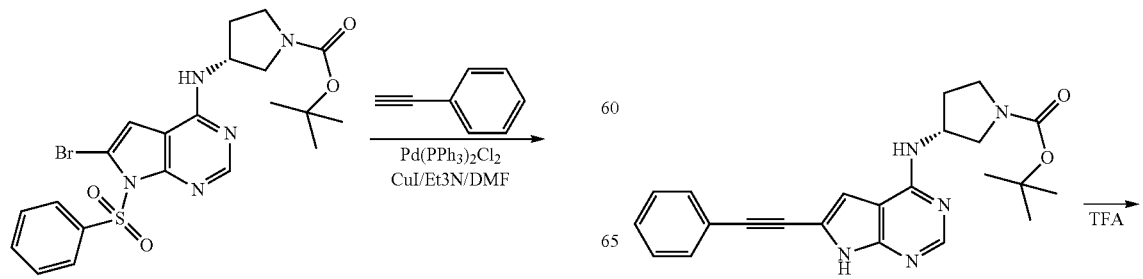

-continued

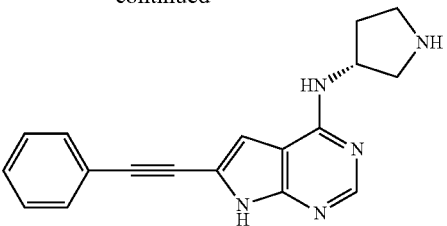

This compound was prepared by using essentially the same procedure as in Example 33 (Step 4) affording a solid product, MS (+) ES: 304 (M+H)$^+$.

Step 4. Preparation of (R)-1-(3-((6-(phenylethynyl)-7H-pyrrolo[2,3-d]pyrimidin-4-yl)amino)pyrrolidin-1-yl)prop-2-en-1-one (Example 50)

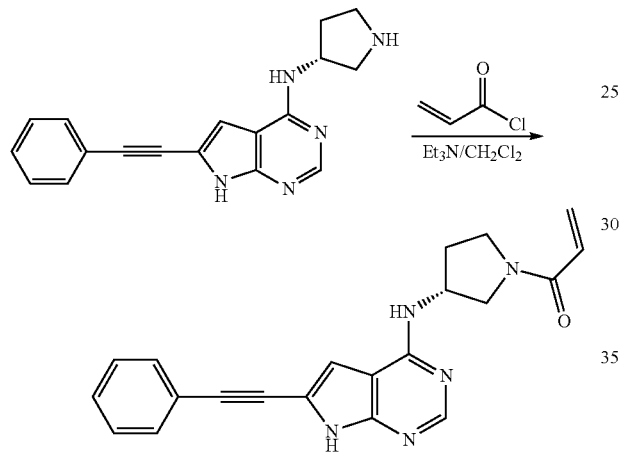

This compound was prepared by using essentially the same procedure as in Example 33 (Step 5) affording a solid product, MS (+) ES: 358 (M+H)$^+$.

Example 51

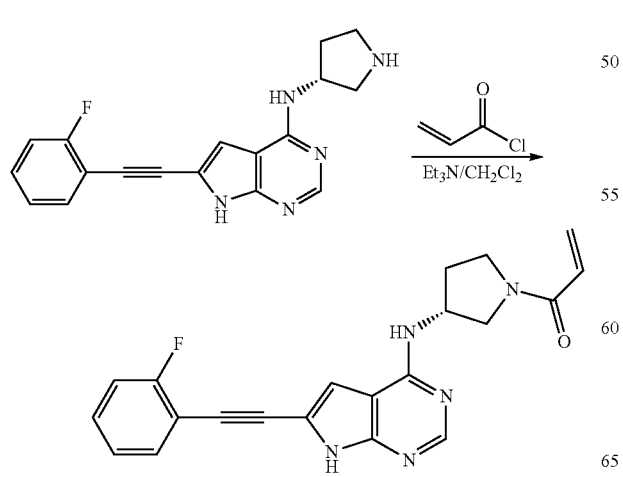

Preparation of (R)-1-(3-((6-((2-fluorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-2-fluorobenzene instead of ethynylbenzene in step 1 affording a solid product, MS (+) ES: 376 (M+H)$^+$.

Example 52

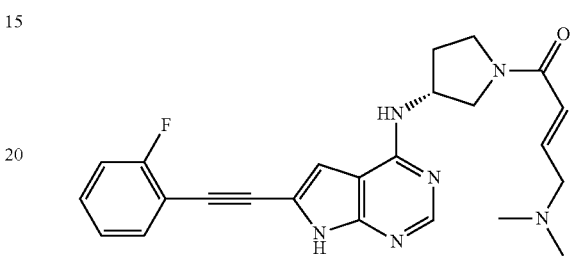

Preparation of (R,E)-4-(dimethylamino)-1-(3-((6-((2-fluorophenyl)ethynyl)-7H-pyrrolo[2,3-d]pyrimidin-4-yl)amino)pyrrolidin-1-yl)but-2-en-1-one The title compound was prepared by using essentially the same procedure as in Example 51 except in the last step using (E)-4-(dimethylamino)but-2-enoic acid and HBTU in DMF instead of the acryloyl chloride by adding HBTU into a solution of the amine, triethylamine and (E)-4-(dimethylamino)but-2-enoic acid in DMF, stirred for 2 hours. This mixture was directly separated by Prep HPLC affording a solid product, MS (+) ES: 433 (M+H)$^+$.

Example 53

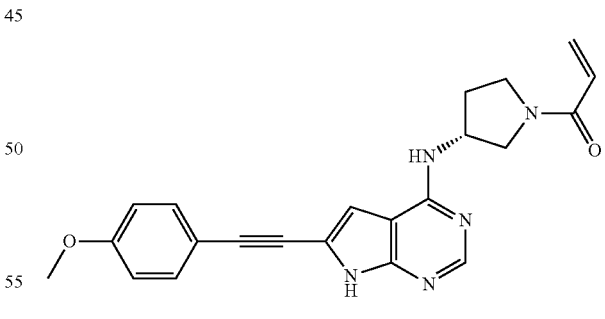

Preparation of (R)-1-(3-((6-((4-methoxyphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-4-methoxybenzene instead of ethynylbenzene in step 1 affording a solid product, MS (+) ES: 388 (M+H)$^+$.

Example 54

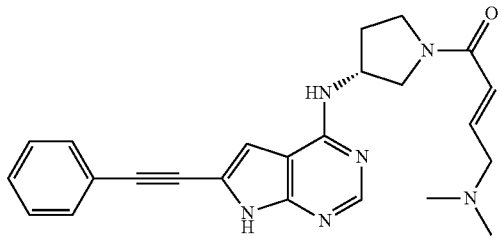 [SMILES: CN(C)C/C=C/C(=O)N1CC[C@@H](Nc2ncnc3[nH]c(C#Cc4ccccc4)cc23)C1]

Preparation of (R,E)-4-(dimethylamino)-1-(3-((6-(phenylethynyl)-7H-pyrrolo[2,3-d]pyrimidin-4-yl)amino)pyrrolidin-1-yl)but-2-en-1-one The title compound was prepared by using essentially the same procedure as in Example 50 except in the last step using (E)-4-(dimethylamino)but-2-enoic acid and HBTU in DMF instead of the acryloyl chloride by adding HBTU into a solution of the amine, triethylamine and (E)-4-(dimethylamino)but-2-enoic acid in DMF, stirred for 2 hours. This mixture was directly separated by Prep HPLC affording a solid product, MS (+) ES: 415 (M+H)$^+$.

Example 55

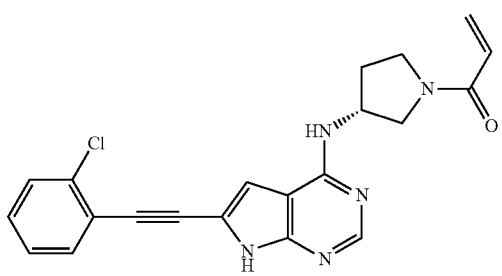 [SMILES: C=CC(=O)N1CC[C@@H](Nc2ncnc3[nH]c(C#Cc4ccccc4Cl)cc23)C1]

Preparation of (R)-1-(3-((6-((2-chlorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-2-chlorobenzene instead of ethynylbenzene in step 1 affording a solid product, MS (+) ES: 392 (M+H)$^+$.

Example 56

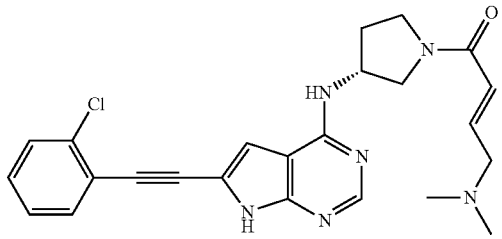 [SMILES: CN(C)C/C=C/C(=O)N1CC[C@@H](Nc2ncnc3[nH]c(C#Cc4ccccc4Cl)cc23)C1]

Preparation of (R,E)-1-(3-((6-((2-chlorophenyl)ethynyl)-7H-pyrrolo[2,3-d]pyrimidin-4-yl)amino)pyrrolidin-1-yl)-4-(dimethylamino)but-2-en-1-one The title compound was prepared by using essentially the same procedure as in Example 55 except in the last step using (E)-4-(dimethylamino)but-2-enoic acid and HBTU in DMF instead of the acryloyl chloride by adding HBTU into a solution of the amine, triethylamine and (E)-4-(dimethylamino)but-2-enoic acid in DMF, stirred for 2 hours. This mixture was directly separated by Prep HPLC affording a solid product, MS (+) ES: 449 (M+H)$^+$.

Example 57

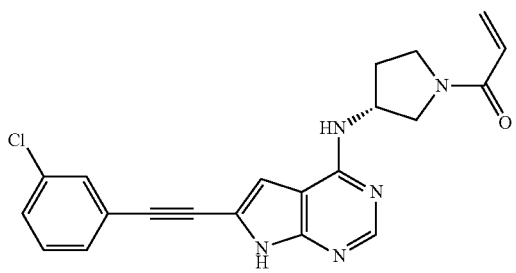 [SMILES: C=CC(=O)N1CC[C@@H](Nc2ncnc3[nH]c(C#Cc4cccc(Cl)c4)cc23)C1]

Preparation of (R)-1-(3-((6-((3-chlorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3-chlorobenzene instead of ethynylbenzene in step 1 affording a solid product, MS (+) ES: 392 (M+H)$^+$.

Example 58

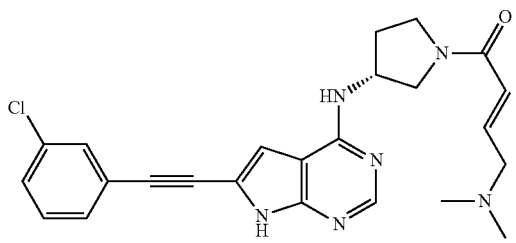 [SMILES: CN(C)C/C=C/C(=O)N1CC[C@@H](Nc2ncnc3[nH]c(C#Cc4cccc(Cl)c4)cc23)C1]

Preparation of (R,E)-1-(3-((6-((3-chlorophenyl)ethynyl)-7H-pyrrolo[2,3-d]pyrimidin-4-yl)amino)pyrrolidin-1-yl)-4-(dimethylamino)but-2-en-1-one The title compound was prepared by using essentially the same procedure as in Example 57 except in the last step using (E)-4-(dimethylamino)but-2-enoic acid and HBTU in DMF instead of the acryloyl chloride by adding HBTU into a solution of the amine, triethylamine and (E)-4-(dimethylamino)but-2-enoic acid in DMF, stirred for 2 hours. This mixture was directly separated by Prep HPLC affording a solid product, MS (+) ES: 449 (M+H)$^+$.

Example 59

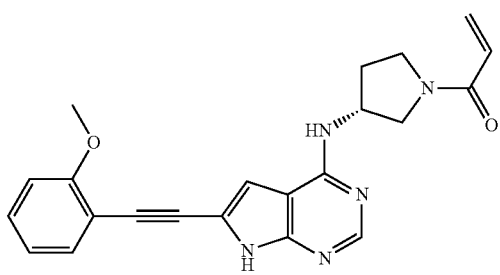 [SMILES: C=CC(=O)N1CC[C@@H](Nc2ncnc3[nH]c(C#Cc4ccccc4OC)cc23)C1]

Preparation of (R)-1-(3-((6-((2-methoxyphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-2-methoxybenzene instead of ethynylbenzene in step 1 affording a solid product, MS (+) ES: 388 (M+H)$^+$.

Example 60

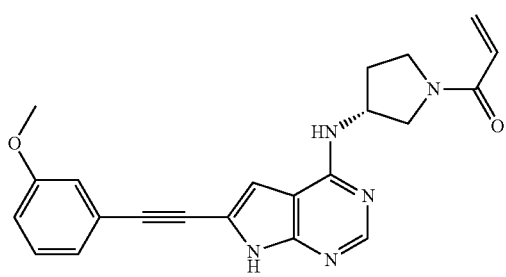 [SMILES: C=CC(=O)N1CC[C@@H](Nc2ncnc3[nH]c(C#Cc4cccc(OC)c4)cc23)C1]

Preparation of (R)-1-(3-((6-((3-methoxyphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3-methoxybenzene instead of ethynylbenzene in step 1 affording a solid product, MS (+) ES: 388 (M+H)$^+$.

Example 61

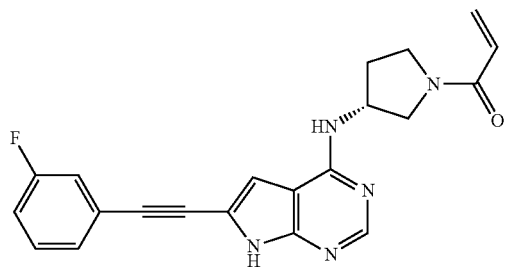

Preparation of (R)-1-(3-((6-((3-fluorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3-fluorobenzene instead of ethynylbenzene in step 1 affording a solid product, MS (+) ES: 376 (M+H)$^+$.

Example 62

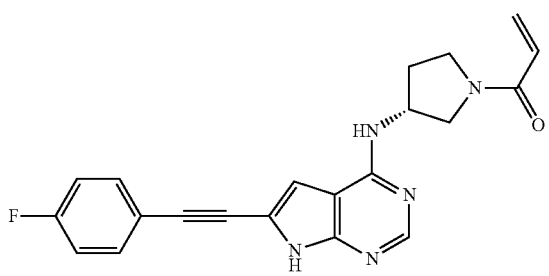 [SMILES: C=CC(=O)N1CC[C@@H](Nc2ncnc3[nH]c(C#Cc4ccc(F)cc4)cc23)C1]

Preparation of (R)-1-(3-((6-((4-fluorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-4-fluorobenzene instead of ethynylbenzene in step 1 affording a solid product, MS (+) ES: 376 (M+H)$^+$.

Example 63

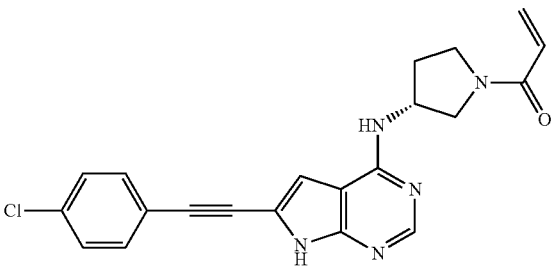 [SMILES: C=CC(=O)N1CC[C@@H](Nc2ncnc3[nH]c(C#Cc4ccc(Cl)cc4)cc23)C1]

Preparation of (R)-1-(3-((6-((4-chlorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-4-chlorobenzene instead of ethynylbenzene in step 1 affording a solid product, MS (+) ES: 392 (M+H)$^+$.

Example 64

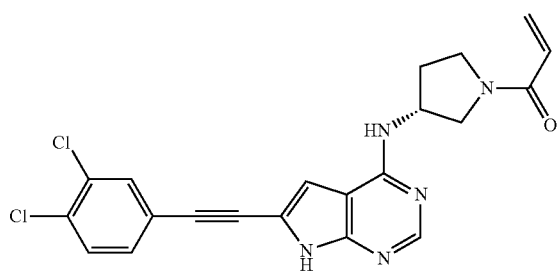 [SMILES: C=CC(=O)N1CC[C@@H](Nc2ncnc3[nH]c(C#Cc4ccc(Cl)c(Cl)c4)cc23)C1]

Preparation of (R)-1-(3-((6-((3,4-dichlorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3,4-dichlorobenzene instead of ethynylbenzene in step 1 affording a solid product, MS (+) ES: 427 (M+H)$^+$.

Example 65

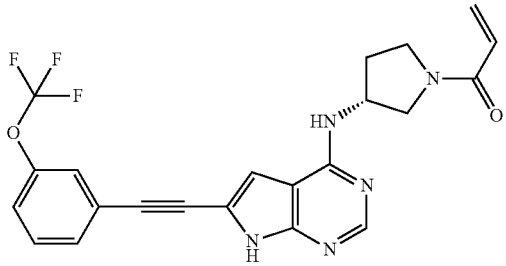 [SMILES: C=CC(=O)N1CC[C@@H](Nc2ncnc3[nH]c(C#Cc4cccc(OC(F)(F)F)c4)cc23)C1]

Preparation of (R)-1-(3-((6-((3-trifluoromethoxyphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3-trifluoromethoxybenzene instead of ethynylbenzene in step 1 affording a solid product, MS (+) ES: 442 (M+H)$^+$.

Example 66

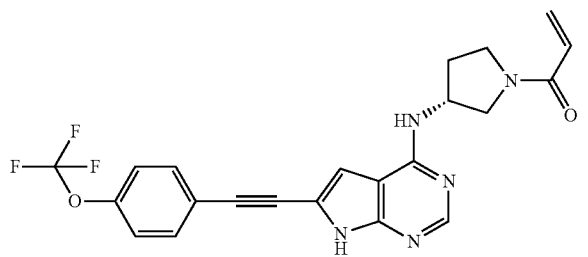 [SMILES: C=CC(=O)N1CC[C@@H](Nc2ncnc3[nH]c(C#Cc4ccc(OC(F)(F)F)cc4)cc23)C1]

Preparation of (R)-1-(3-((6-((4-trifluoromethoxyphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-4-trifluoromethoxybenzene instead of ethynylbenzene in step 1 affording a solid product, MS (+) ES: 442 (M+H)$^+$.

Example 67

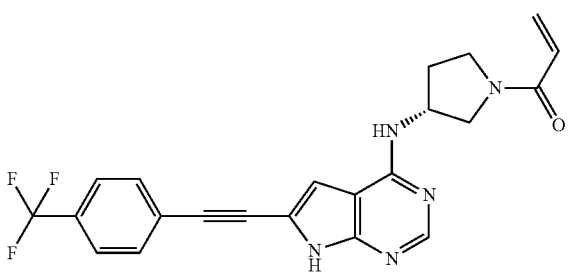 [SMILES: C=CC(=O)N1CC[C@@H](Nc2ncnc3[nH]c(C#Cc4ccc(C(F)(F)F)cc4)cc23)C1]

Preparation of (R)-1-(3-((6-((4-trifluoromethylphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-4-trifluoromethylbenzene instead of ethynylbenzene in step 1 affording a solid product, MS (+) ES: 426 (M+H)$^+$.

Example 68

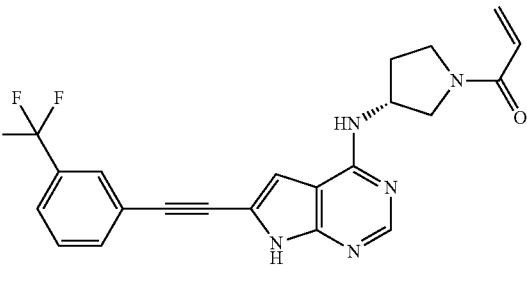

Preparation of (R)-1-(3-((6-((3-trifluoromethylphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3-trifluoromethylbenzene instead of ethynylbenzene in step 1 affording a solid product, MS (+) ES: 426 (M+H)$^+$.

Example 69

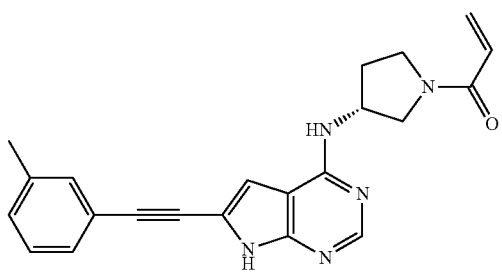 [SMILES: C=CC(=O)N1CC[C@@H](Nc2ncnc3[nH]c(C#Cc4cccc(C)c4)cc23)C1]

Preparation of (R)-1-(3-((6-((3-methylphenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-ethynyl-3-methylbenzene instead of ethynylbenzene in step 1 affording a solid product, MS (+) ES: 372 (M+H)$^+$.

Example 70

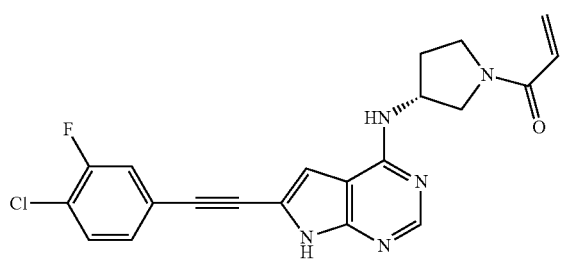 [SMILES: C=CC(=O)N1CC[C@@H](Nc2ncnc3[nH]c(C#Cc4ccc(Cl)c(F)c4)cc23)C1]

Preparation of (R)-1-(3-((6-((3-fluoro-4-chlorophenyl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 1-chloro-4-ethynyl-2-fluorobenzene instead of ethynylbenzene in step 1 affording a solid product, MS (+) ES: 410 (M+H)$^+$.

Example 71

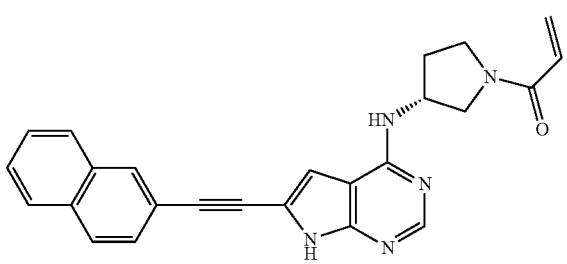 [SMILES: C=CC(=O)N1CC[C@@H](Nc2ncnc3[nH]c(C#Cc4ccc5ccccc5c4)cc23)C1]

Preparation of (R)-1-(3-((6-(naphthalen-2-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 2-ethynylnaphthalene instead of ethynylbenzene in step 1 affording a solid product, MS (+) ES: 408 (M+H)$^+$.

Example 72

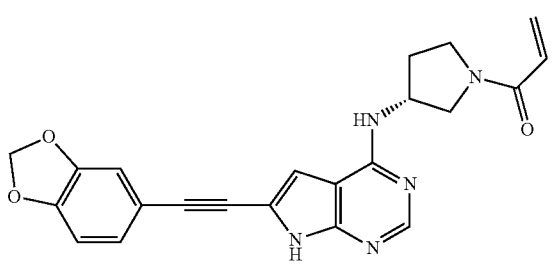 [SMILES: C=CC(=O)N1CC[C@@H](Nc2ncnc3[nH]c(C#Cc4ccc5c(c4)OCO5)cc23)C1]

Preparation of (R)-1-(3-((6-(benzo[d][1,3]dioxol-5-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 5-ethynylbenzo[d][1,3]dioxole (prepared through 5-bromobenzo[d][1,3]dioxole based on reference of "Pearson, William H.; Postich, Michael J. Journal of Organic Chemistry, 1994, vol. 59, #19 p. 5662-5671) instead of ethynylbenzene in step 1 affording a solid product, MS (+) ES: 402 (M+H)$^+$.

Example 73

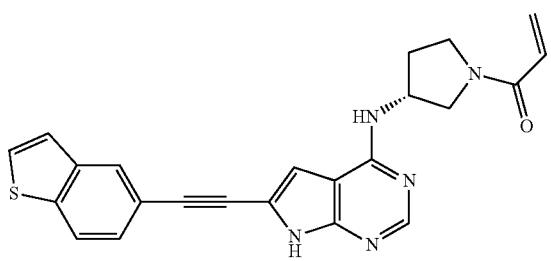 [SMILES: C=CC(=O)N1CC[C@@H](Nc2ncnc3[nH]c(C#Cc4ccc5occc5c4)cc23)C1]

Preparation of (R)-1-(3-((6-(benzo[b]thiophen-5-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 5-ethynylbenzo[b]thiophene (prepared through 5-bromobenzo[b]thiophene based on reference of "Pearson, William H.; Postich, Michael J. Journal of Organic Chemistry, 1994, vol. 59, #19 p. 5662-5671) instead of ethynylbenzene in step 1 affording a solid product, MS (+) ES: 414 (M+H)$^+$.

Example 74

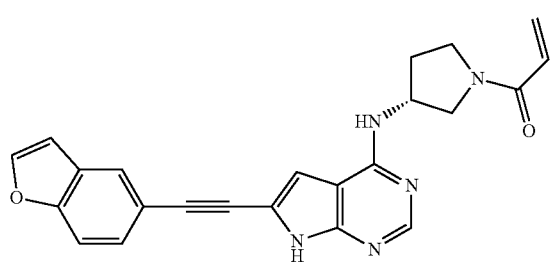

Preparation of (R)-1-(3-((6-(benzofuran-5-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 5-ethynylbenzofuran (prepared through 5-bromobenzofuran based on reference of "Pearson, William H.; Postich, Michael J. Journal of Organic Chemistry, 1994, vol. 59, #19 p. 5662-5671) instead of ethynylbenzene in step 1 affording a solid product, MS (+) ES: 398 (M+H)$^+$.

Example 75

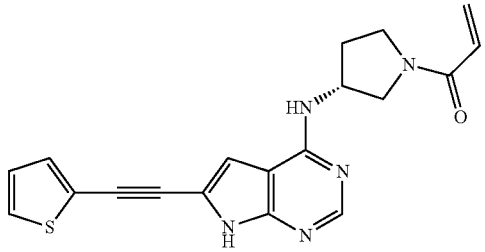 [SMILES: C=CC(=O)N1CC[C@@H](Nc2ncnc3[nH]c(C#Cc4cccs4)cc23)C1]

Preparation of (R)-1-(3-((6-(thiophen-2-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 2-ethynylthiophene (prepared through 2-bromothiophene based on reference of "Pearson, William H.; Postich, Michael J. Journal of Organic Chemistry, 1994, vol. 59, #19 p. 5662-5671) instead of ethynylbenzene in step 1 affording a solid product, MS (+) ES: 364 (M+H)$^+$.

Example 76

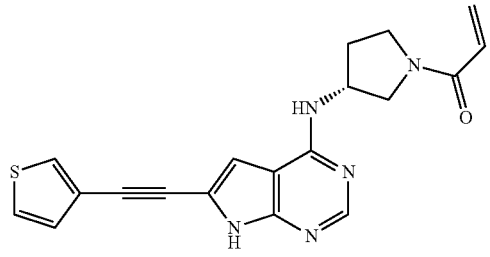 [SMILES: C=CC(=O)N1CC[C@@H](Nc2ncnc3[nH]c(C#Cc4ccsc4)cc23)C1]

Preparation of (R)-1-(3-((6-(thiophen-3-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 3-ethynylthiophene (prepared through 3-bromothiophene based on reference of "Pearson, William H.; Postich, Michael J. Journal of Organic Chemistry, 1994, vol. 59, #19 p. 5662-5671) instead of ethynylbenzene in step 1 affording a solid product, MS (+) ES: 364 (M+H)$^+$.

Example 77

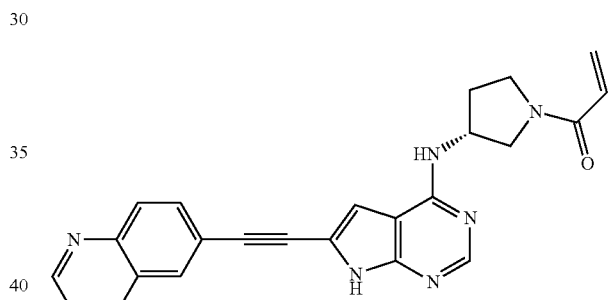

Preparation of (R)-1-(3-((6-(quinolin-6-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 6-ethynylquinoline (prepared through 6-bromoquinoline based on reference of "Pearson, William H.; Postich, Michael J. Journal of Organic Chemistry, 1994, vol. 59, #19 p. 5662-5671) instead of ethynylbenzene in step 1 affording a solid product, MS (+) ES: 409 (M+H)$^+$.

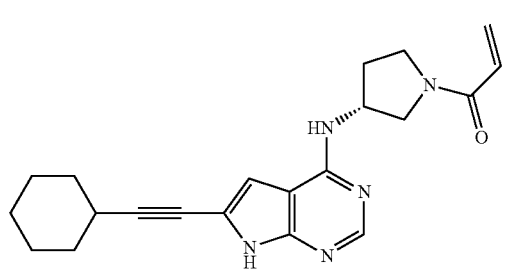 [SMILES: C=CC(=O)N1CC[C@@H](Nc2ncnc3[nH]c(C#CC4CCCCC4)cc23)C1]

Example 78

Preparation of (R)-1-(3-((6-(cyclohexylethynyl)-7H-pyrrolo[2,3-d]pyrimidin-4-yl)amino)pyrrolidin-1-yl)prop-2-en-1-one This compound was prepared by using essentially the same procedure as in Example 50 by using ethynylcyclohexane instead of ethynylbenzene in step 1 affording a solid product, MS (+) ES: 364 (M+H)+.

Example 79

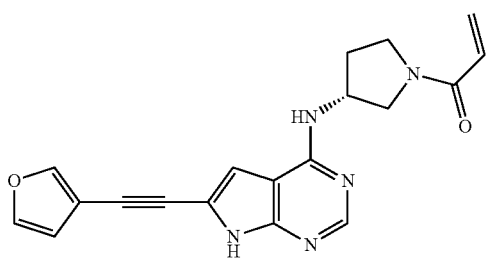 [SMILES: C=CC(=O)N1CC[C@@H](Nc2ncnc3[nH]c(C#Cc4ccoc4)cc23)C1]

Preparation of (R)-1-(3-((6-(furan-3-ylethynyl)-7H-pyrrolo[2,3-d]pyrimidin-4-yl)amino)pyrrolidin-1-yl)prop-2-en-1-one This compound was prepared by using essentially the same procedure as in Example 50 by using 3-ethynylfuran (prepared through furan-3-carbaldehyde based on reference of "Brueckner, Reinhard; Von Der Ohe, Frank, Tetrahedron Letters, 1998, vol. 39, #14 p. 1909-1910) instead of ethynylbenzene in step 1 affording a solid product, MS (+) ES: 347 (M+H)+.

Example 80

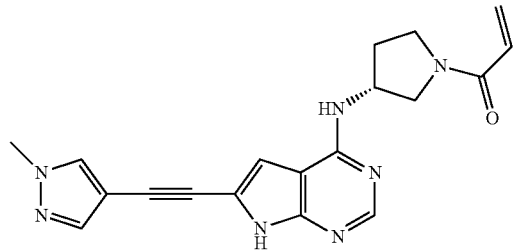 [SMILES: C=CC(=O)N1CC[C@@H](Nc2ncnc3[nH]c(C#Cc4cnn(C)c4)cc23)C1]

Preparation of (R)-1-(3-((6-((1-methyl-1H-pyrazol-4-yl)ethynyl)-7H-pyrrolo[2,3-d]pyrimidin-4-yl)amino)pyrrolidin-1-yl)prop-2-en-1-one This compound was prepared by using essentially the same procedure as in Example 50 by using 4-ethynyl-1-methyl-1H-pyrazole instead of ethynylbenzene in step 1 affording a solid product, MS (+) ES: 362 (M+H)+.

Example 81

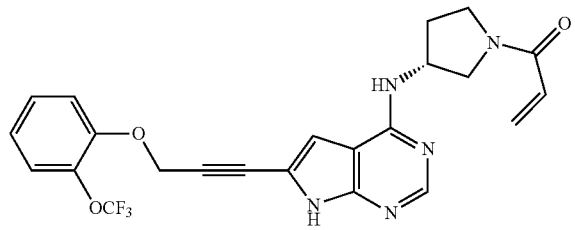

Preparation of (R)-1-(3-((6-(3-(2-(trifluoromethoxy)phenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 1-(prop-2-yn-1-yloxy)-2-(trifluoromethoxy)benzene instead of the (prop-2-yn-1-yloxy)benzene affording a solid product, MS (+) ES: 472 (M+H)+.

Example 82

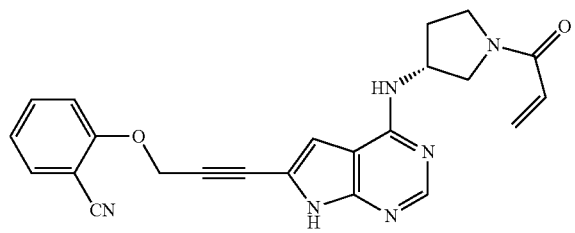

Preparation of (R)-1-(3-((6-(3-(2-cyanophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 1-(prop-2-yn-1-yloxy)-2-cyanobenzene instead of the (prop-2-yn-1-yloxy)benzene affording a solid product, MS (+) ES: 413 (M+H)+.

Example 83

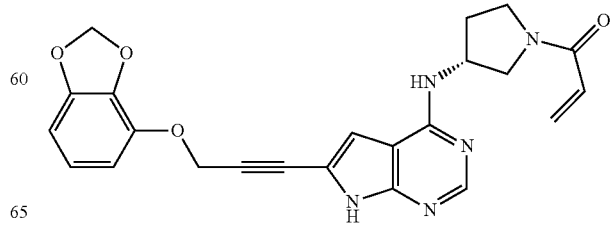

Preparation of (R)-1-(3-((6-(3-(benzo[d][1,3]dioxol-4-yloxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 4-(prop-2-yn-1-yloxy)benzo[d][1,3]dioxole (prepared by the same method as of Maharoof, Umar S. M.; Mateo, Mary E.; Rigby, James H. Journal of the American Chemical Society, 2000, vol. 122, #28 p. 6624-6628 to obtain the phenol, followed by the alkylation with 3-bromoprop-1-yne and potassium carbonate in DMF to yield the product) instead of the (prop-2-yn-1-yloxy)benzene affording a solid product, MS (+) ES: 432 (M+H)+.

Example 84

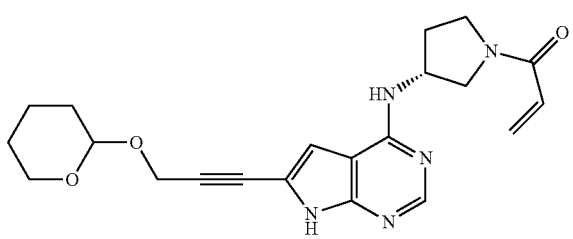 [SMILES: C=CC(=O)N1CC[C@@H](Nc2ncnc3[nH]c(C#CCOC4CCCCO4)cc23)C1]

Preparation of 1-((3R)-3-((6-(3-((tetrahydro-2H-pyran-2-yl)oxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 2-(prop-2-yn-1-yloxy)tetrahydro-2H-pyran instead of the (prop-2-yn-1-yloxy)benzene affording a solid product, MS (+) ES: 396 (M+H)+.

Example 85

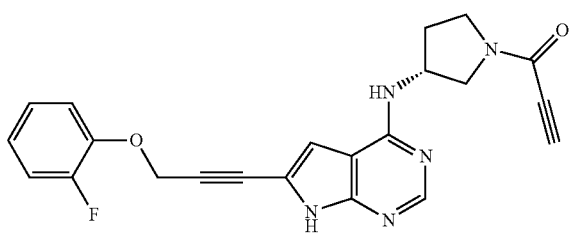 [SMILES: C#CC(=O)N1CC[C@@H](Nc2ncnc3[nH]c(C#CCOc4ccccc4F)cc23)C1]

Preparation of (R)-1-(3-((6-(3-(2-fluorophenoxy)prop-1-yn-1-yl)-7H-pyrrolo[2,3-d]pyrimidin-4-yl)amino)pyrrolidin-1-yl)prop-2-yn-1-one The title compound was prepared by using essentially the same procedure as in Example 42 except in the last step using propiolic acid and HATU, triethylamine in DMF by adding HATU into a solution of the amine, triethylamine and propiolic acid in DMF, stirred for 2 hours. This mixture was directly separated by Prep HPLC affording a solid product, MS (+) ES: 404 (M+H)+.

Example 86

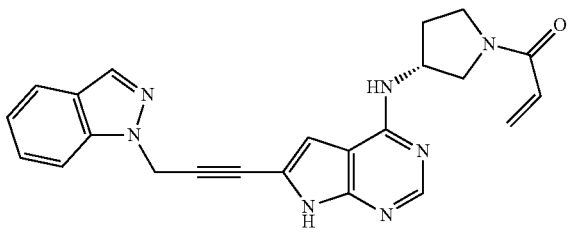 [SMILES: C=CC(=O)N1CC[C@@H](Nc2ncnc3[nH]c(C#CCn4ncc5ccccc54)cc23)C1]

Preparation of (R)-1-(3-((6-(3-(1H-indazol-1-yl)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 1-(prop-2-yn-1-yl)-1H-indazole (Crowley; Flynn; Maresca; Mason; O'Donnell; Walser; Yaremko Journal of Medicinal Chemistry, 1991, vol. 34, #3 p. 1209-1221) instead of the (prop-2-yn-1-yloxy)benzene affording a solid product, MS (+) ES: 412 (M+H)+.

Example 87

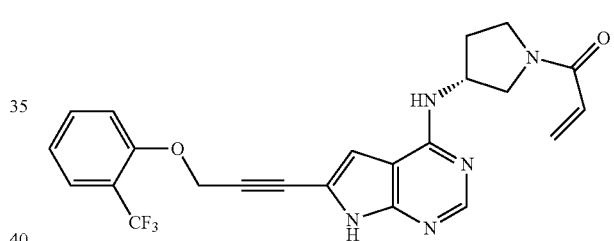

Preparation of (R)-1-(3-((6-(3-(2-(trifluoromethyl)phenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 1-(prop-2-yn-1-yloxy)-2-(trifluoromethyl)benzene instead of the (prop-2-yn-1-yloxy)benzene affording a solid product, MS (+) ES: 456 (M+H)+.

Example 88

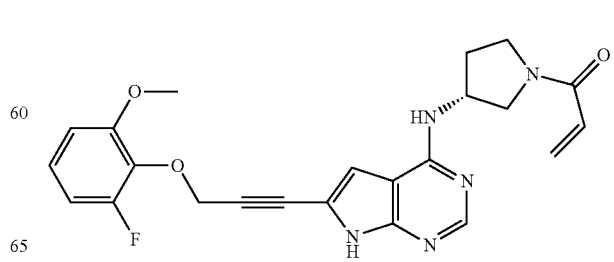

Preparation of (R)-1-(3-((6-(3-(2-fluoro-6-methoxy-phenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 1-fluoro-3-methoxy-2-(prop-2-yn-1-yloxy)benzene instead of the (prop-2-yn-1-yloxy)benzene affording a solid product, MS (+) ES: 436 (M+H)+.

Example 89

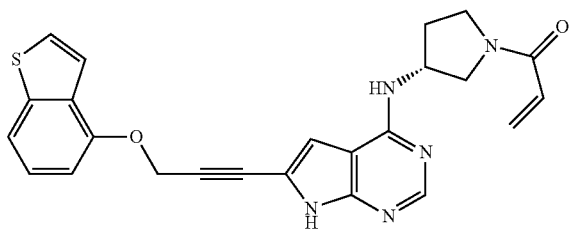 [SMILES: C=CC(=O)N1CC[C@@H](Nc2ncnc3[nH]c(C#CCOc4cccc5sccc45)cc23)C1]

Preparation of (R)-1-(3-((6-(3-(benzo[b]thiophen-4-yloxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 4-(prop-2-yn-1-yloxy)benzo[b]thiophene instead of the (prop-2-yn-1-yloxy)benzene in step 1 affording a solid product, MS (+) ES: 444 (M+H)+.

Example 90

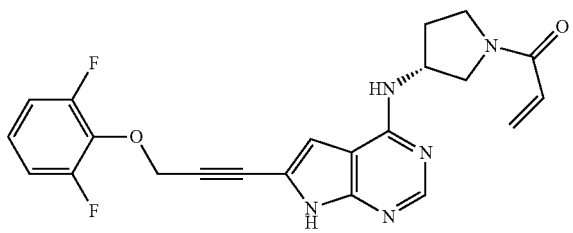 [SMILES: C=CC(=O)N1CC[C@@H](Nc2ncnc3[nH]c(C#CCOc4c(F)cccc4F)cc23)C1]

Preparation of (R)-1-(3-((6-(3-(2,6-difluorophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 1,3-difluoro-2-(prop-2-yn-1-yloxy)benzene instead of the (prop-2-yn-1-yloxy)benzene affording a solid product, MS (+) ES: 424 (M+H)+.

Example 91

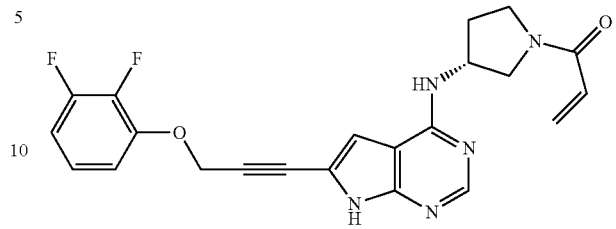

Preparation of (R)-1-(3-((6-(3-(2,3-difluorophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 2,3-difluoro(prop-2-yn-1-yloxy)benzene instead of the (prop-2-yn-1-yloxy)benzene in step 1 affording a solid product, MS (+) ES: 424 (M+H)+.

Example 92

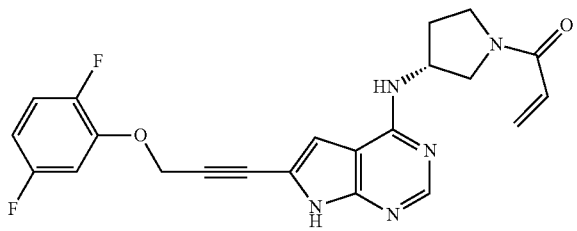 [SMILES: C=CC(=O)N1CC[C@@H](Nc2ncnc3[nH]c(C#CCOc4cc(F)ccc4F)cc23)C1]

Preparation of (R)-1-(3-((6-(3-(2,5-difluorophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 2 by using 2,5-difluoro(prop-2-yn-1-yloxy)benzene instead of the (prop-2-yn-1-yloxy)benzene in step 1 affording a solid product, MS (+) ES: 424 (M+H)+.

Example 93

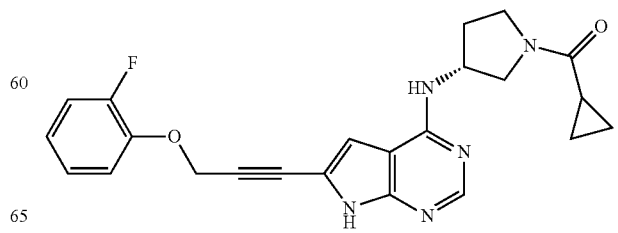

Preparation of (R)-cyclopropyl(3-((6-(3-(2-fluoro-phenoxy)prop-1-yn-1-yl)-7H-pyrrolo[2,3-d]pyrimidin-4-yl)amino)pyrrolidin-1-yl)methanone The title compound was prepared by using essentially the same procedure as in Example 42 except in the last step using cyclopropanecarboxylic acid and HATU, triethylamine in DMF instead of the acyl chloride by adding HATU into a solution of the amine, triethylamine and cyclopropanecarboxylic acid in DMF, stirred for 2 hours. This mixture was directly separated by Prep HPLC affording a solid product, MS (+) ES: 420 (M+H)+.

Example 94

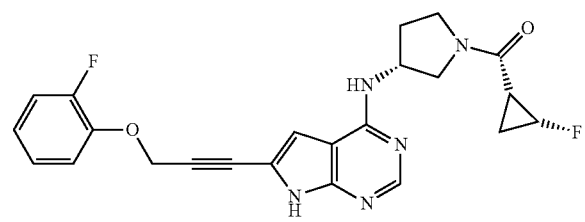

Preparation of ((1R,2R)-2-fluorocyclopropyl)((R)-3-((6-(3-(2-fluorophenoxy)prop-1-yn-1-yl)-7H-pyrrolo[2,3-d]pyrimidin-4-yl)amino)pyrrolidin-1-yl)methanone The title compound was prepared by using essentially the same procedure as in Example 42 except in the last step using (1R,2R)-2-fluorocyclopropanecarboxylic acid and HATU, triethylamine in DMF instead of the acyl chloride by adding HATU into a solution of the amine, triethylamine and (1R,2R)-2-fluorocyclopropanecarboxylic acid in DMF, stirred for 2 hours. This mixture was directly separated by Prep HPLC affording a solid product, MS (+) ES: 438 (M+H)+.

Example 95

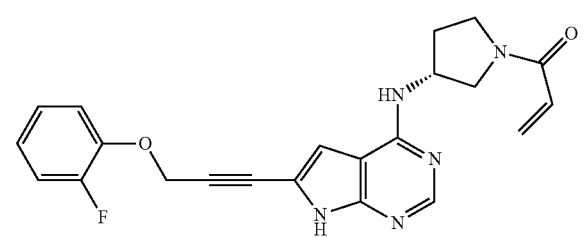 [SMILES: C=CC(=O)N1CC[C@@H](Nc2ncnc3[nH]c(C#CCOc4ccccc4F)cc23)C1]

Preparation of (S)-1-(3-((6-(3-(2-fluorophenoxy)prop-1-yn-1-yl)-7H-pyrrolo[2,3-d]pyrimidin-4-yl)amino)pyrrolidin-1-yl)prop-2-en-1-one The title compound was prepared by using essentially the same procedure as in Example 40 except in the Step 1 using the S isomer of 3-aminopyrrolidine-1-carboxylate affording a solid product, MS (+) ES: 406 (M+H)+.

Example 96

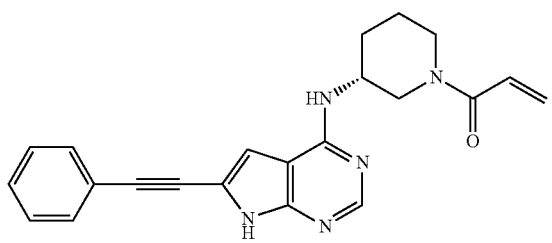 [SMILES: C=CC(=O)N1CCC[C@@H](Nc2ncnc3[nH]c(C#Cc4ccccc4)cc23)C1]

Preparation of (R)-1-(3-((6-(phenylethynyl)-7H-pyrrolo[2,3-d]pyrimidin-4-yl)amino)piperidin-1-yl)prop-2-en-1-one The title compound was prepared by using essentially the same procedure as in Example 50 except in the Step 1 by using (R)-tert-butyl 3-((6-bromo-7-(phenylsulfonyl)-7H-pyrrolo[2,3-d]pyrimidin-4-yl)amino)piperidine-1-carboxylate instead of (R)-tert-butyl 3-((6-bromo-7-(phenylsulfonyl)-7H-pyrrolo[2,3-d]pyrimidin-4-yl)amino)pyrrolidine-1-carboxylate affording a solid product, MS (+) ES: 372 (M+H)+.

Example 97

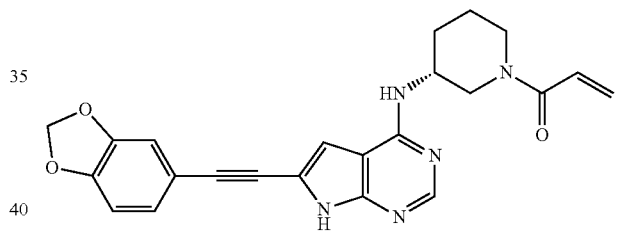

Preparation of (R)-1-(3-((6-(benzo[d][1,3]dioxol-5-ylethynyl)-7H-pyrrolo[2,3-d]pyrimidin-4-yl)amino)piperidin-1-yl)prop-2-en-1-one The title compound was prepared by using essentially the similar procedure as in Example 96 except by using 5-ethynylbenzo[d][1,3]dioxole instead of ethynylbenzene in step 2 affording a solid product, MS (+) ES: 416 (M+H)+.

Example 98

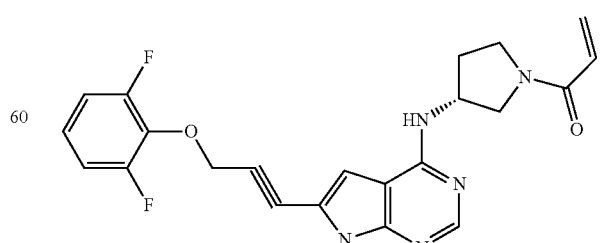

Preparation of (R)-1-(3-((8-(3-(2,6-difluorophe-noxy)prop-1-yn-1-yl)-9H-purin-6-yl)amino)pyrrolidin-1-yl)prop-2-en-1-one

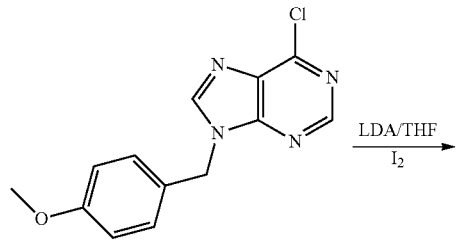

Step 1. Preparation of 8-bromo-6-chloro-9-(4-methoxybenzyl)-9H-purine

6-Chloro-9-(4-methoxyphenylmethyl)-9H-purine (272 mg, 0.99 mmol) in THF (4 mL) was added dropwise to a stirred solution of LDA [generated in situ from diisopropylamine (0.21 mL, 1.50 mmol) and n-BuLi (0.88 mL, 1.40 mmol, 1.6 M in hexane)] in THF (4 mL) at −78° C. under N₂. After stirring for 1 hour at −78° C., a solution of iodine (303 mg, 1.20 mmol) in THF (4 mL) was added dropwise and the resulting mixture was stirred at −78° C. for 5 hours, gradually warmed to ambient temperature over 2 hours and stirred at ambient temperature for 14 hours. Sat. aq. NH₄Cl (15 mL) was added and the mixture as extracted with EtOAc (2*25 mL). The combined organic extracts were washed with brine (20 mL), dried (MgSO₄) and evaporated in vacuo. The product was purified by flash chromatography on silica gel eluding with EtOAc-hexane to yield 220 mg (55%), MS (+) ES: 401 (M+H)⁺.

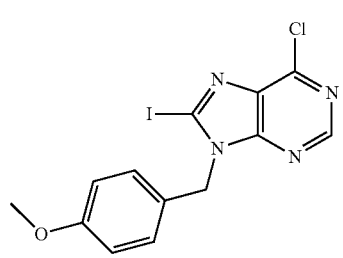

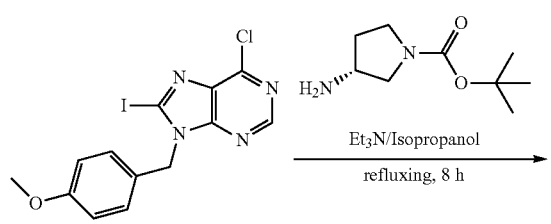

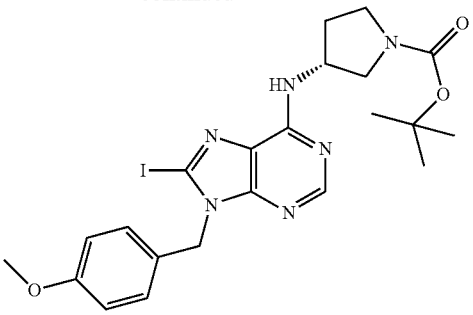

Step 2. Preparation of (R)-tert-butyl 3-((8-iodo-9-(4-methoxybenzyl)-9H-purin-6-yl)amino)pyrrolidine-1-carboxylate A mixture of 8-bromo-6-chloro-9-(4-methoxybenzyl)-9H-purine (400 mg, 1 mmol), tert-butyl (R)-3-aminopyrrolidine-1-carboxylate (186 mg, 1 mmol) and triethylamine (150 mg, 1.5 mmol) in isopropyl alcohol (10 mL) was heated in a Microwave reactor to 120° C. for 3 hours. The mixture was cooled to room temperature and the volatile solvents were evaporated under reduced pressure to dryness. The product was purified by flash chromatography with hexanes/ethyl acetate to afford the product as a form white solid 380 mg, yield 70%, MS (+) ES: 551 (M+H)⁺.

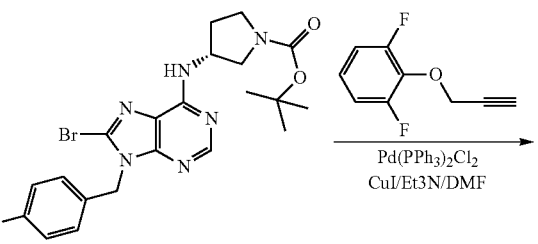

Step 3. Preparation of (R)-tert-butyl 3-((8-(3-(2,6-difluorophenoxy)prop-1-yn-1-yl)-9-(4-methoxybenzyl)-9H-purin-6-yl)amino)pyrrolidine-1-carboxylate The title compound was prepared by using essentially the similar procedure as in Example 6, Step 4 affording a solid product (60%), MS (+) ES: 591 (M+H)⁺.

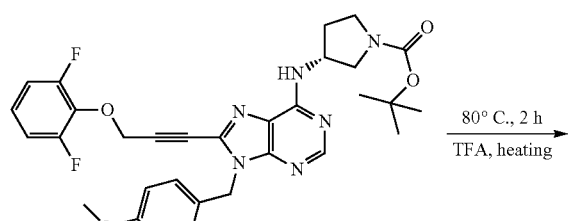

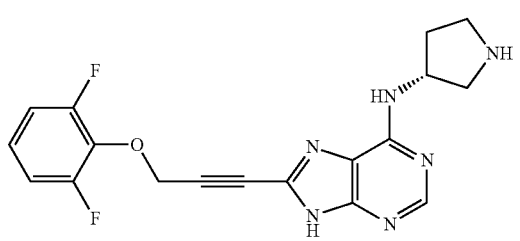

Step 4. Preparation of (R)-8-(3-(2,6-difluorophenoxy)prop-1-yn-1-yl)-N-(pyrrolidin-3-yl)-9H-purin-6-amine The title compound is prepared by using essentially the same procedure as in Example 6, Step 5 affording a solid product (89%), MS (+) ES: 371 (M+H)⁺.

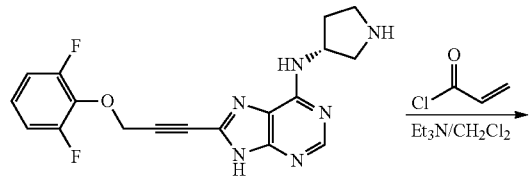

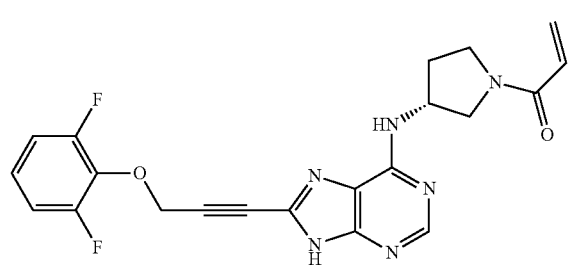

Step 5. Preparation of (R)-1-(3-((8-(3-(2,6-difluorophenoxy)prop-1-yn-1-yl)-9H-purin-6-yl)amino)pyrrolidin-1-yl)prop-2-en-1-one The title compound was prepared by using essentially the same procedure as in Example 6, Step 6 affording a solid product (56%), MS (+) ES: 425 (M+H)⁺.

Example 99

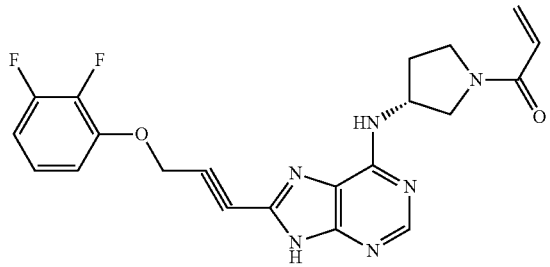 [SMILES: C=CC(=O)N1CC[C@@H](Nc2ncnc3[nH]c(C#CCOc4cccc(F)c4F)nc23)C1]

Preparation of (R)-1-(3-((8-(3-(2,3-difluorophenoxy)prop-1-yn-1-yl)-9H-purin-6-yl)amino)pyrrolidin-1-yl)prop-2-en-1-one The title compound was prepared by using essentially the same procedure as in Example 98 except by using 1,2-difluoro-3-(prop-2-yn-1-yloxy)benzene instead of 1,3-difluoro-2-(prop-2-yn-1-yloxy)benzene in step 3 affording a solid product (56%), MS (+) ES: 425 (M+H)⁺.

Example 100

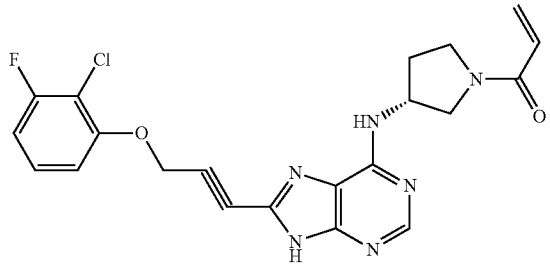 [SMILES: C=CC(=O)N1CC[C@@H](Nc2ncnc3[nH]c(C#CCOc4cccc(F)c4Cl)nc23)C1]

Preparation of (R)-1-(3-((8-(3-(2-chloro-3-fluorophenoxy)prop-1-yn-1-yl)-9H-purin-6-yl)amino)pyrrolidin-1-yl)prop-2-en-1-one The title compound was prepared by using essentially the same procedure as in Example 98 except by using 1-chloro-2-fluoro-3-(prop-2-yn-1-yloxy)benzene instead of 1,3-difluoro-2-(prop-2-yn-1-yloxy)benzene in step 3 affording a solid product (56%), MS (+) ES: 441 (M+H)⁺.

Example 101

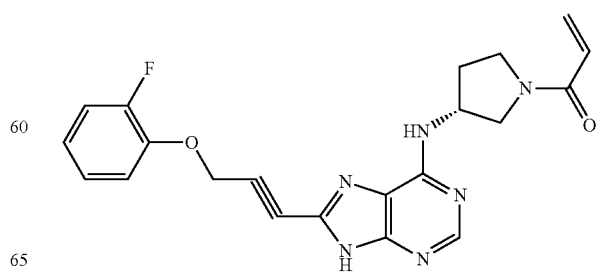

85

Preparation of (R)-1-(3-((8-(3-(2-fluorophenoxy)prop-1-yn-1-yl)-9H-purin-6-yl)amino)pyrrolidin-1-yl)prop-2-en-1-one The title compound was prepared by using essentially the same procedure as in Example 98 except by using 1-fluoro-2-(prop-2-yn-1-yloxy)benzene instead of 1,3-difluoro-2-(prop-2-yn-1-yloxy)benzene in step 3 affording a solid product, MS (+) ES: 407 (M+H)+.

Example 102

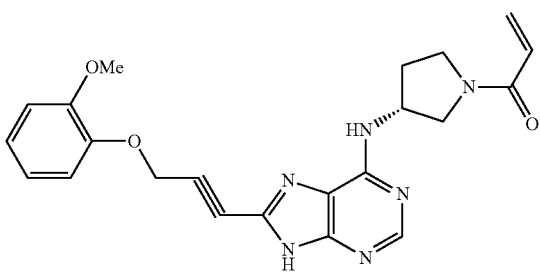 [SMILES: C=CC(=O)N1CC[C@@H](Nc2ncnc3[nH]c(C#CCOc4ccccc4OC)nc23)C1]

Preparation of (R)-1-(3-((8-(3-(2-methoxyphenoxy)prop-1-yn-1-yl)-9H-purin-6-yl)amino)pyrrolidin-1-yl)prop-2-en-1-one The title compound was prepared by using essentially the same procedure as in Example 98 except by using 1-methoxy-2-(prop-2-yn-1-yloxy)benzene instead of 1,3-difluoro-2-(prop-2-yn-1-yloxy)benzene in step 3 affording a solid product, MS (+) ES: 418 (M+H)+.

Reaction scheme 6

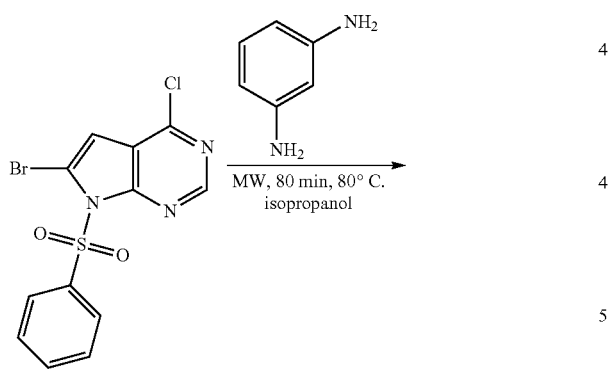

86

-continued

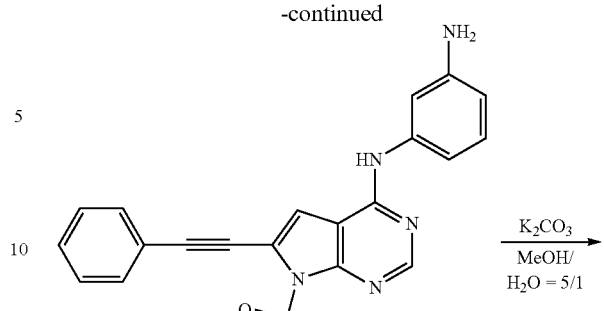

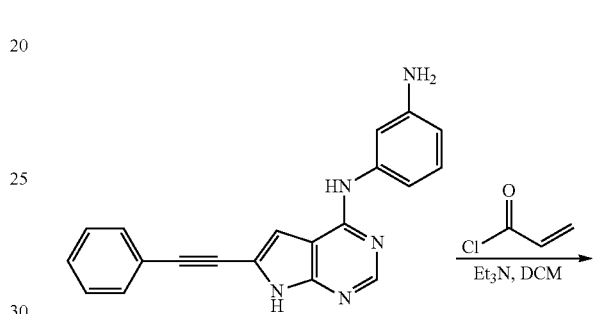

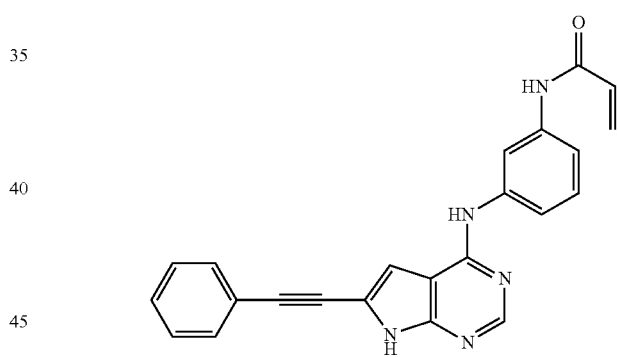

Example 103

Preparation of N-(3-((6-(phenylethynyl)-7H-pyrrolo[2,3-d]pyrimidin-4-yl)amino)phenyl)acrylamide

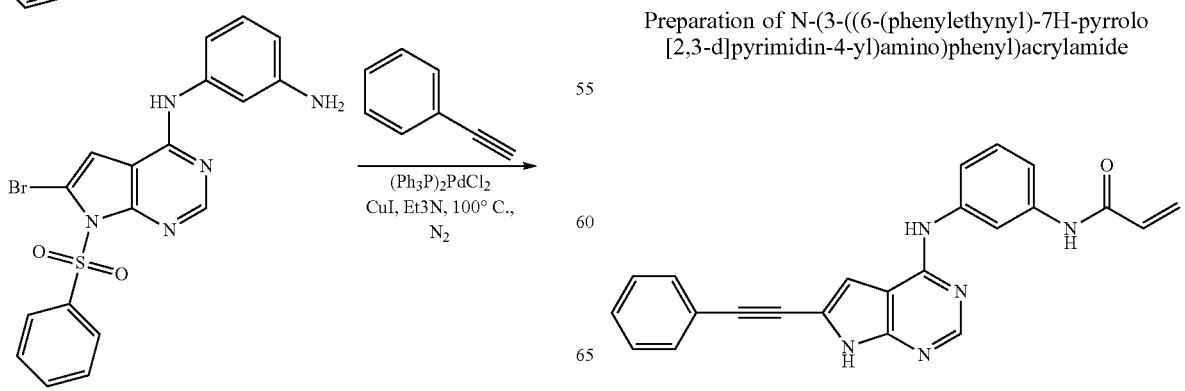

Step 1. Preparation of N1-(6-bromo-7-(phenylsulfonyl)-7H-pyrrolo[2,3-d]pyrimidin-4-yl)benzene-1,3-diamine

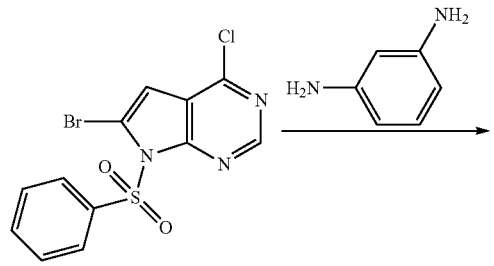

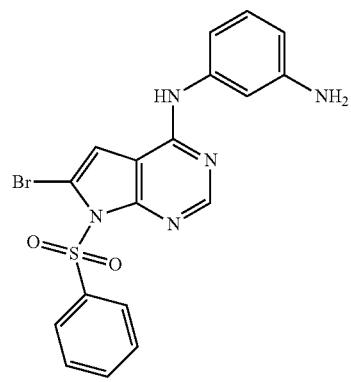

A mixture of 6-bromo-4-chloro-7-(phenylsulfonyl)-7H-pyrrolo[2,3-d]pyrimidine (372 mg, 1 mmol), 1,3-diaminobenzene (216 mg, 2 mmol) and triethylamine (202 mg, 2 mmol) in 15 mL isopropyl alcohol was heated to 80° C. in a microwave for 60 minutes. After cooling, the solvent was evaporated and the residue was directly chromatographed on silica gel with ethyl acetate and hexane as solvents to afford a solid product (260 mg, 60% yield), MS (+) ES: 445 (M+H)$^+$.

Step 2. Preparation of N1-(6-(phenylethynyl)-7-(phenylsulfonyl)-7H-pyrrolo[2,3-d]pyrimidin-4-yl)benzene-1,3-diamine

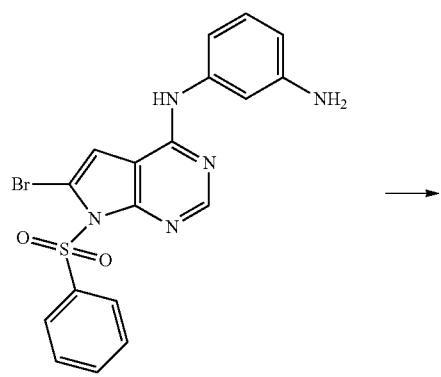

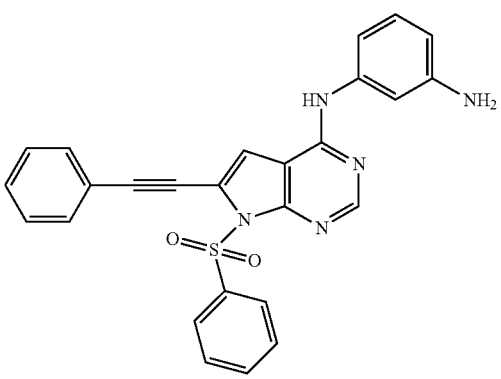

This compound was prepared by using essentially the same procedure as in Example 1 (Step 4) affording a solid product, MS (+) ES: 466 (M+H)$^+$.

Step 3. Preparation of N1-(6-(phenylethynyl)-7H-pyrrolo[2,3-d]pyrimidin-4-yl)benzene-1,3-diamine

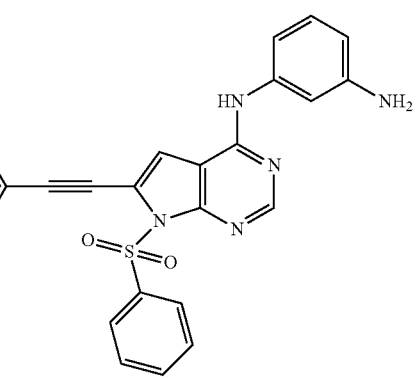

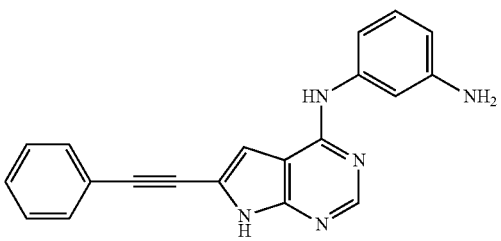

This compound was prepared by using essentially the same procedure as in Example 1 (Step 5) affording a solid product, MS (+) ES: 326 (M+H)$^+$.

Step 4. Preparation of N-(3-((6-(phenylethynyl)-7H-pyrrolo[2,3-d]pyrimidin-4-yl)amino)phenyl)acrylamide

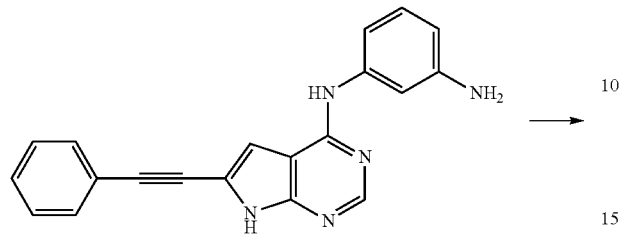

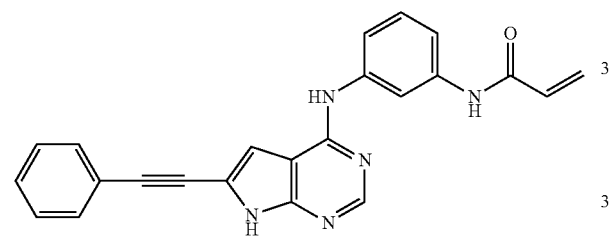

This compound was prepared by using essentially the same procedure as in Example 1 (Step 7) affording a solid product, MS (+) ES: 380 (M+H)⁺.

Example 104

Preparation of N-(3-((6-(thiophen-3-ylethynyl)-7H-pyrrolo[2,3-d]pyrimidin-4-yl)amino)phenyl)acrylamide

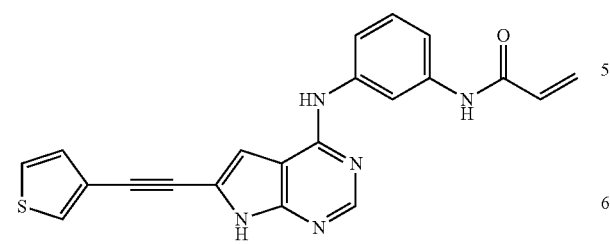

This compound was prepared by using essentially the same procedure as in Example 103 except in step 2 by using 3-ethynylthiophene instead of ethynylbenzene affording a solid product, MS (+) ES: 385 (M+H)⁺.

Example 105

Preparation of N-(3-((6-((4-chlorophenyl)ethynyl)-7H-pyrrolo[2,3-d]pyrimidin-4-yl)amino)phenyl)acrylamide This compound was prepared by using essentially the same procedure as in Example 103 except in step 2 by using 1-chloro-4-ethynylbenzene instead of ethynylbenzene affording a solid product, MS (+) ES: 414 (M+H)⁺.

Example 106

Evaluation of BTK Binding and Cell Inhibition Data Methods for Biochemical and Cell-Based Assays—

Btk kinase assay—The Btk kinase assay was performed using a ADP-Glo Btk kinase assay kit purchased from Promega (Madison, Wis.). The assay was conducted according to the protocols provided in the assay kit. In brief, the enzyme reaction was carried out in the kinase reaction buffer containing Btk (2 ng/µl), ATP (1.2 µM), poly GT peptide (0.3 µM), DTT (40 nM), MnCl2 (1.4 mM), and 1 xkinase buffer (included in the kit) in the presence or absence of the tested articles at various concentrations in 384-well plate at room temperature (22±1° C.) for 60 minutes. The final reaction volume for each reaction was 10 µl. Then, 4 µl of ADP-Glo reagent (included in the kit) was added into the reaction and the plate was further incubated for another 40 minutes to terminate the reaction and deplete the remaining ATP. Finally, 10 µl of the kinase detection reagent was added into each reaction to simultaneously convert ADP to ATP and allow the newly synthesized ATP to be measured by a plate-reading luminometer (Victor X5 2030 multilabel reader, PerkinElmer). IC50 value was calculated using appropriate programs in GraphPad Prism by plotting the logarithm of the concentration versus percent inhibition as compared with a vehicle (DMSO) control. The $IC_{50}$ values for the Example compounds are shown in Table 1.

Cell proliferation assay: TMD-8 and SU-DHL-1 cells were maintained at 37° C. in a humidified atmosphere with 5% $CO_2$ in the recommended medium and serum concentrations. For cell proliferation assay, cells were seeded in 96-well pates at a density of 5,000 to 10,000 cells per well and cultured overnight at 37° C. in recommended medium supplemented with 5-10% FBS. On the next day, the test articles at various concentrations or vehicle control (0.5% DMSO) were added into cell culture. After 5-day treatment, the growth of cells was assayed by the CellTiter-Glo® Luminestceaent Cell Viability Assay (Promega). $IC_{50}$ values were calculated using GraphPad Prism by plotting the logarithm of the concentration versus percent inhibition of cell growth as compared with the vehicle control. The $IC_{50}$ values for the Example compounds are shown in Table 1.

TABLE I

| Test Cmpd (Example No.) | BTK ADP-Glo (IC$_{50}$ μM) | TMD8 cell growth (GI$_{50}$ μM) |
|---|---|---|
| 1 | 0.109 | 0.054 |
| 2 | 0.0033 | 0.034 |
| 3 | 0.0023 | 2.9 |
| 4 | 0.06 | 0.157 |
| 5 | 0.257 | 1.66 |
| 6 | 0.0164 | 0.019 |
| 7 | 0.003 | 0.141 |
| 8 | 0.332 | 0.357 |
| 9 | 0.0026 | 0.012 |
| 10 | 0.0001 | 0.171 |
| 11 | 0.06 | 1.17 |
| 12 | 0.0003 | 1.3 |
| 13 | 0.0019 | 0.019 |
| 14 | 0.015 | 0.134 |
| 15 | 0.0148 | 0.019 |
| 16 | 0.0006 | 0.003 |
| 17 | 0.212 | 0.25 |
| 18 | 0.00002 | 0.002 |
| 19 | 0.022 | 0.148 |
| 20 | 0.0005 | 0.051 |
| 21 | 0.004 | 1.8 |
| 22 | 0.00002 | 1.002 |
| 23 | 0.0015 | 0.107 |
| 24 | 0.001 | 0.01 |
| 25 | 0.001 | 0.006 |
| 26 | 0.0065 | 0.247 |
| 27 | 0.016 | 0.094 |
| 28 | 0.0004 | 0.082 |
| 29 | 0.0007 | 1.21 |
| 30 | 0.019 | 1.2 |
| 31 | 0.0016 | 0.02 |
| 32 | 0.0075 | 0.004 |
| 34 | 0.0003 | 0.107 |
| 35 | 0.0004 | 0.950 |
| 36 | 0.127 | 0.552 |
| 37 | 1.180 | N/T |
| 38 | 0.384 | 0.209 |
| 39 | 0.192 | 0.299 |
| 40 | 0.0003 | 0.004 |
| 41 | 0.00008 | 0.069 |
| 42 | 0.0014 | 0.001 |
| 43 | 0.00014 | 0.001 |
| 44 | 0.00011 | 0.012 |
| 45 | 0.0011 | 0.0014 |
| 46 | 0.00004 | 0.017 |
| 47 | 0.136 | 0.008 |
| 48 | 0.432 | 0.088 |
| 49 | <0.00003 | 0.017 |
| 50 | 0.011 | 0.009 |
| 51 | 0.018 | 0.016 |
| 52 | 0.006 | 0.187 |
| 53 | 0.023 | 0.006 |
| 54 | 0.0035 | 0.121 |
| 55 | 0.174 | 0.195 |
| 56 | 0.323 | 1 |
| 57 | 0.024 | 0.01 |
| 58 | 0.0004 | 0.171 |
| 59 | 0.742 | 1.97 |
| 60 | 0.011 | 0.005 |
| 61 | 0.121 | 0.022 |
| 62 | 0.052 | 0.024 |
| 63 | 0.0048 | 0.0027 |
| 64 | 0.0002 | 0.005 |
| 65 | 0.173 | 0.0027 |
| 66 | 0.215 | 0.0012 |
| 67 | 0.272 | 0.004 |
| 68 | 0.187 | 0.003 |
| 69 | 0.182 | 0.007 |
| 70 | 0.0072 | 0.0013 |
| 71 | 0.01 | 0.001 |
| 72 | 0.0035 | 0.0007 |
| 73 | 0.0001 | 0.001 |
| 74 | 0.00003 | 0.0012 |
| 75 | 0.03 | 0.0049 |
| 76 | 0.001 | 0.0032 |
| 77 | 0.145 | 0.526 |
| 78 | 0.702 | 2.68 |
| 79 | 0.002 | 0.031 |
| 80 | 0.255 | 0.51 |
| 81 | 0.033 | 0.003 |
| 82 | 0.038 | 0.0045 |
| 83 | 0.008 | 0.0017 |
| 84 | 0.136 | 1.09 |
| 85 | 0.007 | 0.091 |
| 86 | 0.018 | 0.018 |
| 87 | 0.043 | 0.002 |
| 88 | 0.018 | 0.02 |
| 89 | 0.148 | 0.006 |
| 90 | 0.014 | 0.014 |
| 91 | 0.008 | 0.0015 |
| 92 | 0.043 | 0.0038 |
| 93 | 0.578 | 4.2 |
| 94 | 0.346 | 3.58 |
| 95 | 0.404 | 0.066 |
| 96 | 0.014 | 0.066 |
| 97 | 0.027 | 0.004 |
| 98 | 0.006 | 0.005 |
| 99 | 0.0003 | 0.001 |
| 100 | 0.032 | 0.006 |
| 101 | 0.001 | 0.003 |
| 102 | 0.0002 | 0.004 |
| 103 | 0.0003 | 0.079 |
| 104 | 0.006 | 0.017 |
| 105 | 0.155 | 0.048 |

What is claimed is:

1. A compound of formula (I), or a pharmaceutically acceptable salt thereof,

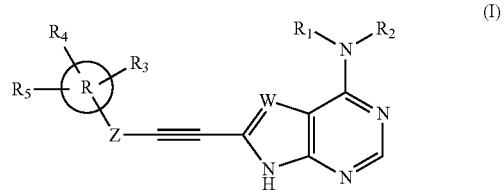

wherein Z is selected from the group consisting of —(CH$_2$)$_m$—, —O(CH$_2$)$_m$—, and —(CH2)$_m$O(CH$_2$)$_m$—; and where m is an integer from 1-3;

W is CH or N;

R is a cyclic group selected from the group consisting of phenyl, naphthalenyl, benzodioxolyl, benzofuranyl, benzothiophenyl, thiophenyl, quinolinyl, cyclohexyl, furanyl, pyrazolyl, tetrahydropyranyl, and indazolyl, wherein R is either unsubstituted or substituted with one or more of R$^3$, R$^4$ and R$^5$;

R$^1$ and R$^2$ are independently selected from the group consisting of H, alkyl, alkenyl, alkynyl, C$_3$-C$_8$ cycloalkyl, C$_3$-C$_8$ cycloheteroalkyl, aryl, and heteroaryl; or R$^1$ and R$^2$ may combine with an atom or atoms to which they are attached to form 3- to 12-membered heterocyclic, C$_{6-12}$ aryl, or 5- to 12-membered heteroaryl, wherein R$^1$ and R$^2$ are independently either unsubstituted or substituted with a substituent selected from the group consisting of —C(O)CH=CH$_2$, —C(O)CH=CHCH$_2$N(CH$_3$)$_2$, —C(O)CH=CHCH$_2$NH(CH$_3$), —C(O)CH=CHCH$_3$,

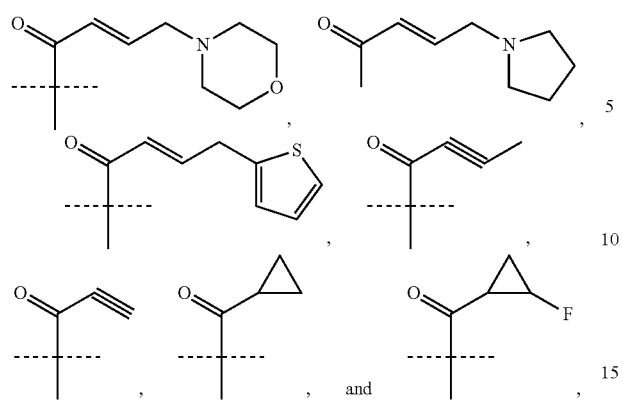

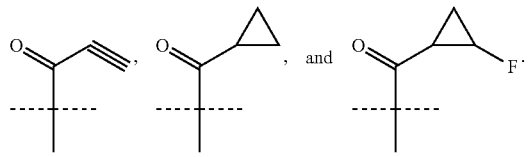

provided that at least one of R¹ and R² is not hydrogen; and

R³, R⁴ and R⁵ are each independently selected from the group consisting of H, halogen, —CN, —CF₃, —OCF₃, —OR⁹, alkyl;

wherein R⁹ is alkyl.

2. The compound of claim 1, or a pharmaceutically acceptable salt thereof, wherein Z is —OCH₂.

3. The compound of claim 1, or a pharmaceutically acceptable salt thereof, wherein R³, R⁴ and R⁵ are each independently selected from the group consisting of H, F, Cl, —OCH₃, —OCF₃, —CH₃, —CF₃, and —CN.

4. The compound of claim 1, or a pharmaceutically acceptable salt thereof, wherein R¹ and R² combine the nitrogen to which they are attached to form an unsubstituted or substituted piperazinyl.

5. The compound of claim 4, or a pharmaceutically acceptable salt thereof, wherein the piperazinyl is substituted with a substituent selected from the group consisting of —C(O)CH═CH₂, —C(O)CH═CHCH₂N(CH₃)₂, and

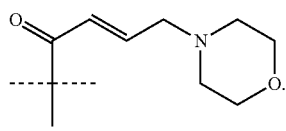

6. The compound of claim 1, or a pharmaceutically acceptable salt thereof, wherein R² is an unsubstituted or substituted pyrrolidinyl, an unsubstituted or substituted piperidinyl, or an unsubstituted or substituted phenyl.

7. The compound of claim 1, or a pharmaceutically acceptable salt thereof, wherein R² is pyrrolidinyl substituted with a substituent selected from the group consisting of —C(O)CH═CH₂, —C(O)CH═CHCH₂N(CH₃)₂, —C(O)CH═CHCH₂NH(CH₃), —C(O)CH═CHCH₃

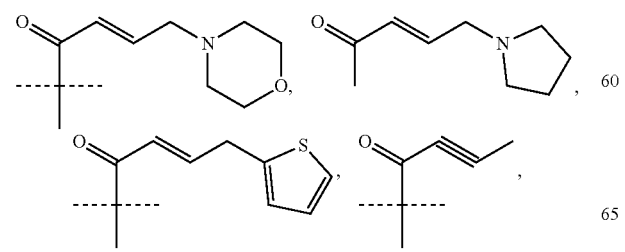

8. The compound of claim 1, or a pharmaceutically acceptable salt thereof, having a formula selected from the group consisting:

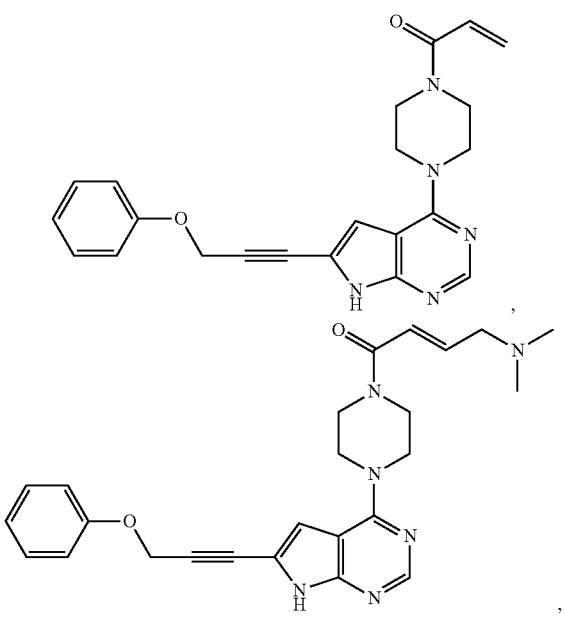

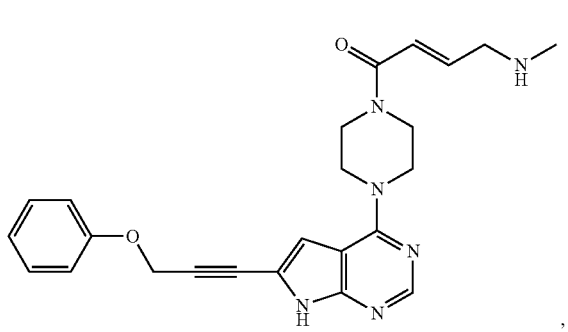

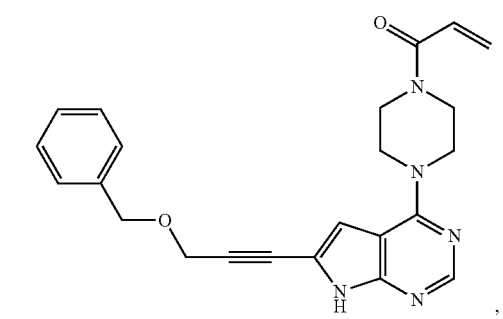

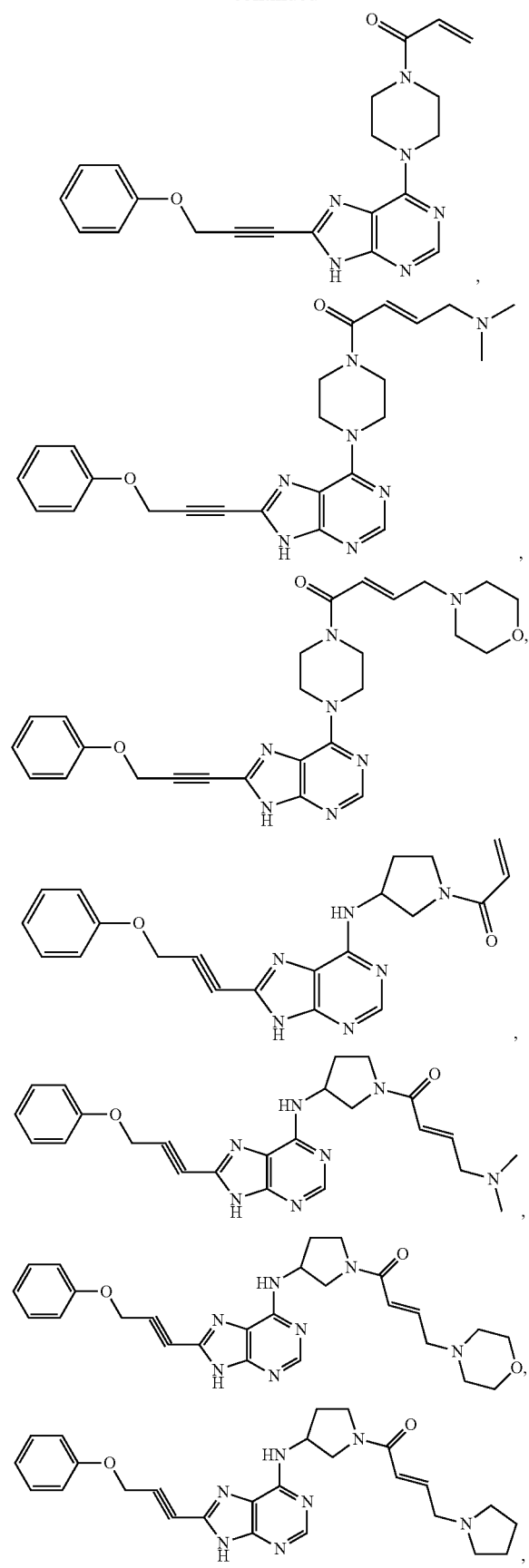
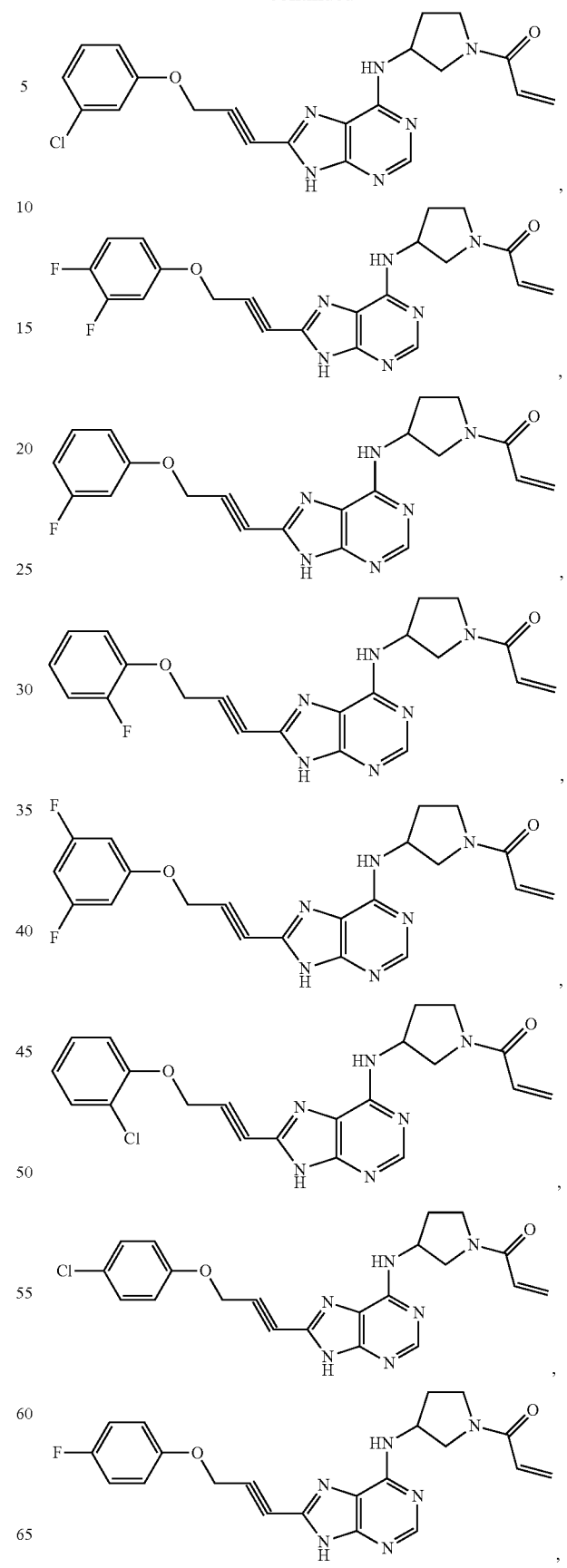

97
-continued
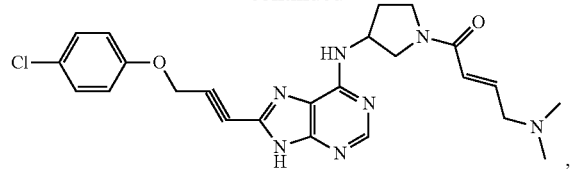,
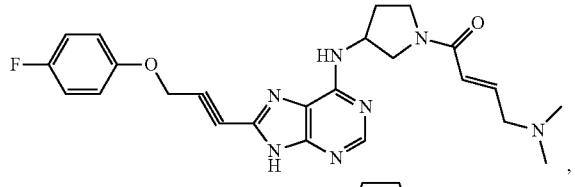,
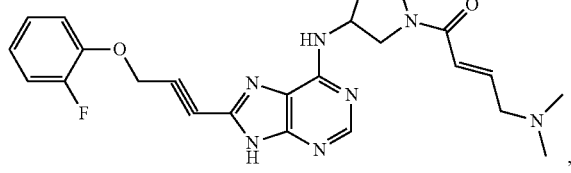,
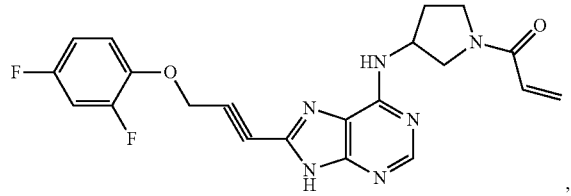,
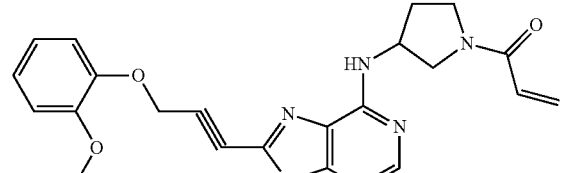,
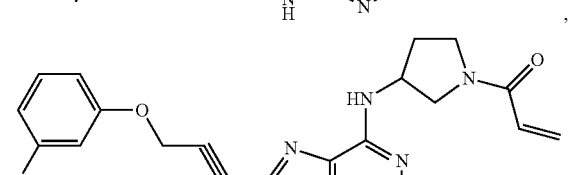,
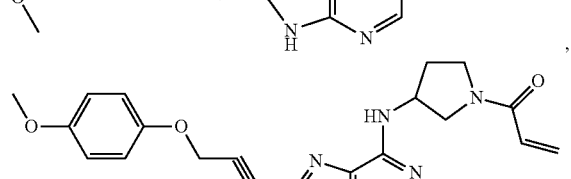,
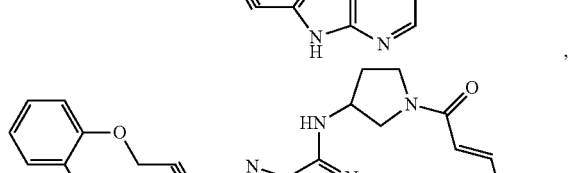,
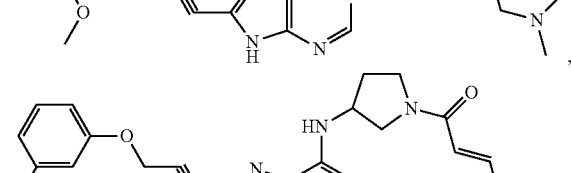,
98
-continued
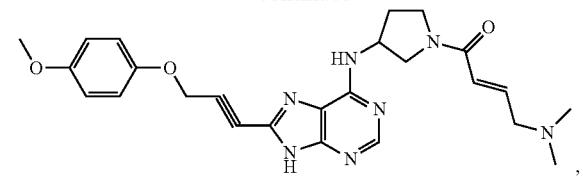,
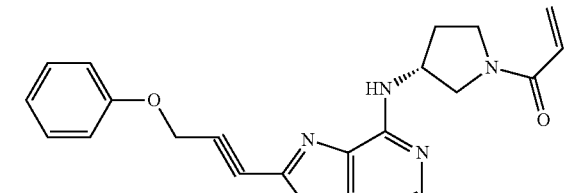,
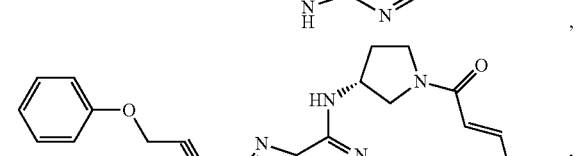,
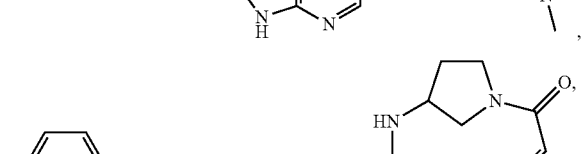,
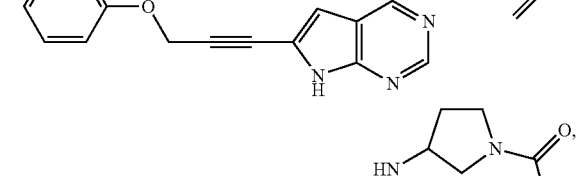,
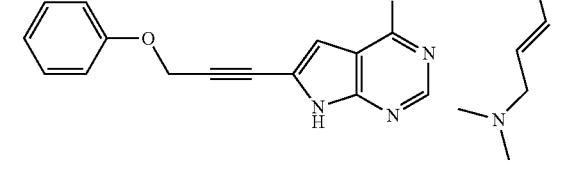,
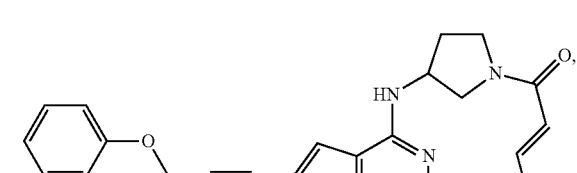,
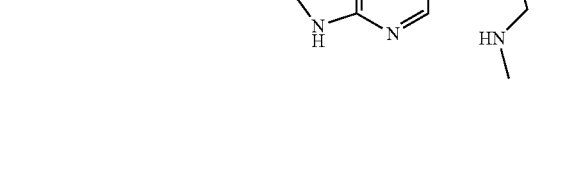,
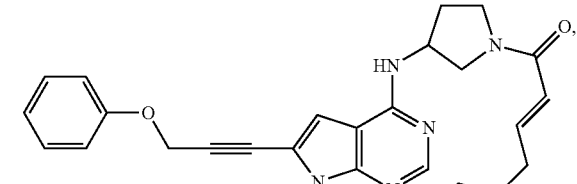, 99
-continued
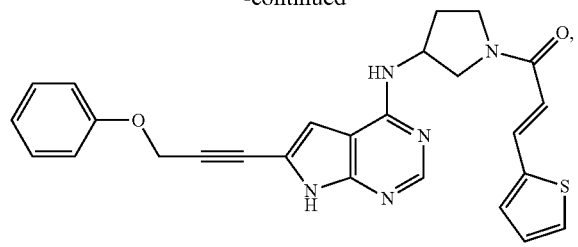
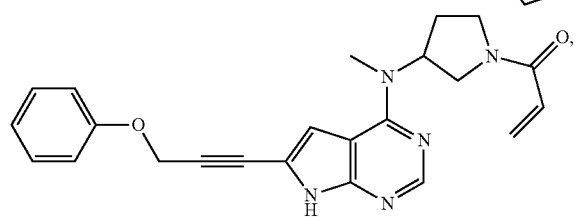
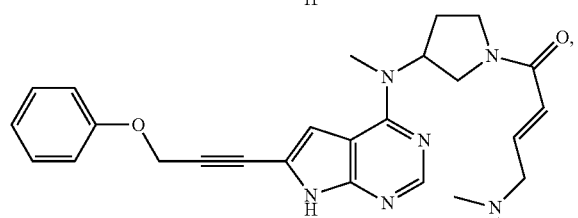
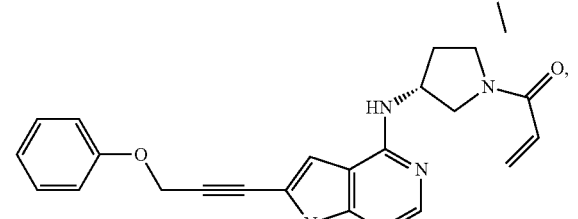
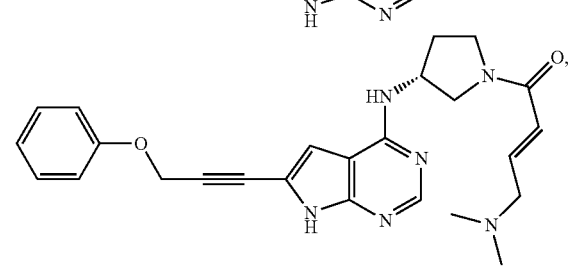
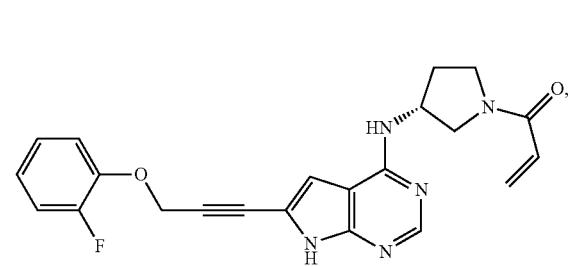
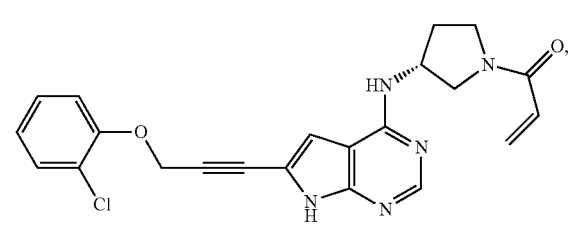
100
-continued
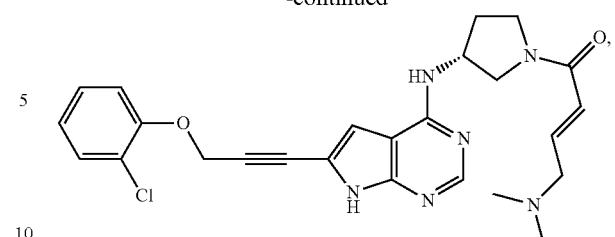
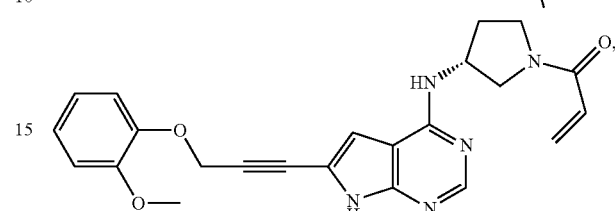
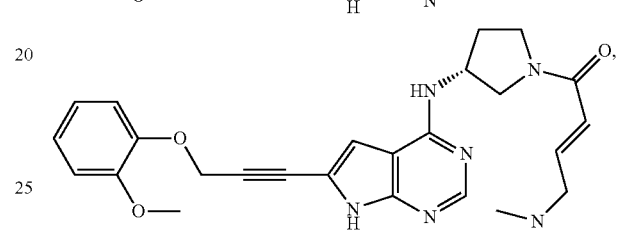
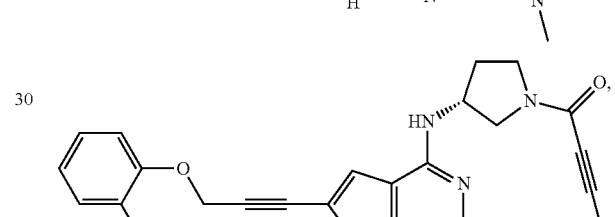
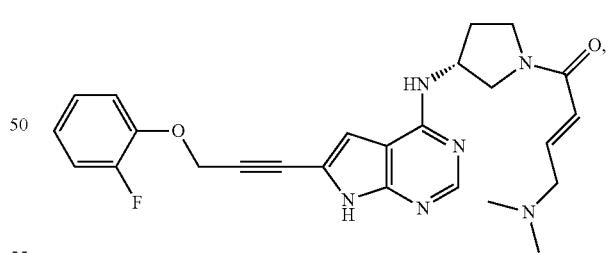

101
-continued
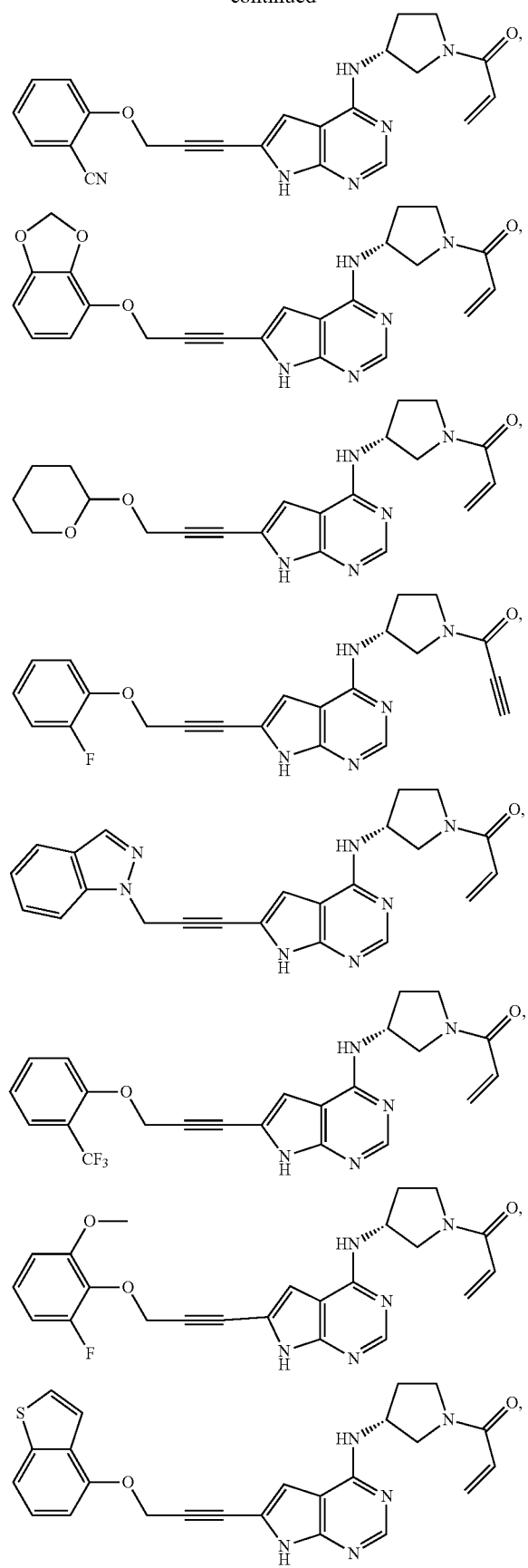
102
-continued
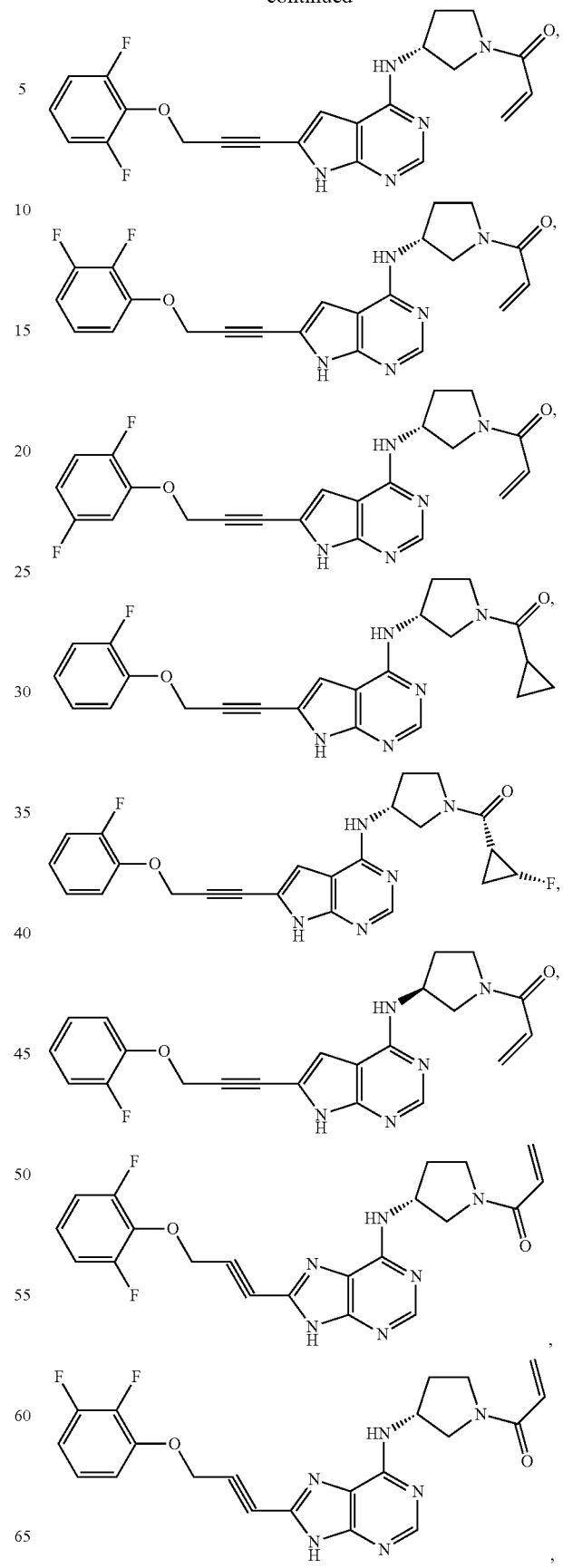

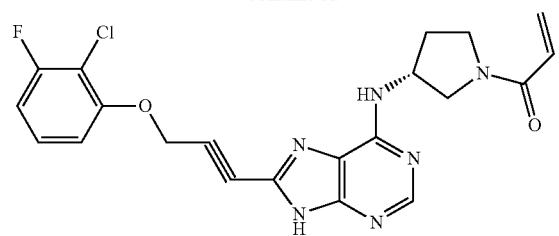
,
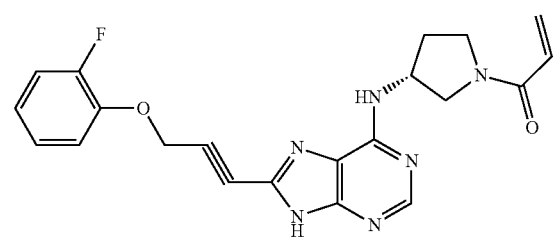
and
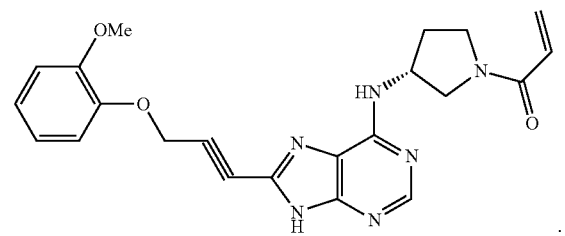
.
9. A pharmaceutical composition comprising the compound of claim 1 and a pharmaceutically acceptable carrier.
10. The compound of claim 8, or a pharmaceutically acceptable salt thereof, having a formula selected from the group consisting:
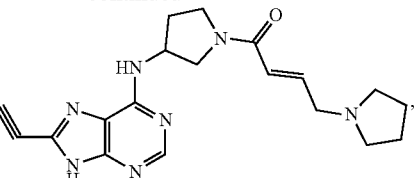
,
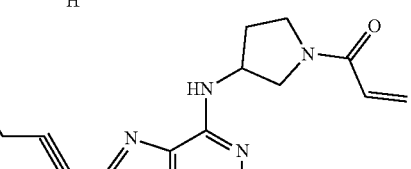
,
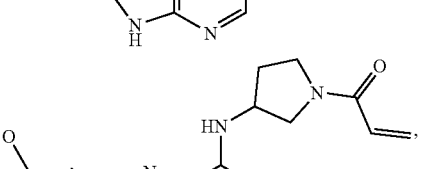
,
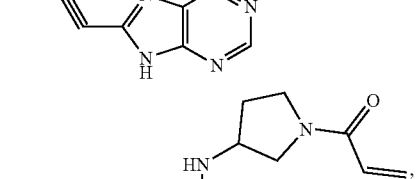
,
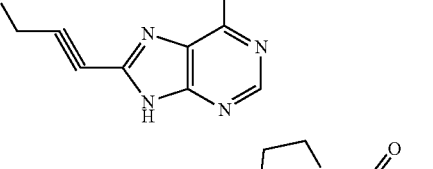
,
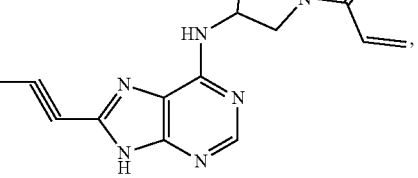
,
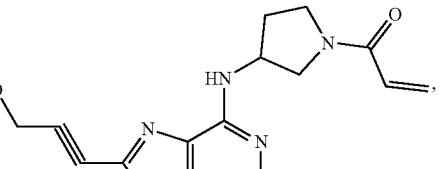
,
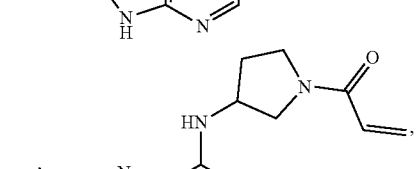
,
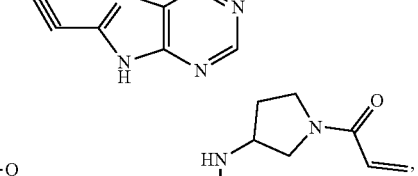
,
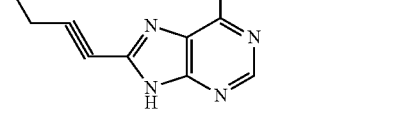
,

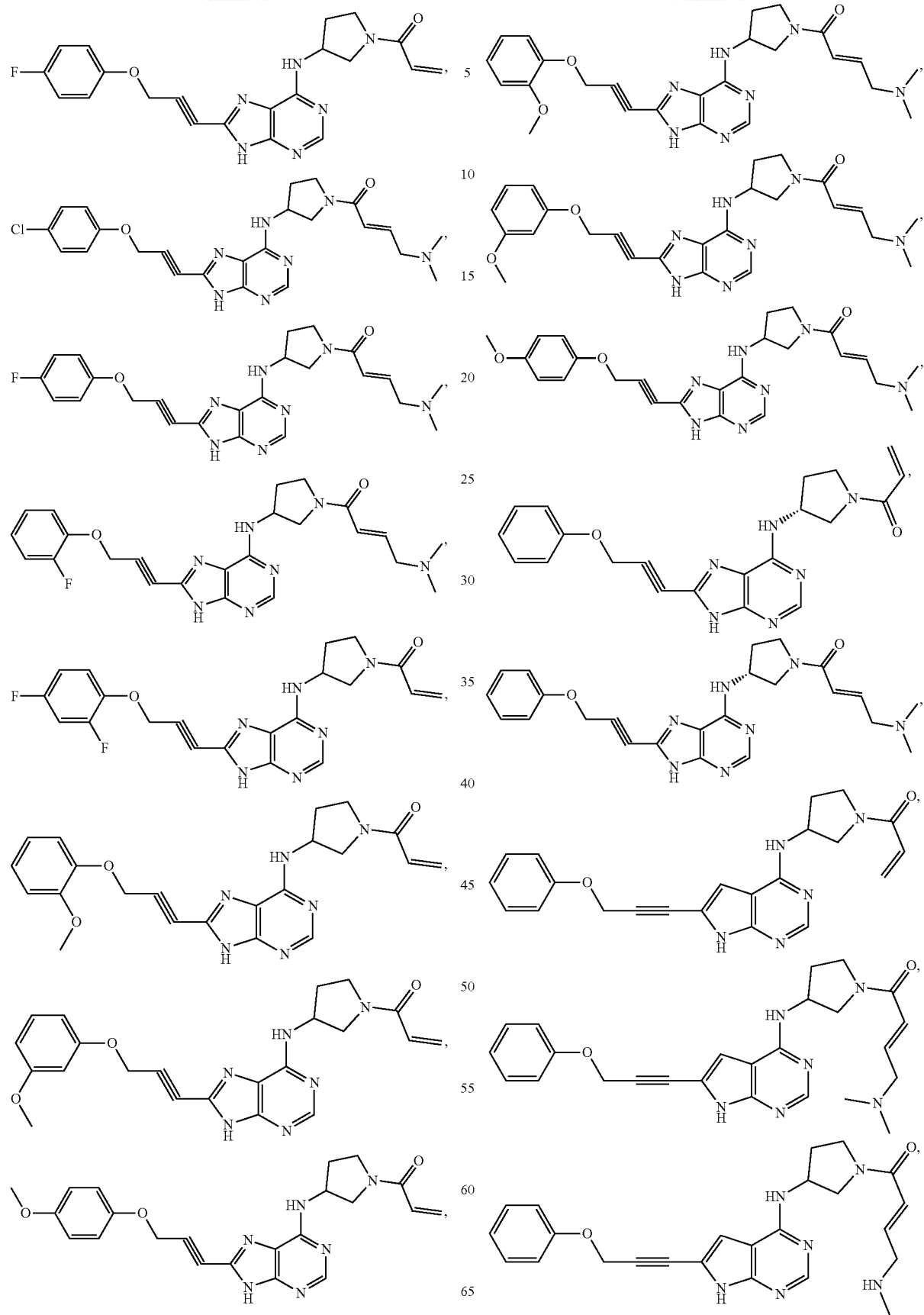

107
-continued
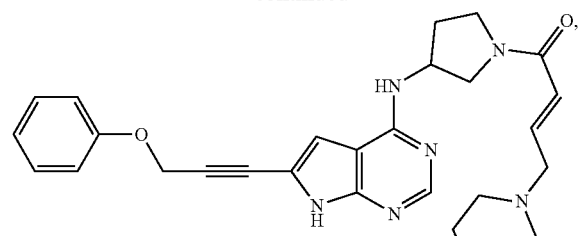
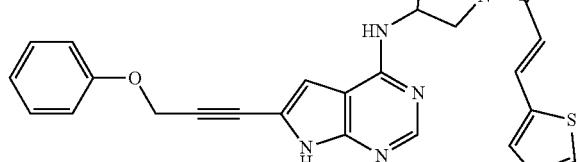
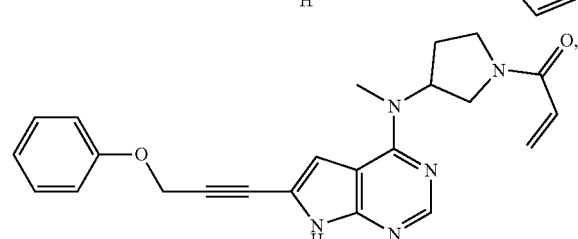
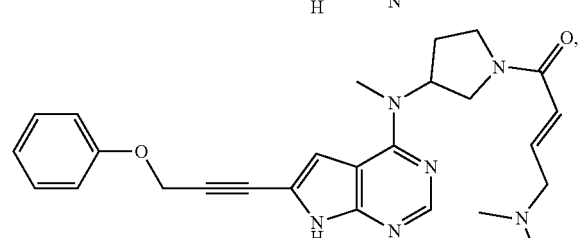
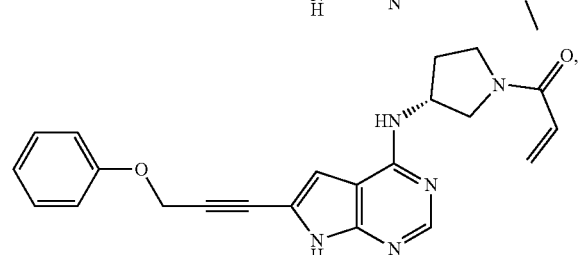
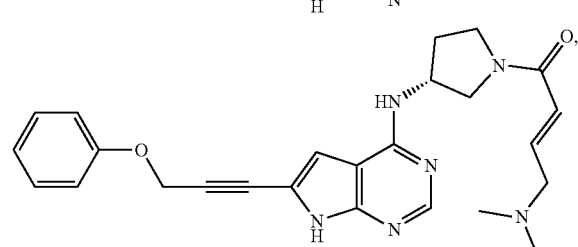
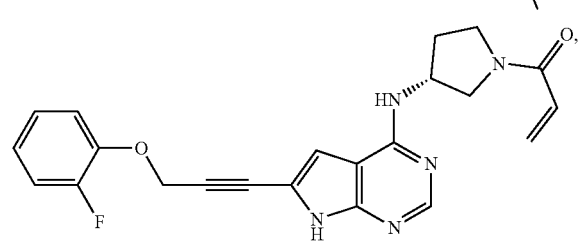
108
-continued
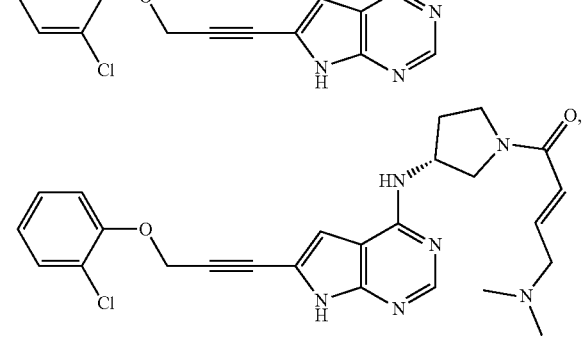
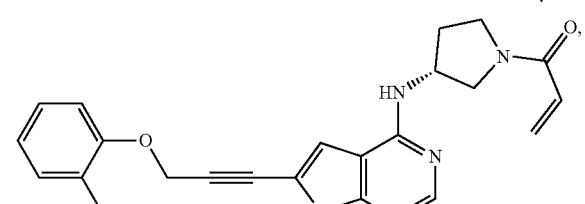
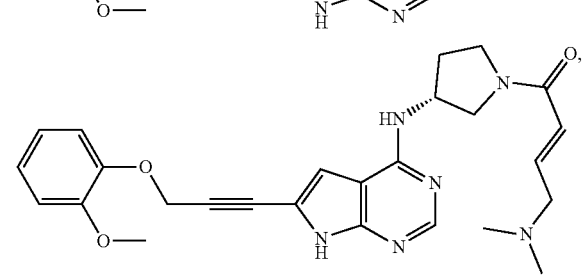
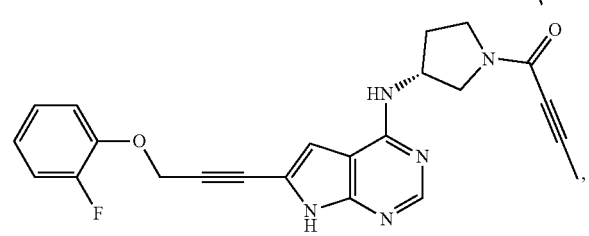
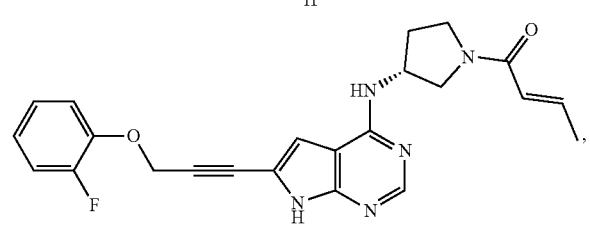
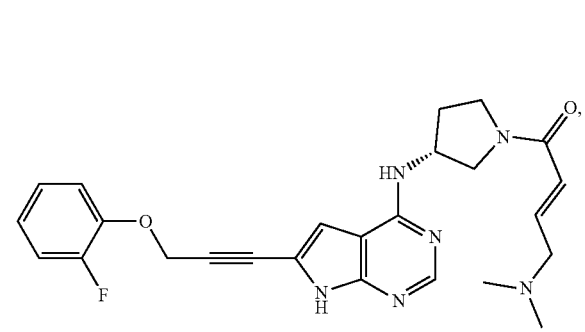

109
-continued
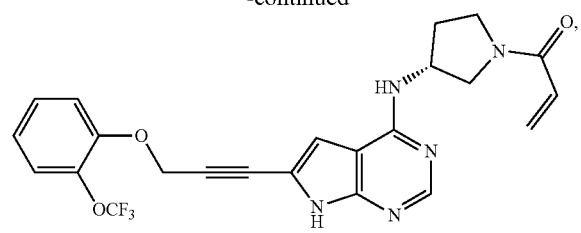
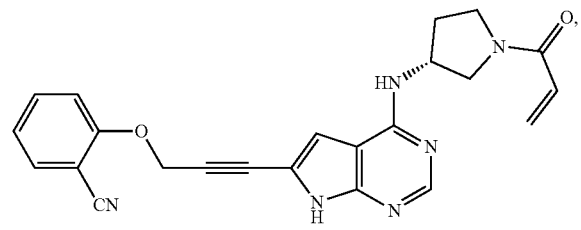
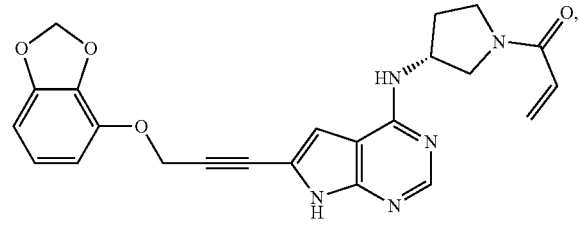
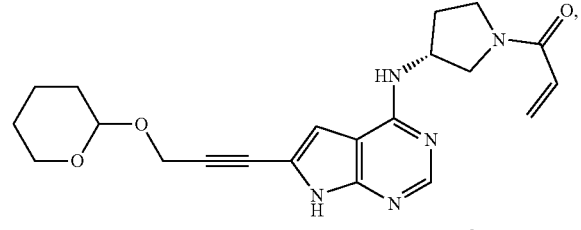
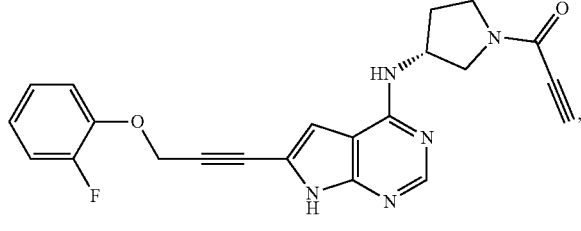
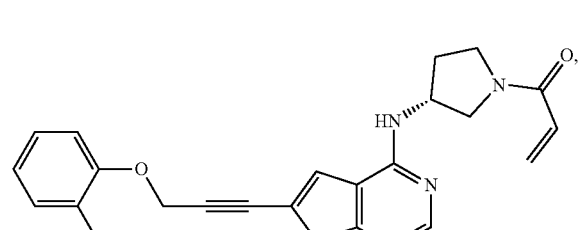
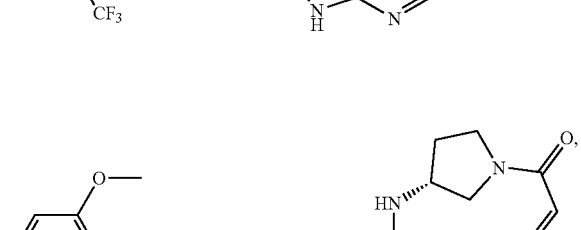
110
-continued
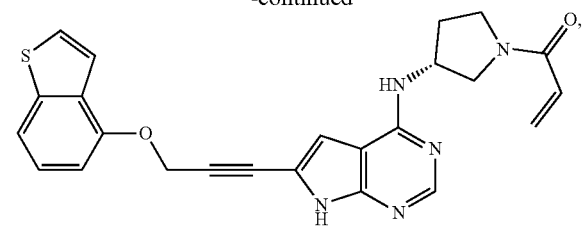
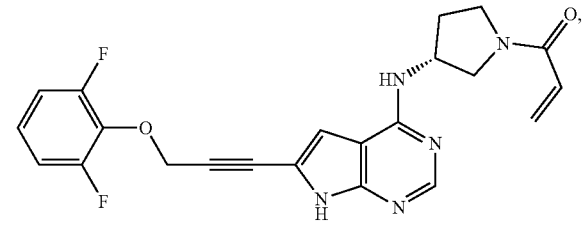
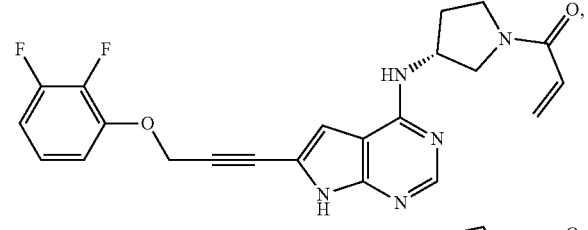
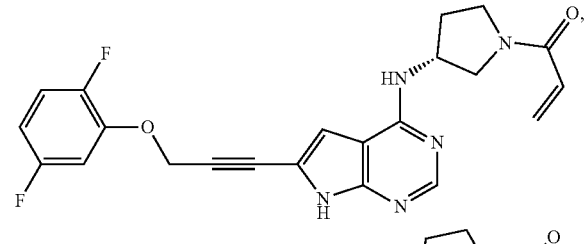
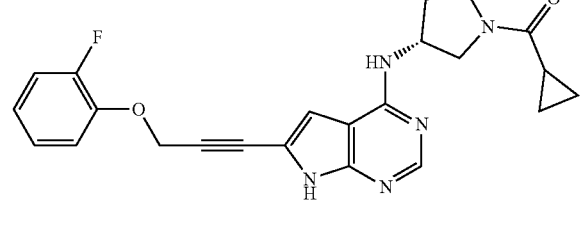
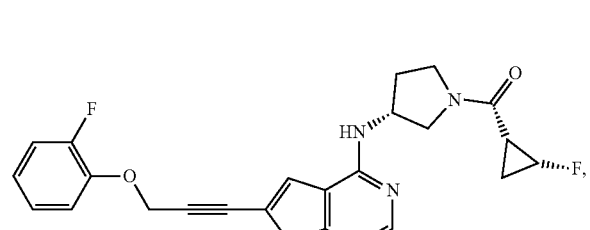
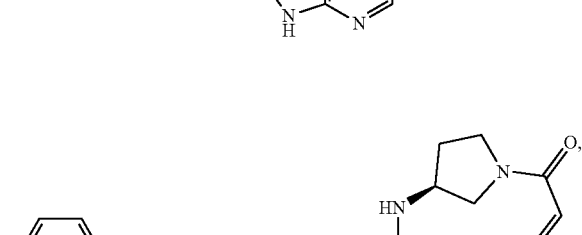

-continued
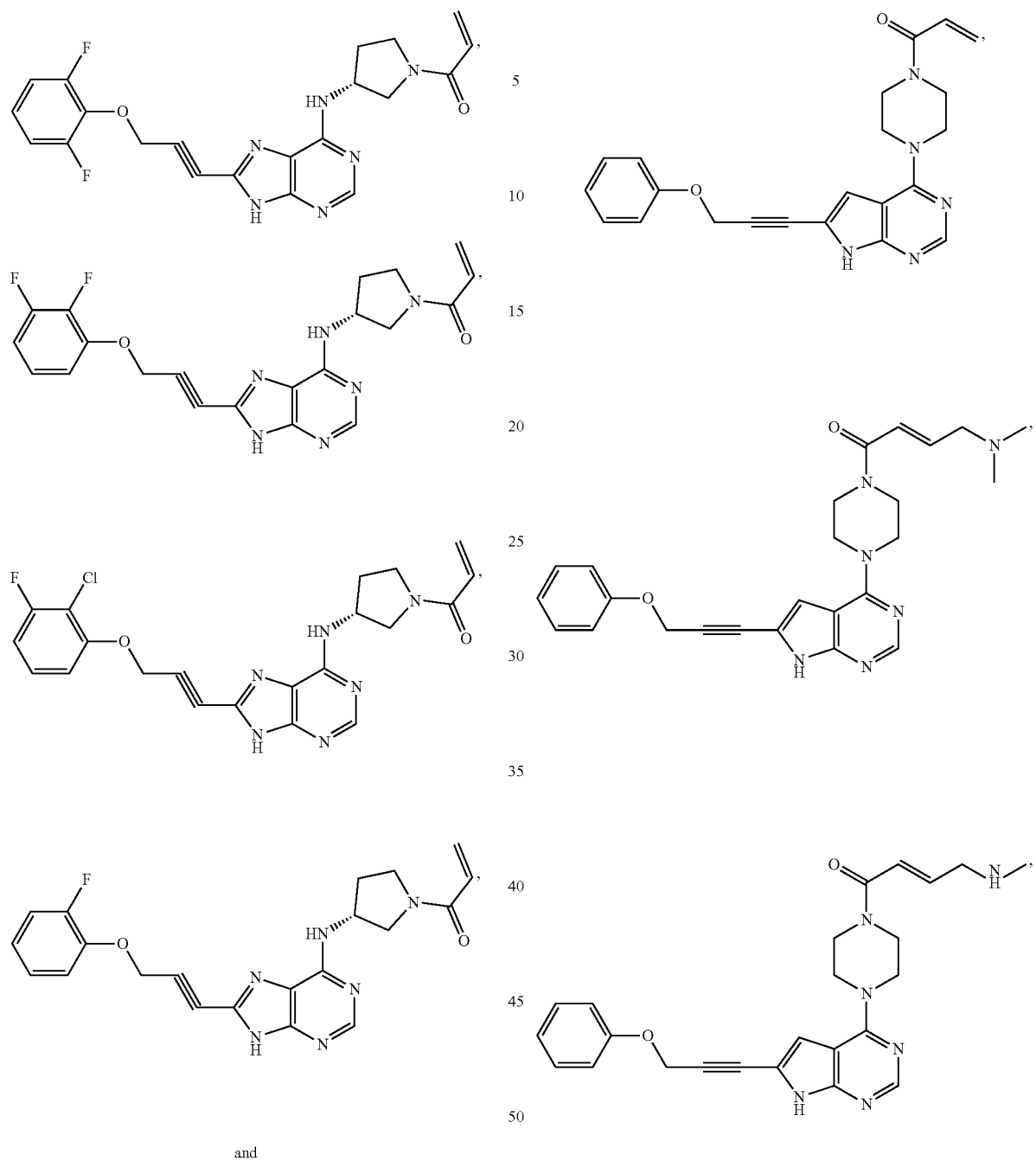
11. The compound of claim 8, or a pharmaceutically acceptable salt thereof, having a formula selected from the group consisting:
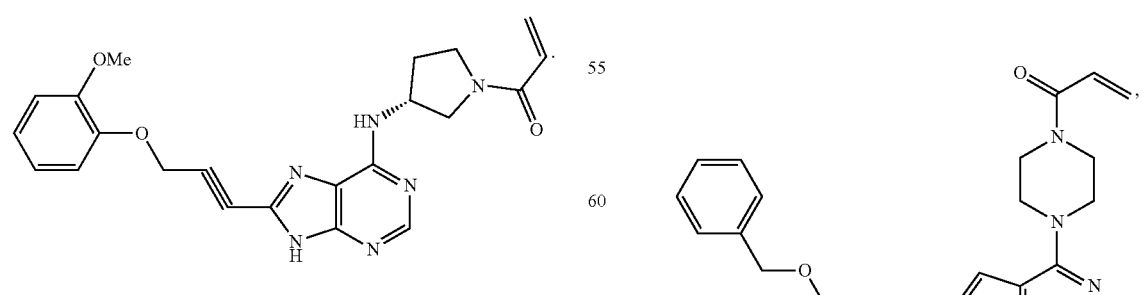

113
-continued
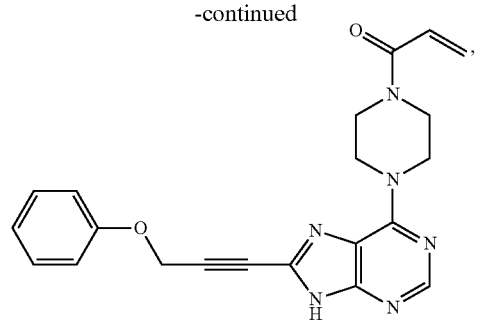
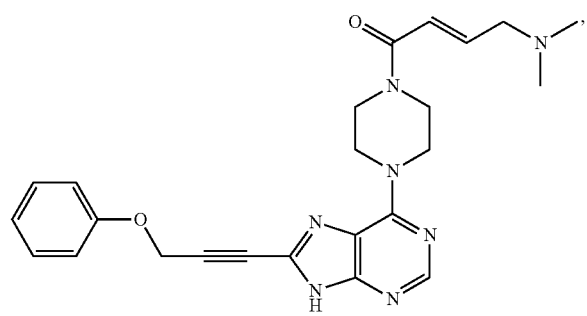
114
-continued
and
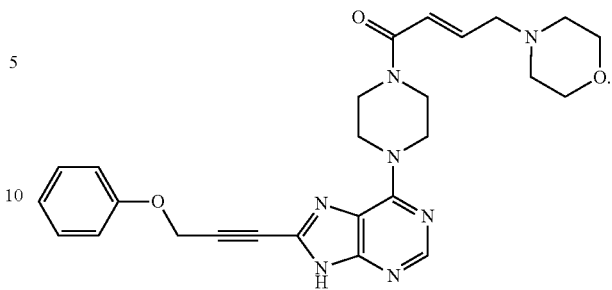
12. The compound of claim 8, or a pharmaceutically acceptable salt thereof, having a formula
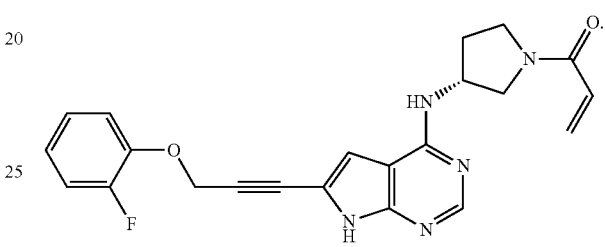
* * * * *